United States Patent
Bong et al.

(10) Patent No.: US 11,884,511 B2
(45) Date of Patent: Jan. 30, 2024

(54) STERILIZATION MODULE, AND STERILIZATION APPARATUS AND ULTRAVIOLET IRRADIATION DEVICE COMPRISING SAME

(71) Applicant: SUZHOU LEKIN SEMICONDUCTOR CO., LTD., Taicang (CN)

(72) Inventors: Sang Hoon Bong, Seoul (KR); Sung June Park, Seoul (KR); Sang Hun An, Seoul (KR); Dae Hun Kim, Seoul (KR)

(73) Assignee: SUZHOU LEKIN SEMICONDUCTOR CO., LTD., Taicang (CN)

( * ) Notice: Subject to any disclaimer, the term of this patent is extended or adjusted under 35 U.S.C. 154(b) by 492 days.

(21) Appl. No.: 17/258,988

(22) PCT Filed: Jul. 5, 2019

(86) PCT No.: PCT/KR2019/008266
§ 371 (c)(1),
(2) Date: Jan. 8, 2021

(87) PCT Pub. No.: WO2020/013529
PCT Pub. Date: Jan. 16, 2020

(65) Prior Publication Data
US 2021/0276834 A1 Sep. 9, 2021

(30) Foreign Application Priority Data

Jul. 10, 2018 (KR) .......................... 10-2018-0080052
Jul. 10, 2018 (KR) .......................... 10-2018-0080053
(Continued)

(51) Int. Cl.
*B66B 31/00* (2006.01)
*A61L 2/10* (2006.01)

(52) U.S. Cl.
CPC ................ *B66B 31/00* (2013.01); *A61L 2/10* (2013.01); *A61L 2202/20* (2013.01)

(58) Field of Classification Search
None
See application file for complete search history.

(56) References Cited

U.S. PATENT DOCUMENTS 9,410,979 B2 * 8/2016 Yuen .................. A63B 22/0605
11,305,028 B2 * 4/2022 Kim .......................... A61L 2/10
(Continued)

FOREIGN PATENT DOCUMENTS

| CN | 101443255 A | 5/2009 |
|---|---|---|
| KR | 10-1231264 B1 | 2/2013 |

(Continued)

*Primary Examiner* — Kavel Singh
(74) *Attorney, Agent, or Firm* — Birch, Stewart, Kolasch & Birch, LLP

(57) ABSTRACT

An embodiment discloses a sterilization module comprising: a frame including a support part that includes one surface and one end, and a fastening part connected to the one end; a first circuit board disposed in the fastening part; and an ultraviolet irradiation device disposed on the first circuit board, wherein the support part comprises: the other end facing the one end; and a side end facing the other end. The frame comprises: a protrusion connected to the side end of the support part; and a guide part connected to the other end of the support part. The fastening part and the guide part extend in a first direction perpendicular to one surface of the support part, and the protrusion extends in a direction opposite to the first direction. The guide part comprises: a first guide part and a second guide part that are spaced apart from each other in a second direction parallel to the one end. The other end comprises a recess between the first guide part and the second guide part, wherein the recess is concave toward the one end.

20 Claims, 39 Drawing Sheets

(30) Foreign Application Priority Data

Jul. 10, 2018 (KR) .......................... 10-2018-0080054
Jul. 30, 2018 (KR) .......................... 10-2018-0088630

(56) References Cited

U.S. PATENT DOCUMENTS

| | | | |
|---|---|---|---|
| 11,548,765 B2 * | 1/2023 | Kim .......................... | B66B 29/04 |
| 2009/0175031 A1 | 7/2009 | Winkelhake et al. | |
| 2014/0322073 A1 | 10/2014 | Link et al. | |
| 2018/0099842 A1 | 4/2018 | Kim et al. | |

FOREIGN PATENT DOCUMENTS

| | | |
|---|---|---|
| KR | 10-2016-0112422 A | 9/2016 |
| KR | 10-2017-0099499 A | 9/2017 |

* cited by examiner

[FIG. 1]
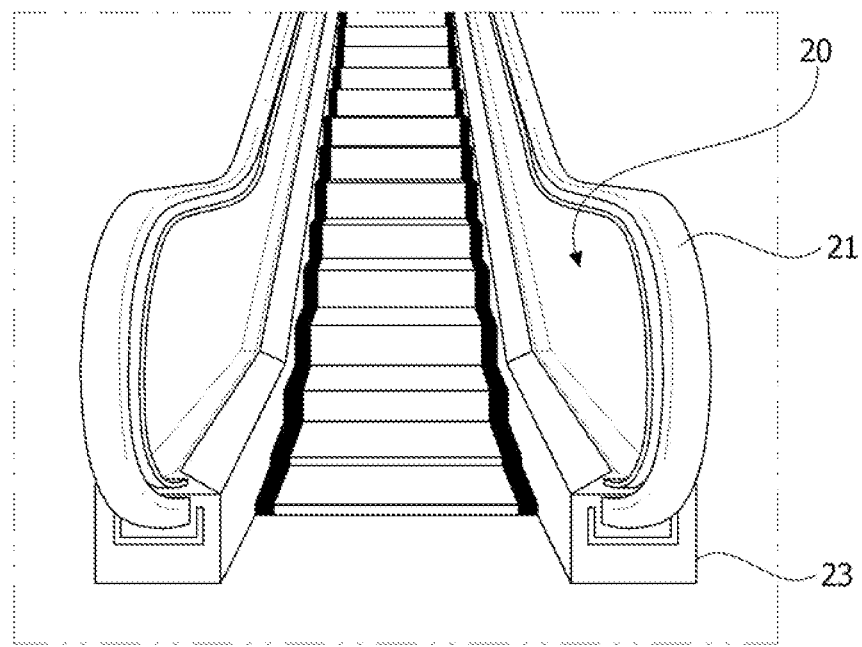
[FIG. 2]
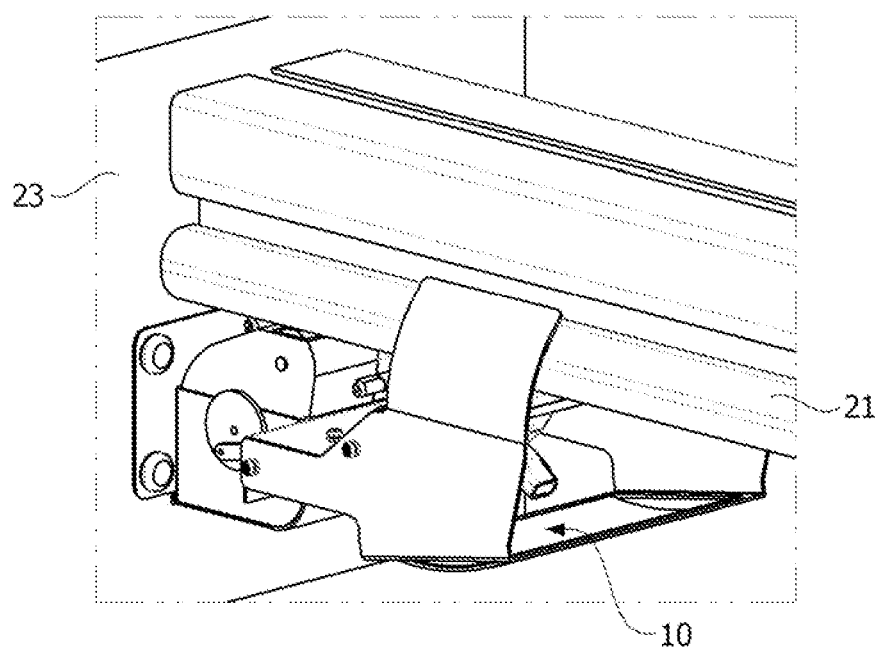

[FIG. 3]
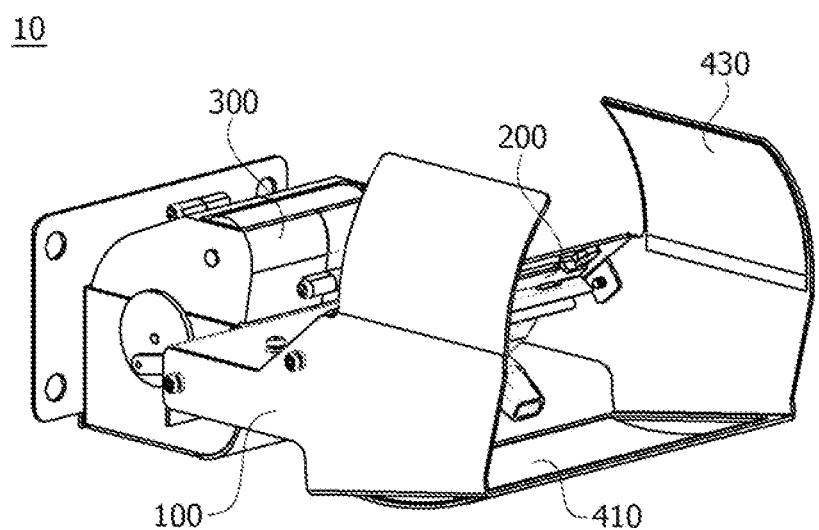
[FIG. 4]
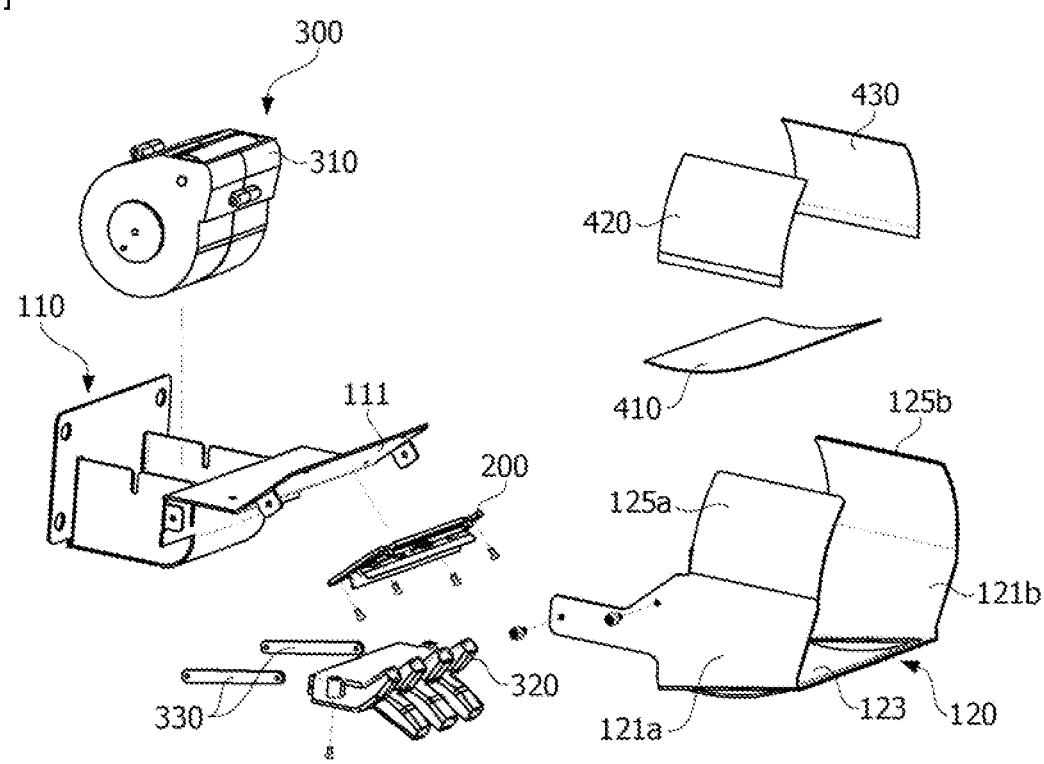

[FIG. 5]
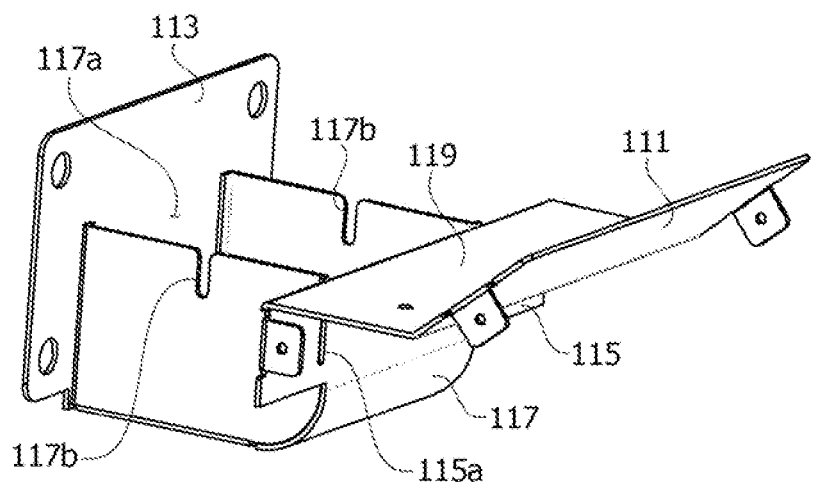
[FIG. 6]
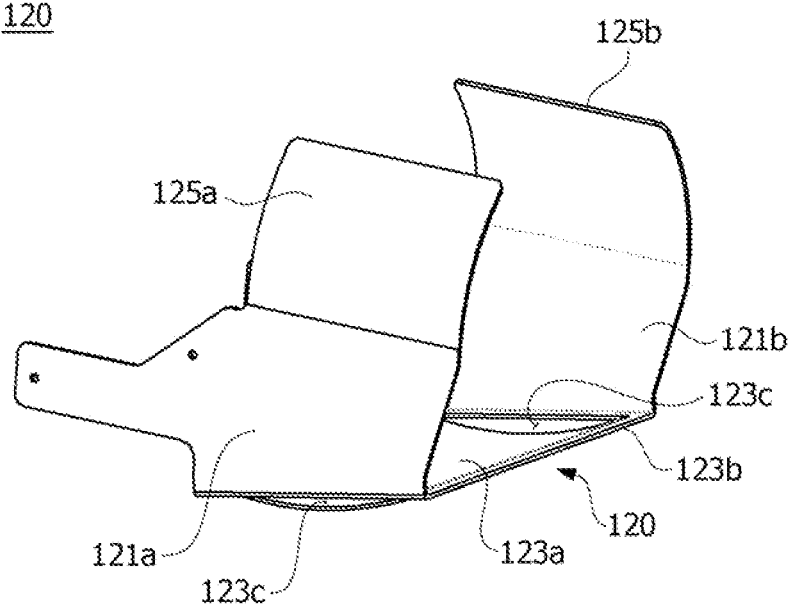

[FIG. 7]
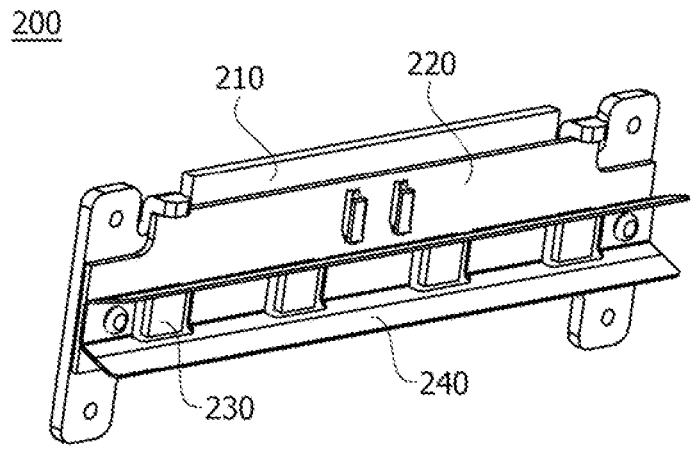
[FIG. 8]
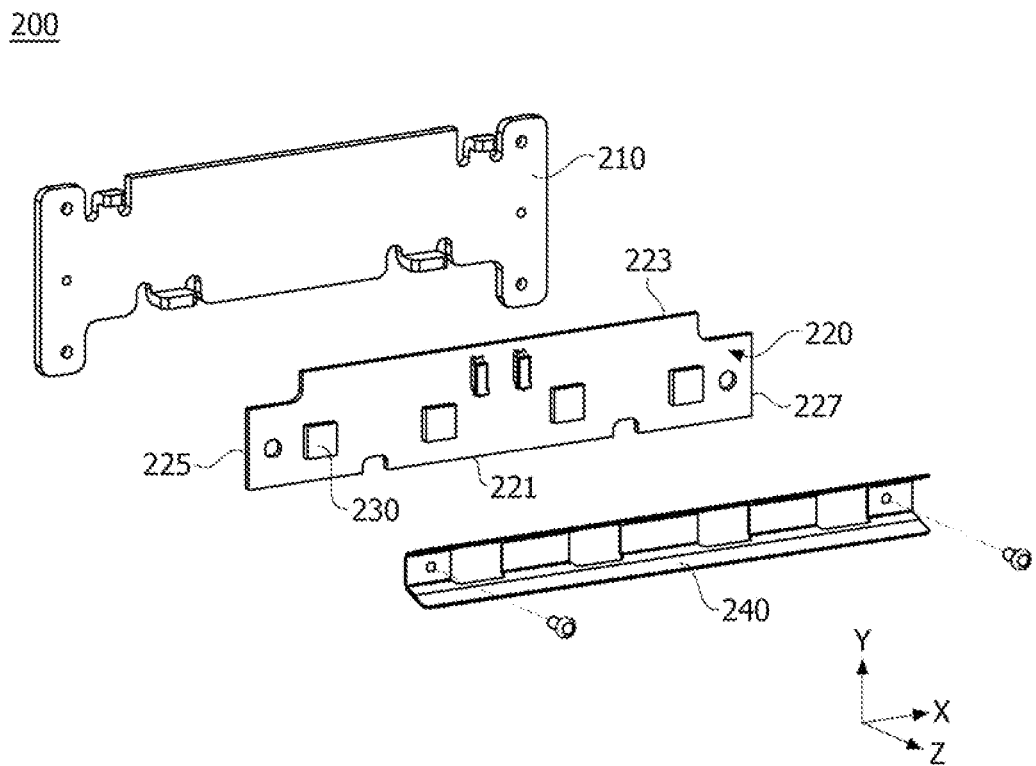

[FIG. 9]
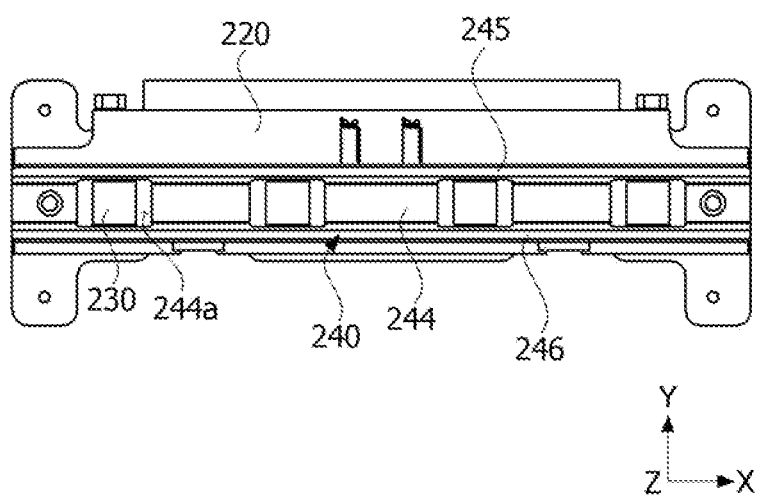

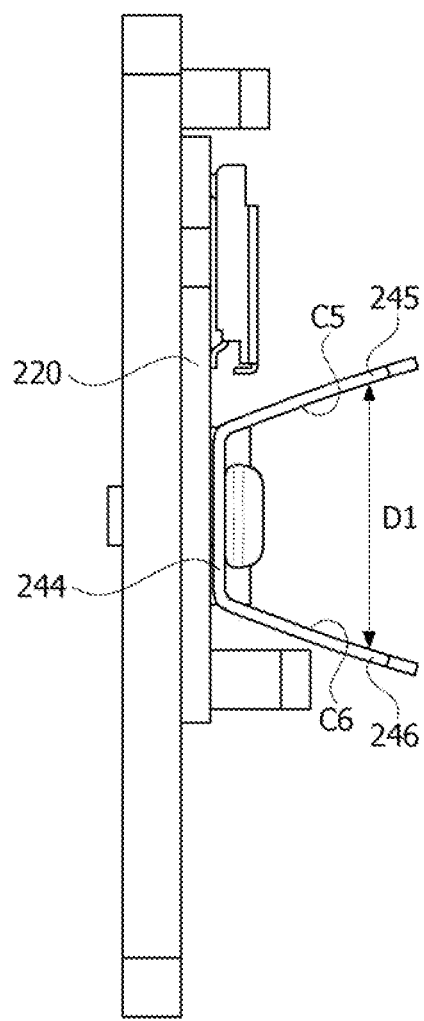
[FIG. 10]

[FIG. 11]
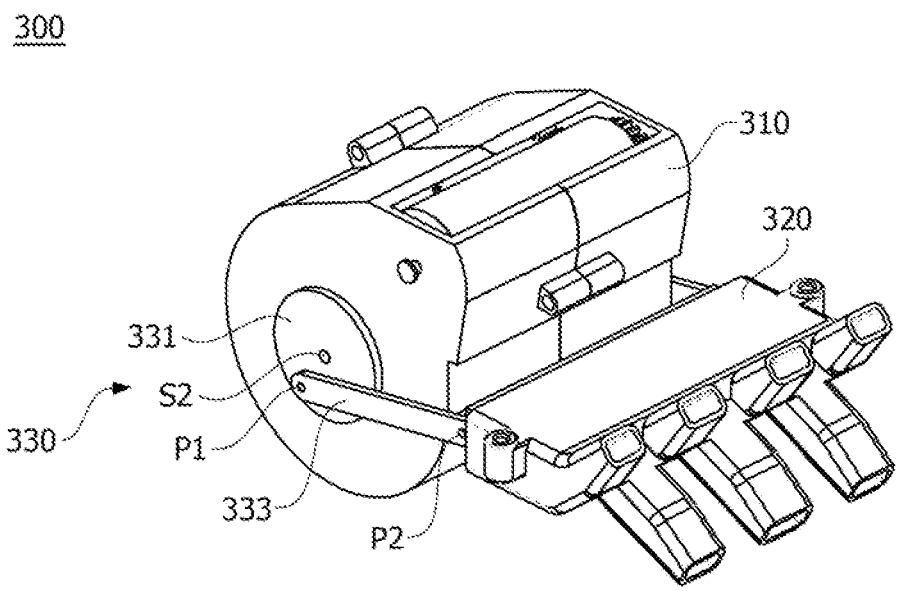
[FIG. 12]
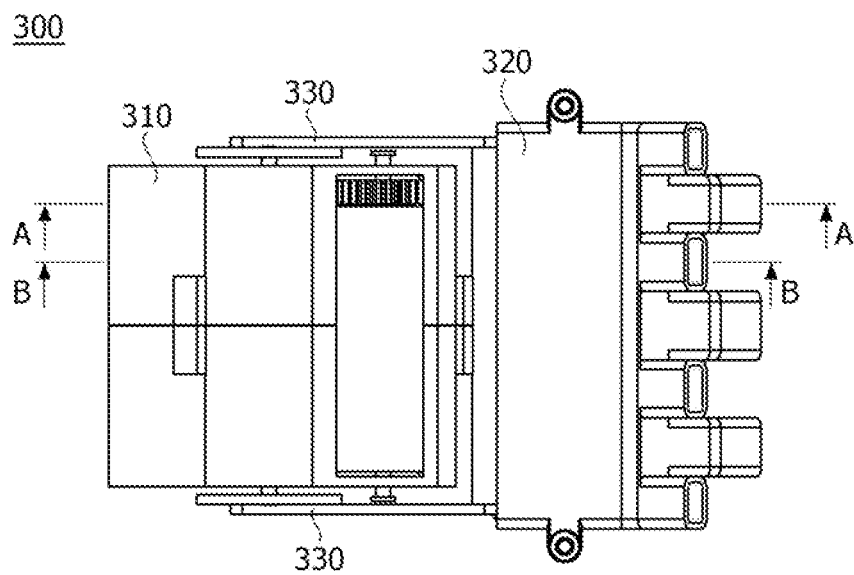

[FIG. 13]
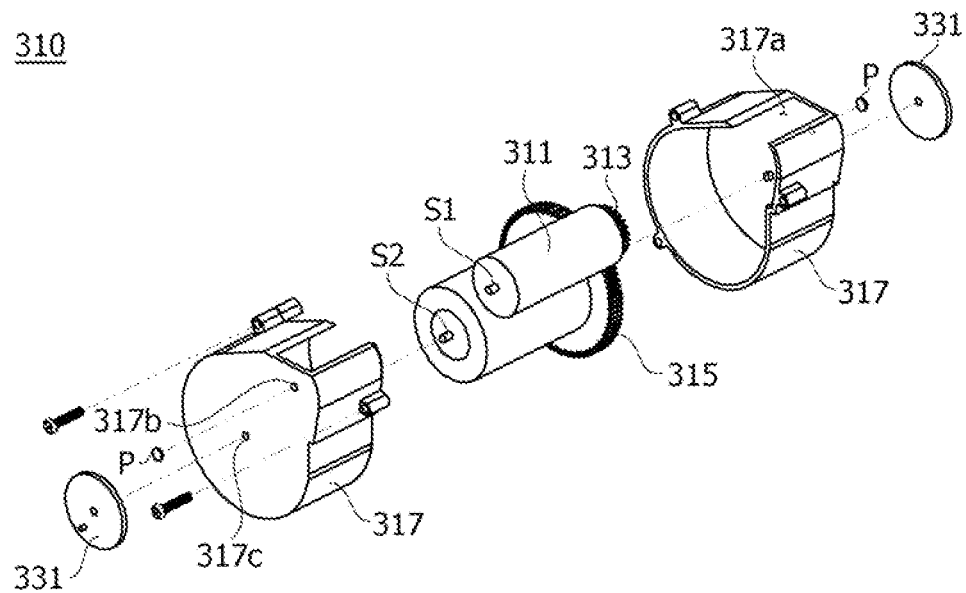
[FIG. 14]
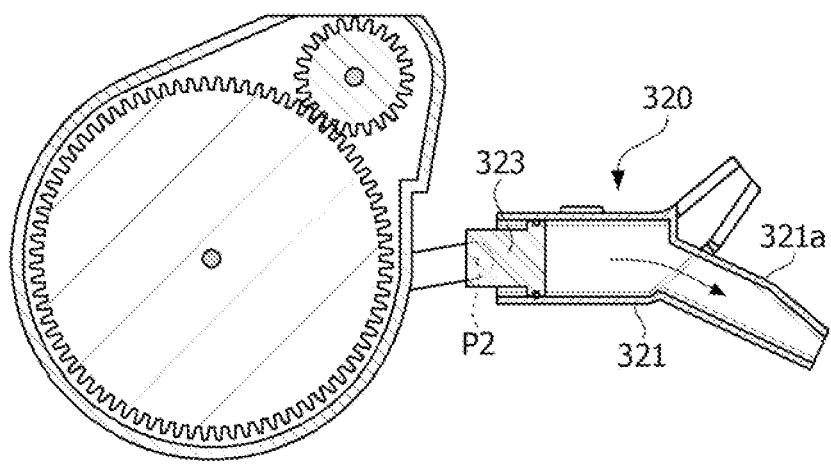

[FIG. 15]
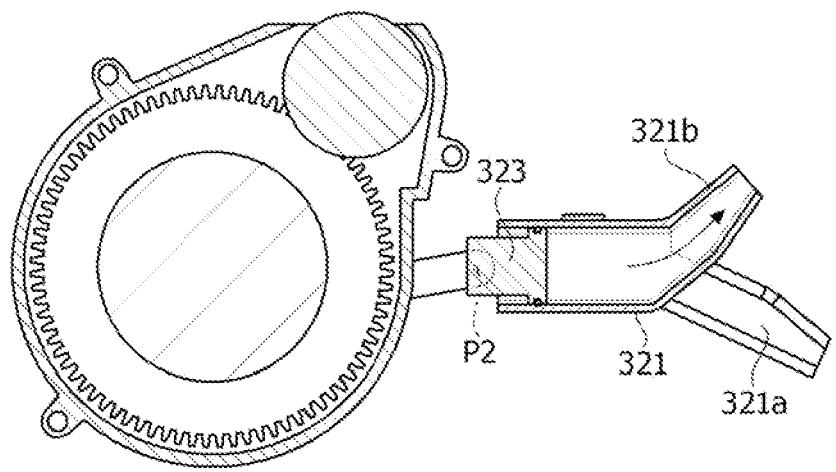
[FIG. 16]
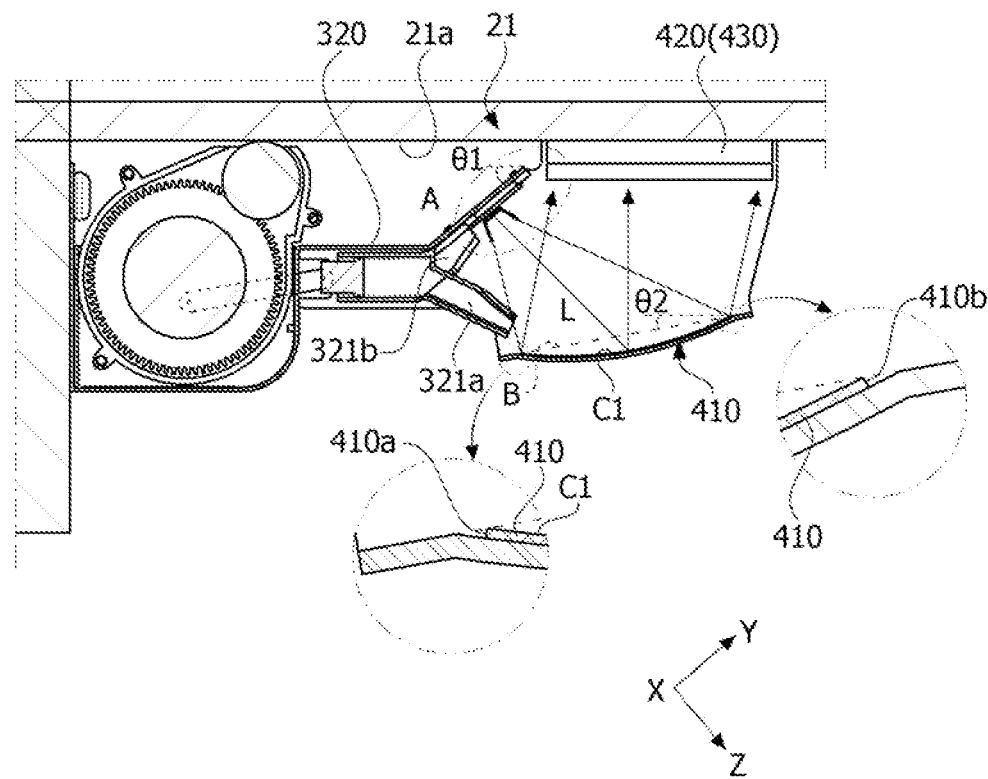

[FIG. 17]
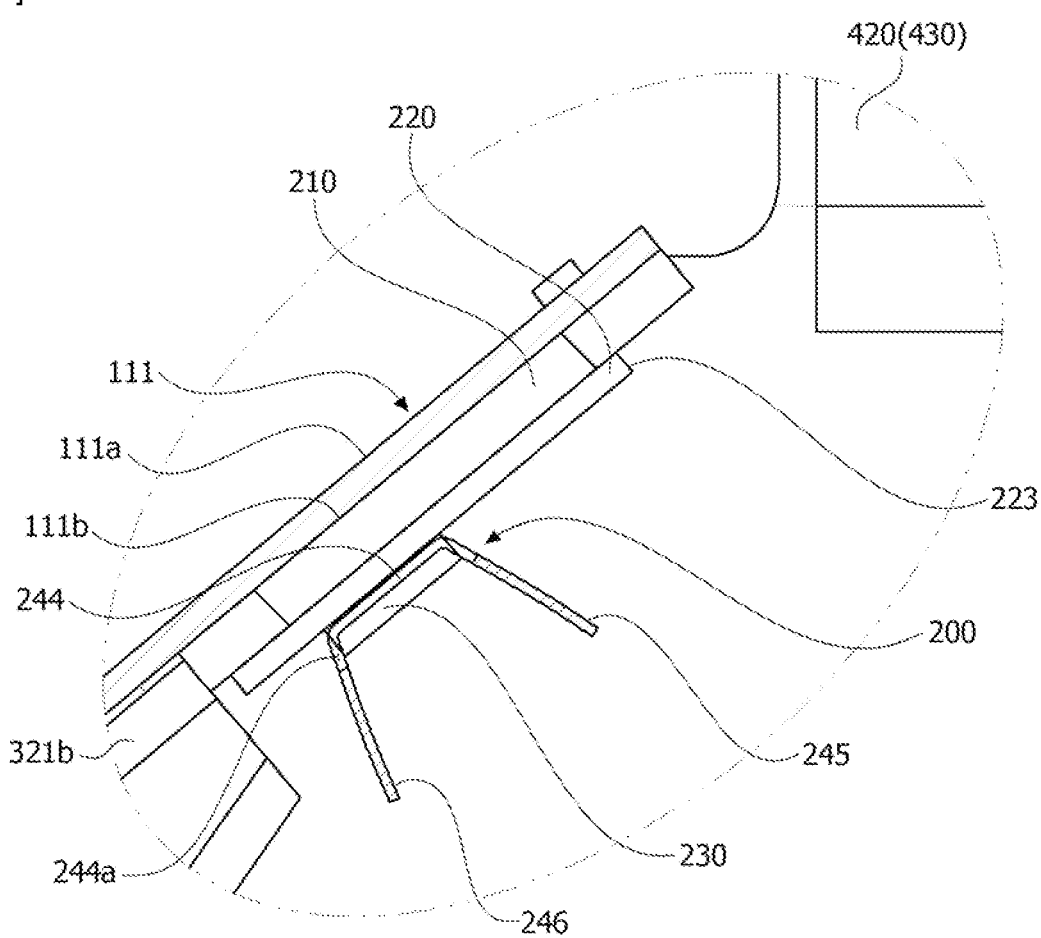

[FIG. 18]
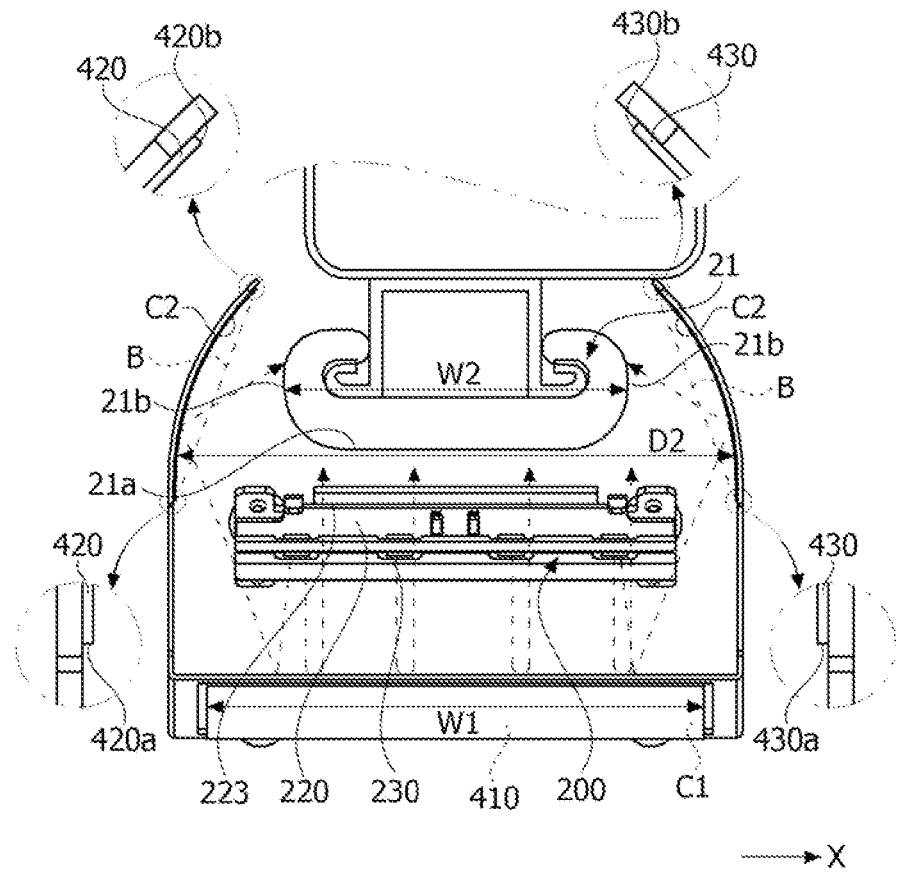
[FIG. 19]
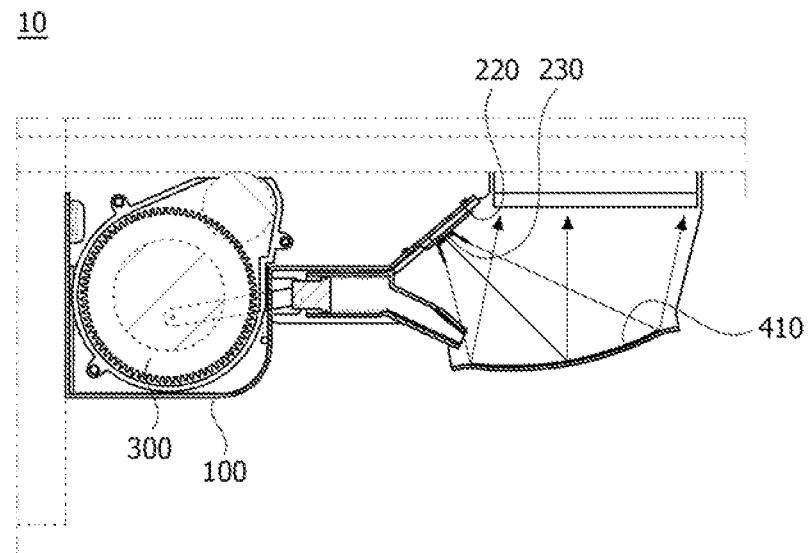

[FIG. 20]
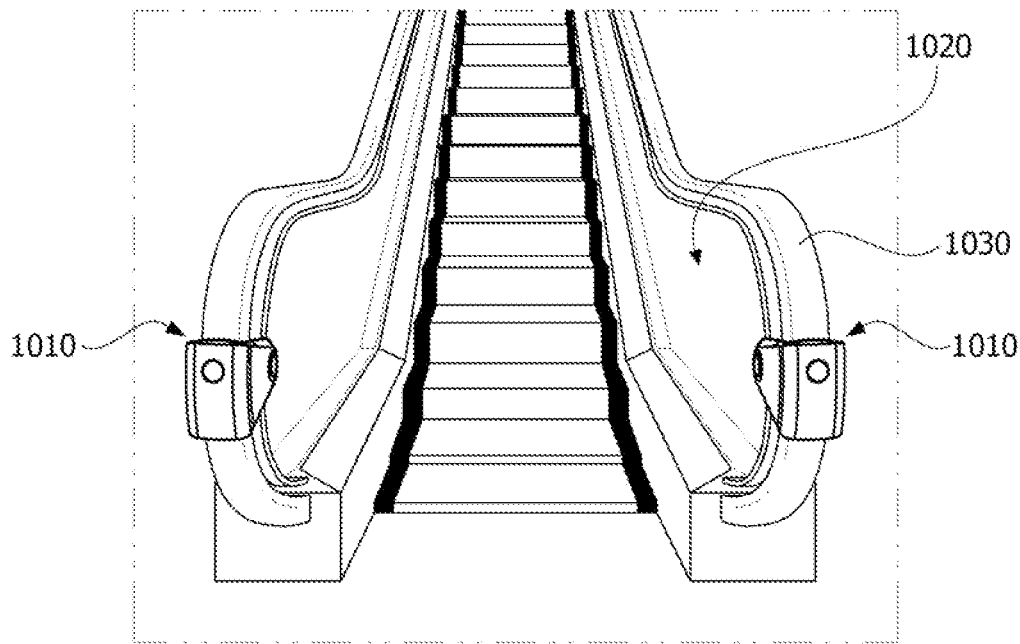
[FIG. 21]
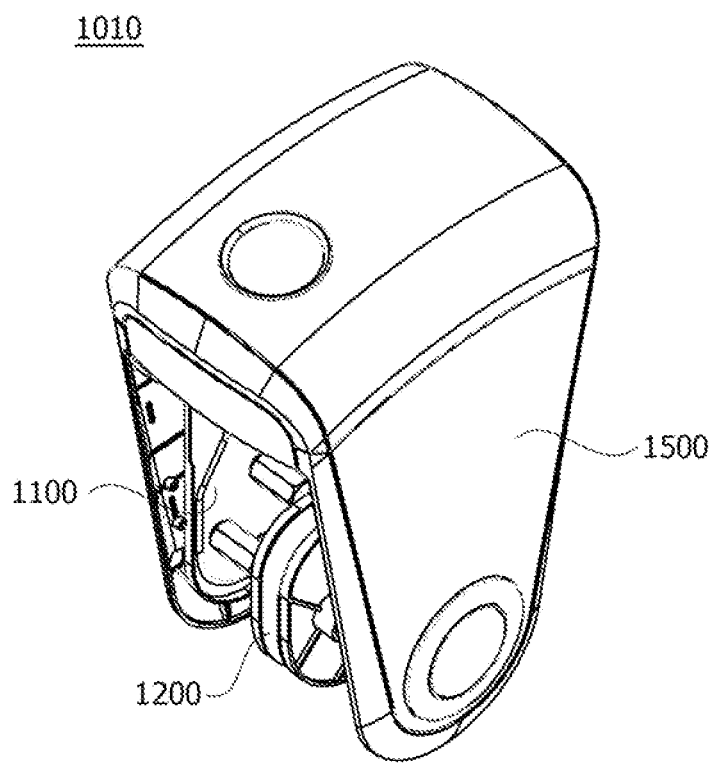

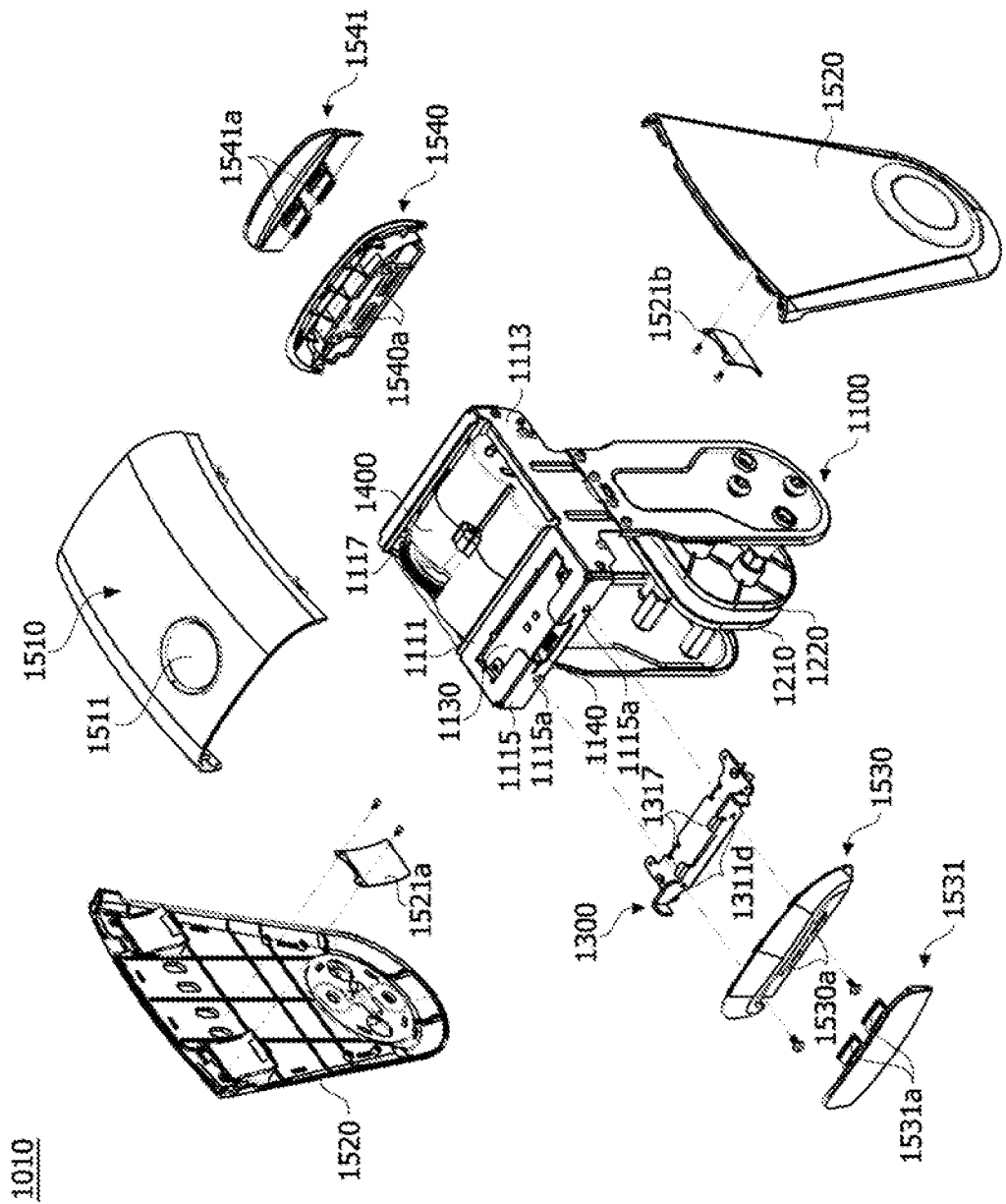
[FIG. 22]

[FIG. 23]
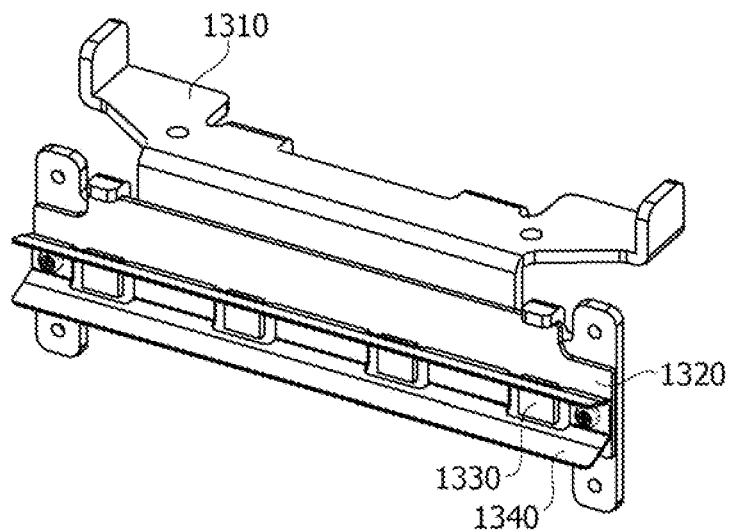
[FIG. 24]
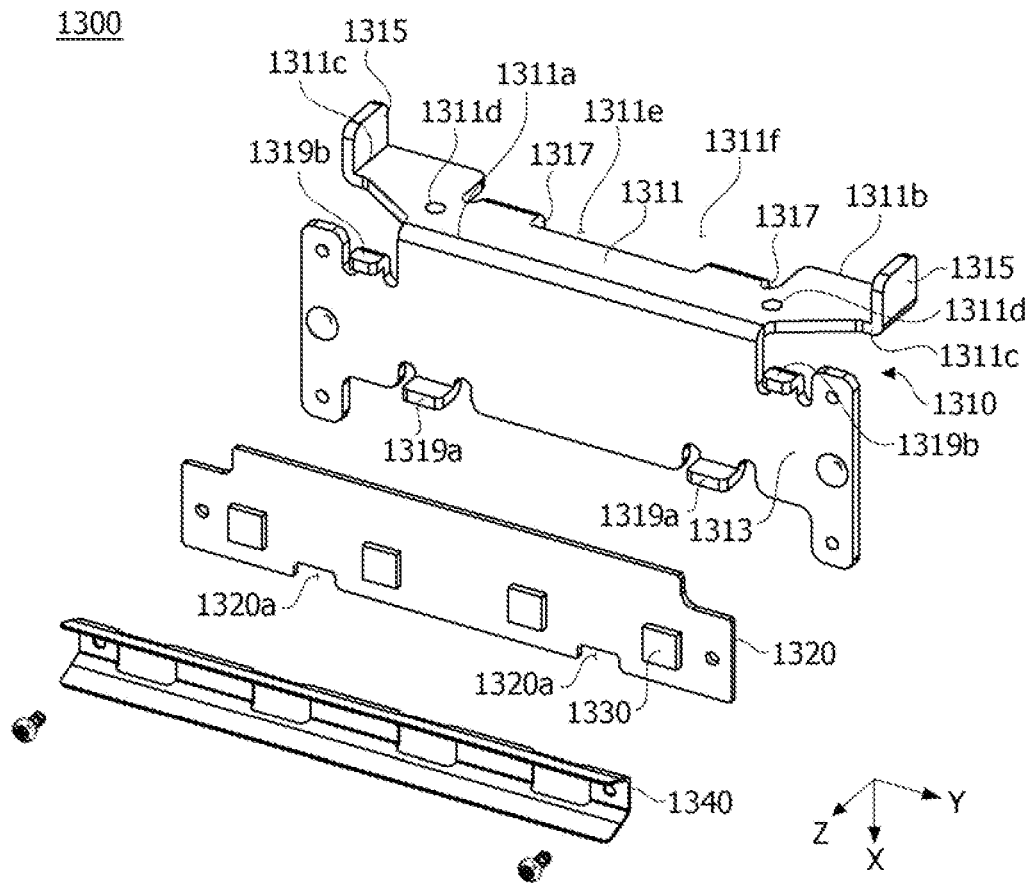

[FIG. 25]
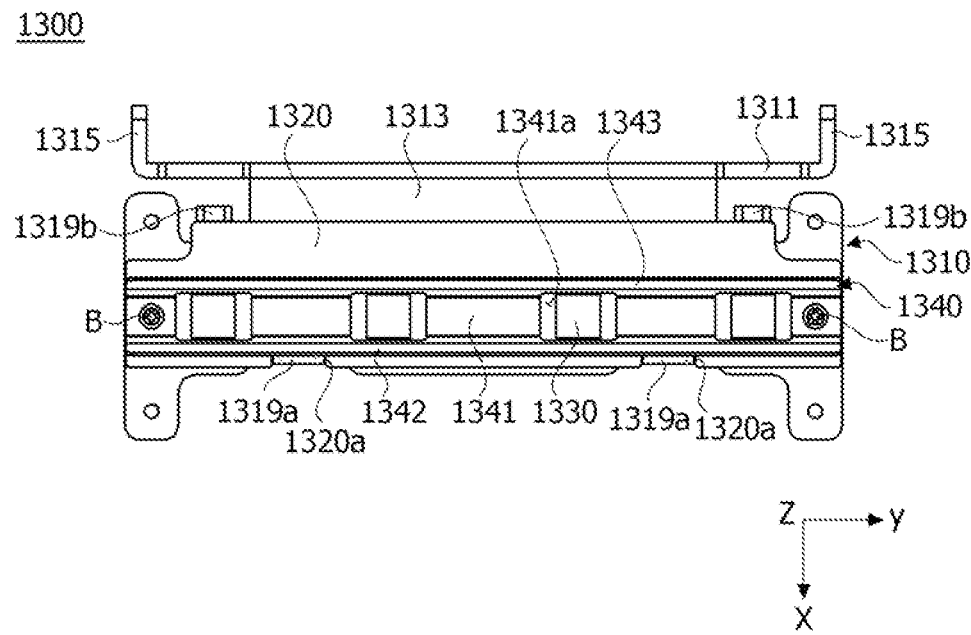
[FIG. 26]
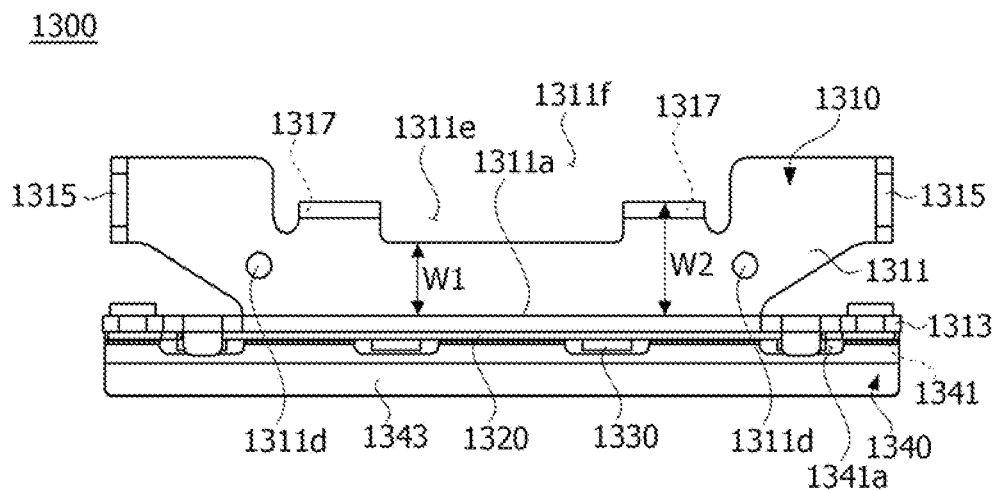

[FIG. 27]
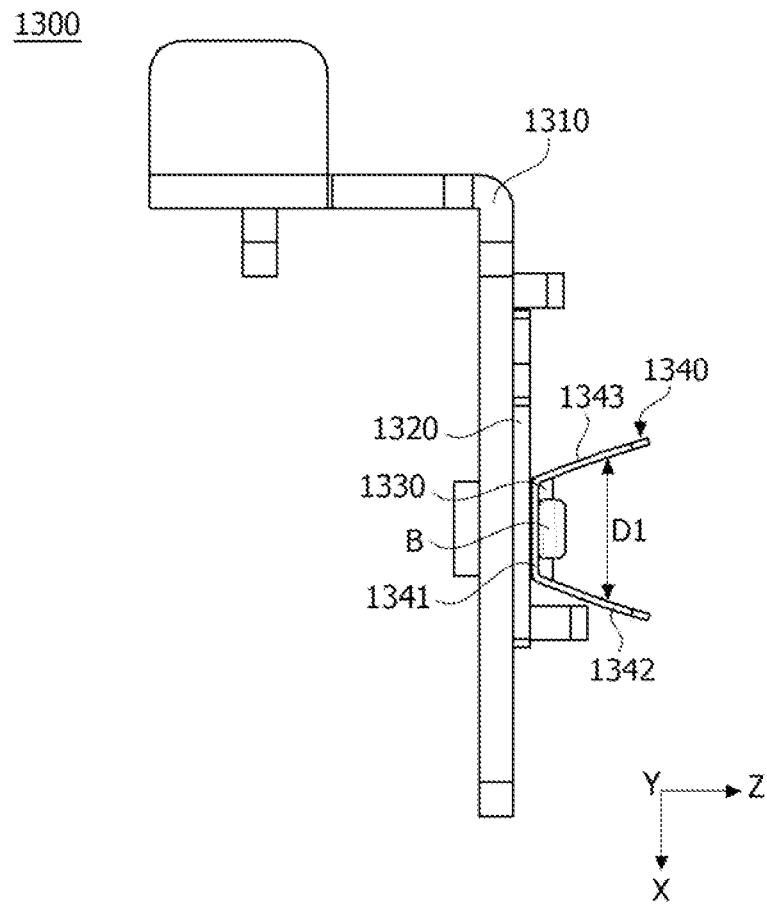
[FIG. 28]
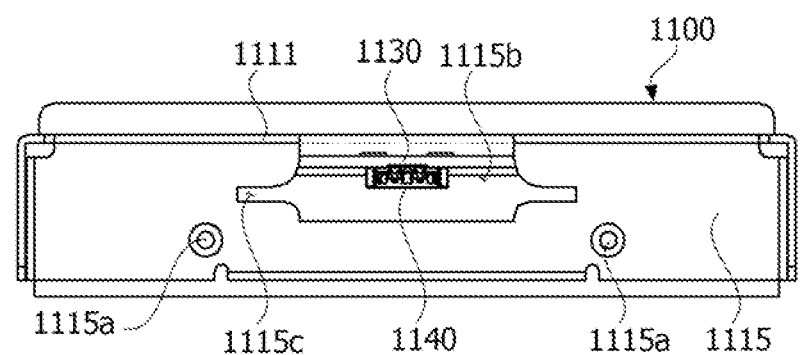

[FIG. 29]
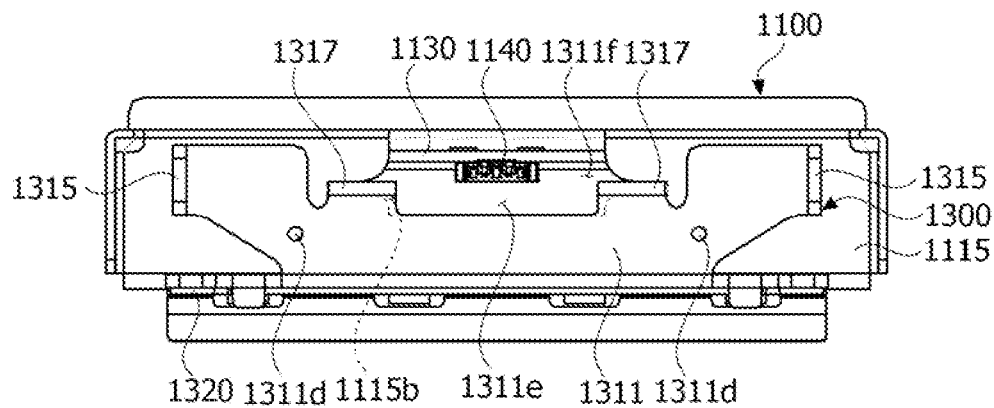
[FIG. 30]
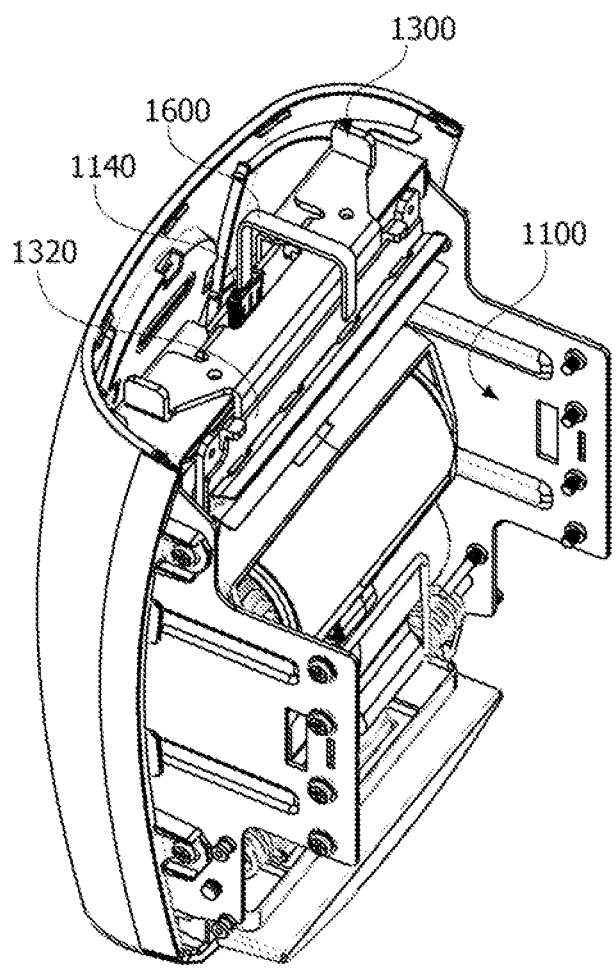

[FIG. 31]
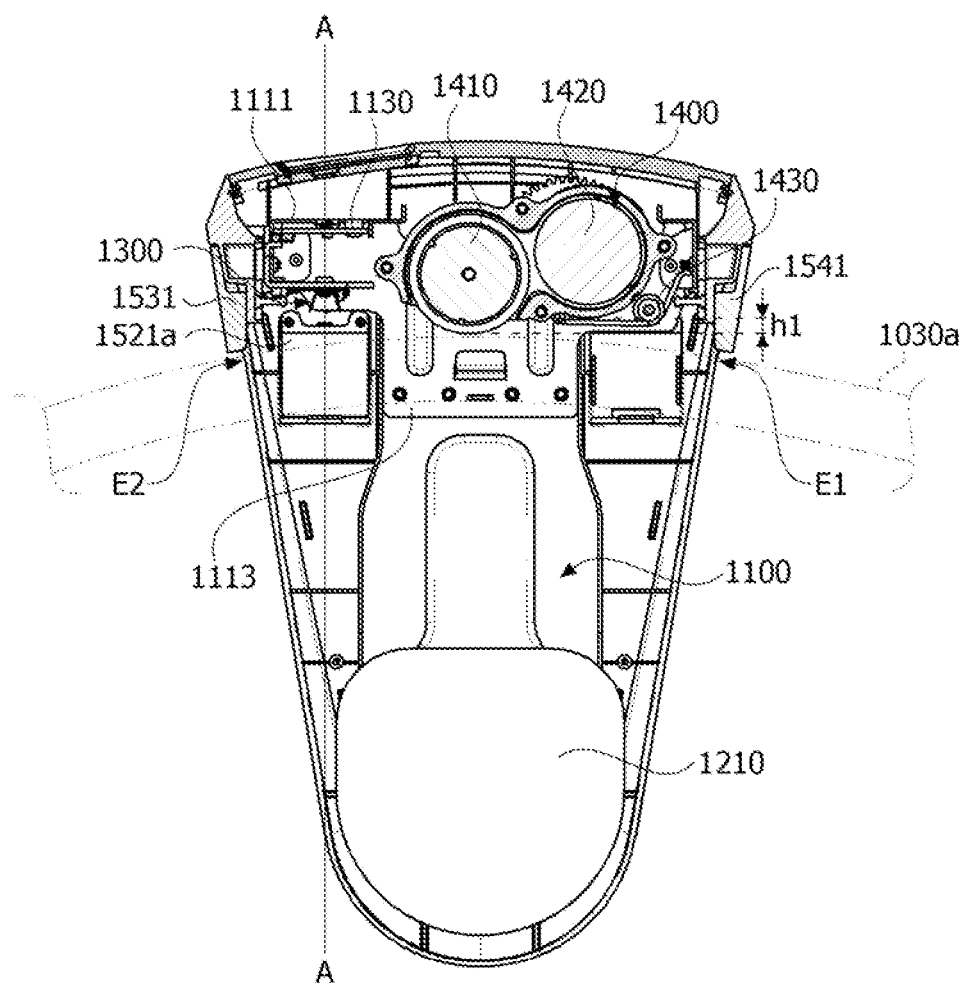

[FIG. 32]
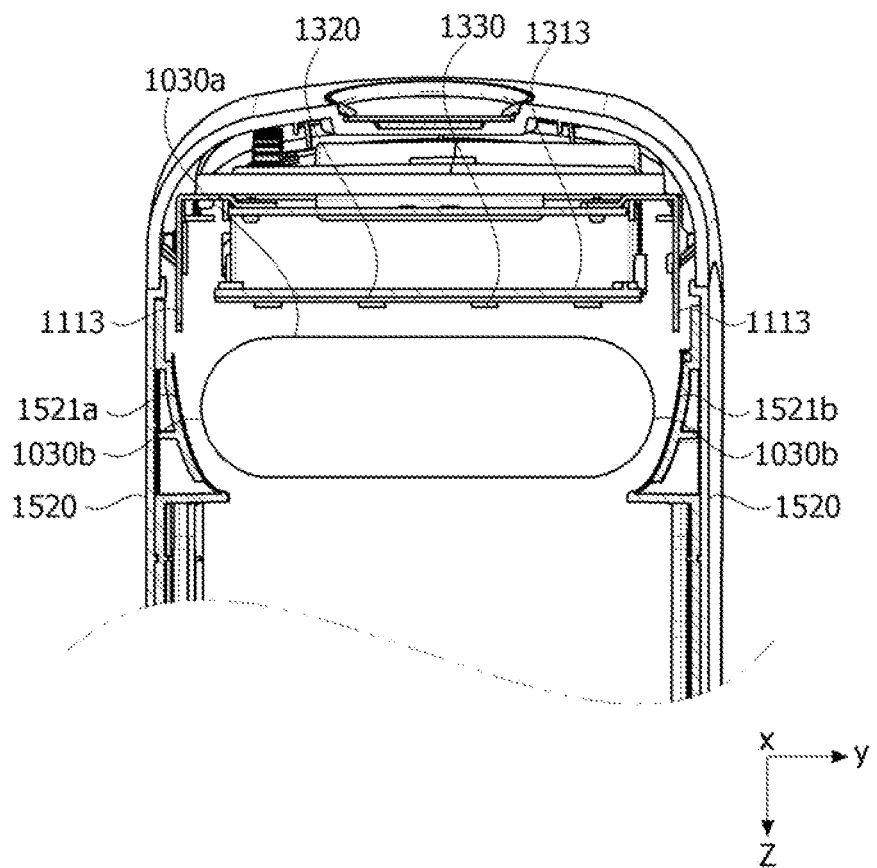

[FIG. 33]
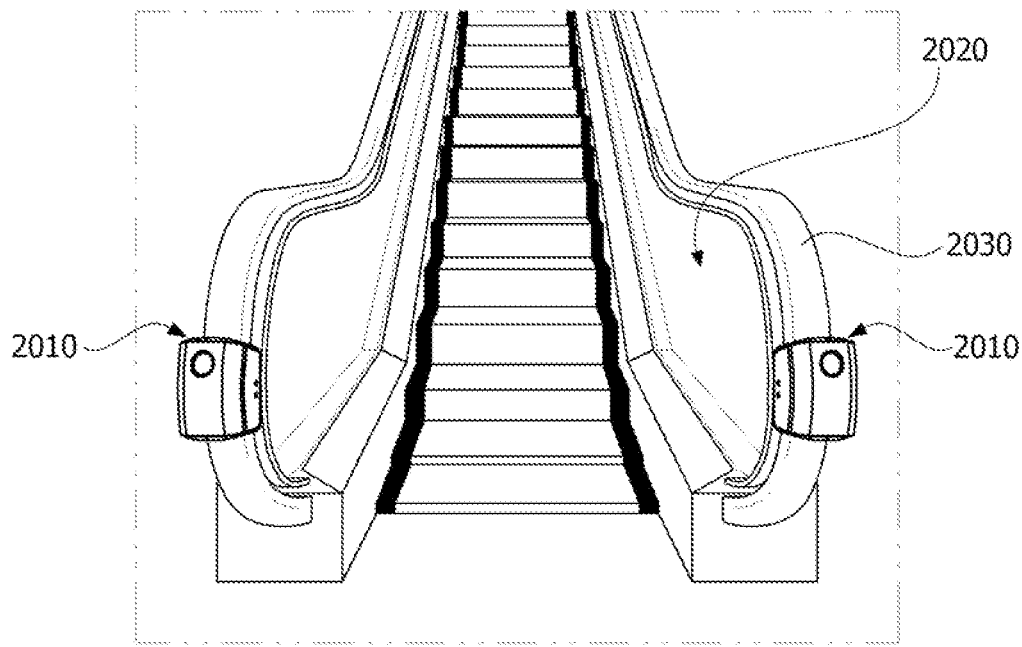
[FIG. 34]
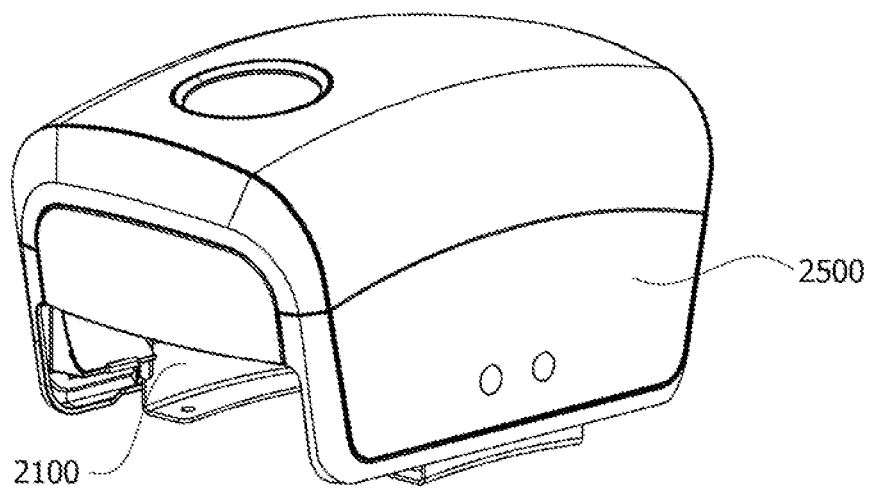

[FIG. 35]
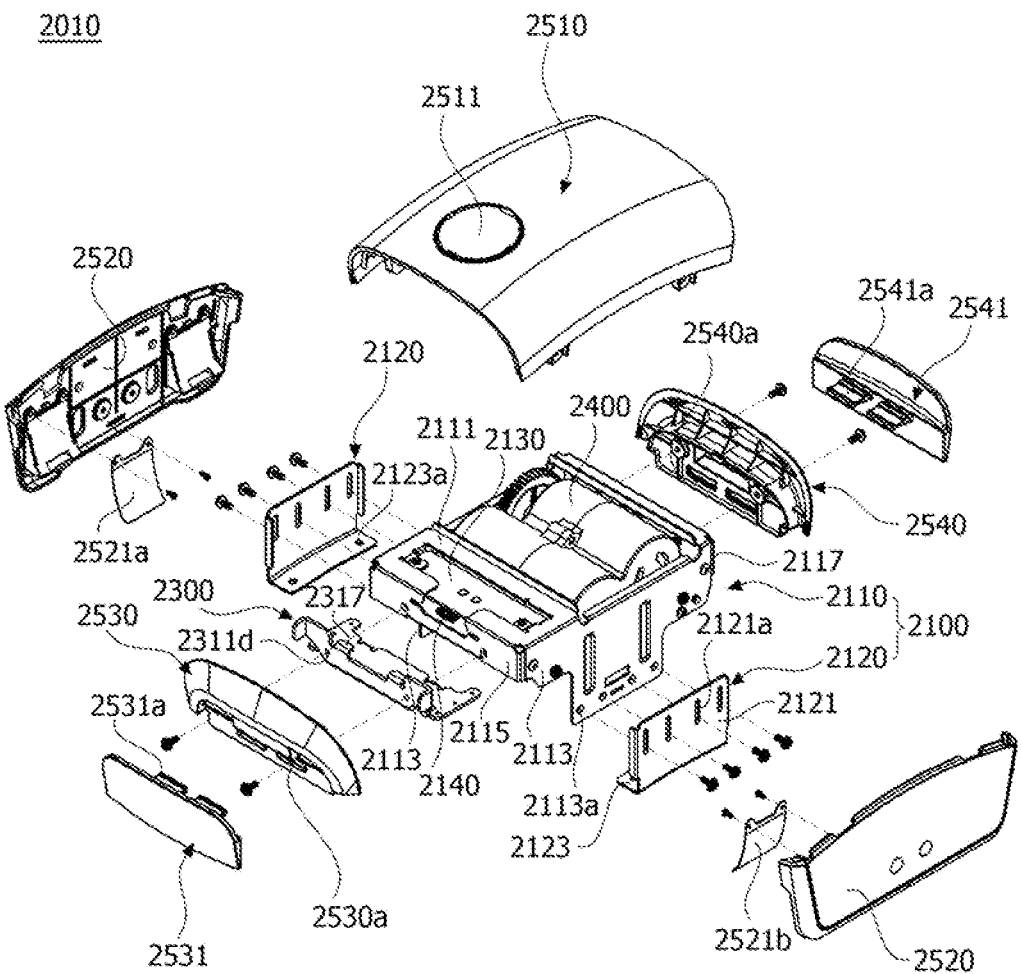

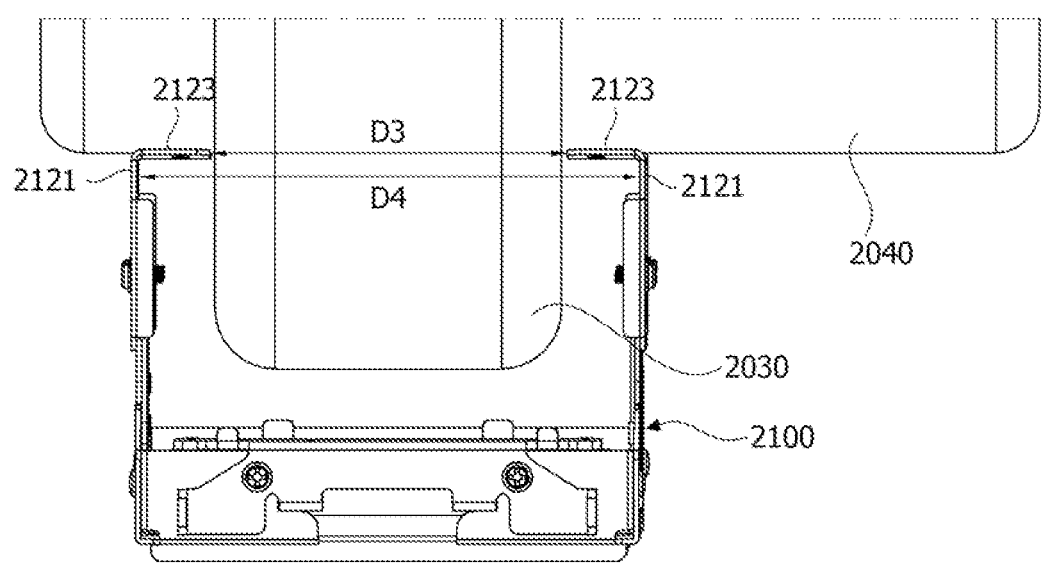
[FIG. 36]

[FIG. 37]
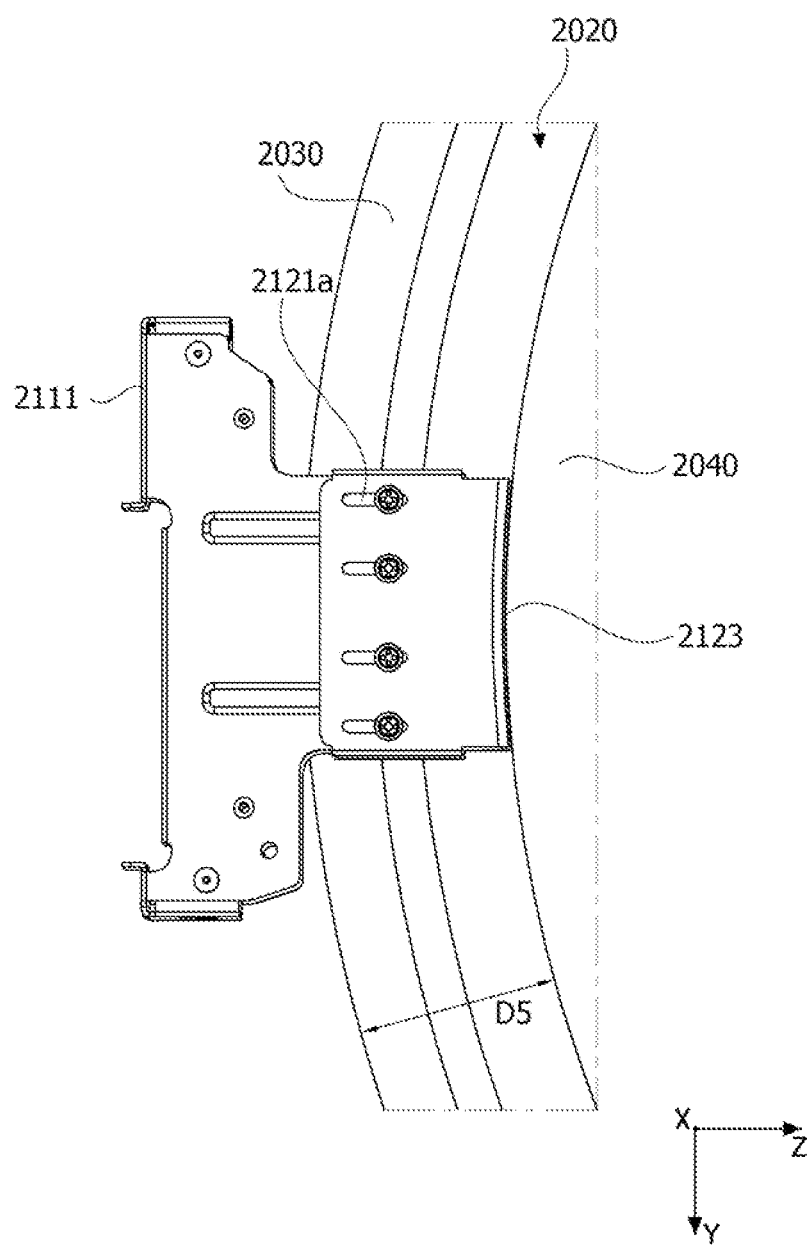

[FIG. 38]
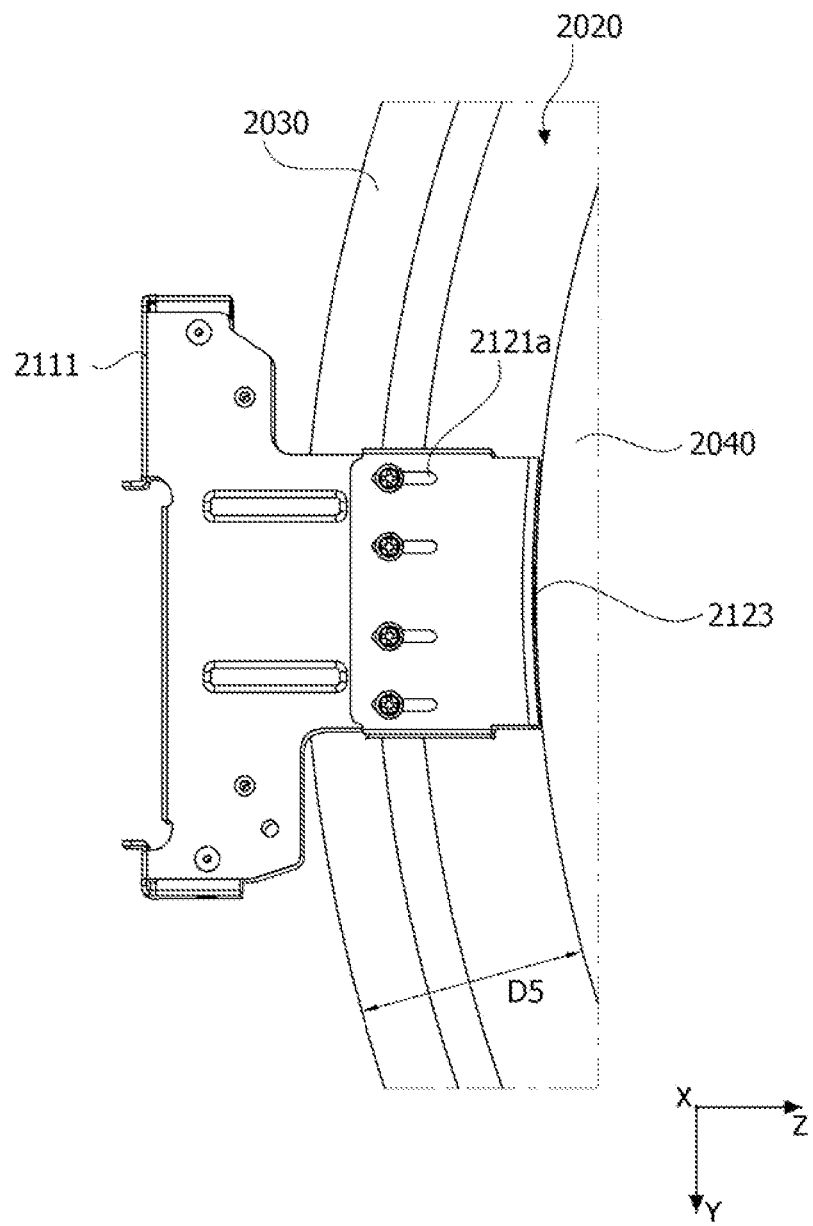

[FIG. 39]
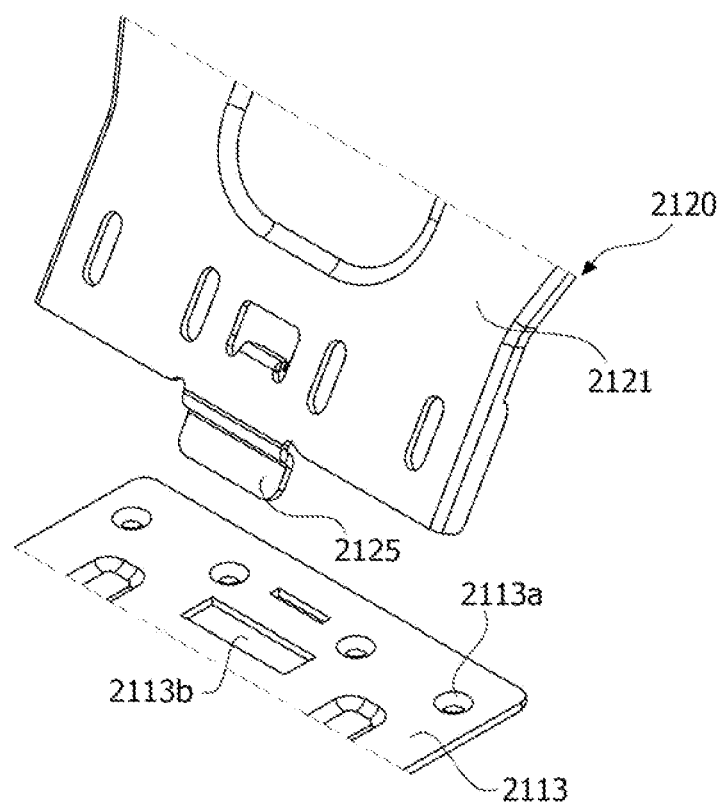

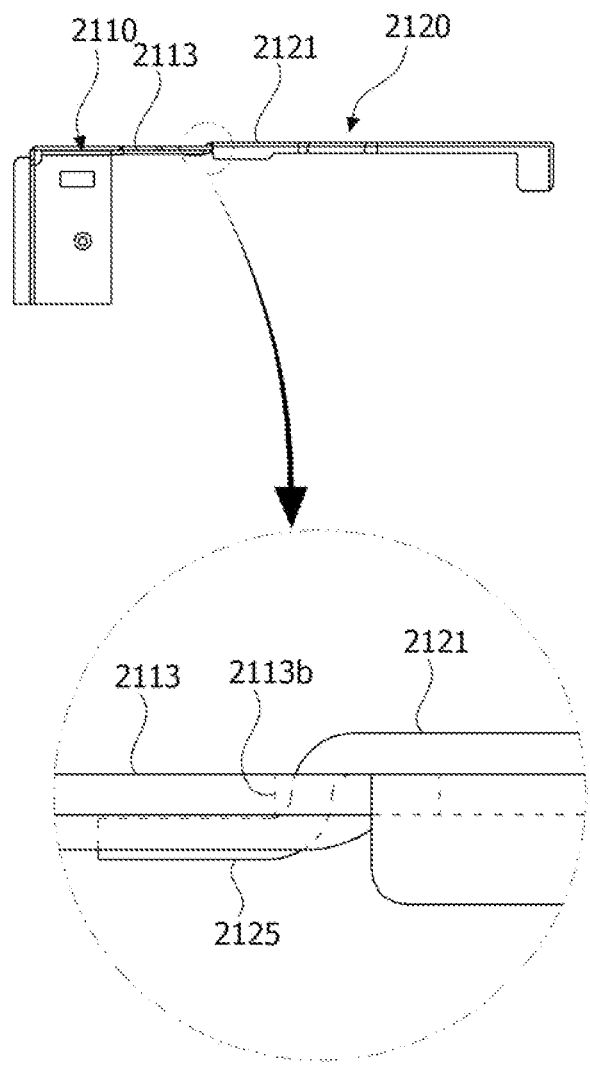
[FIG. 40]

[FIG. 41]
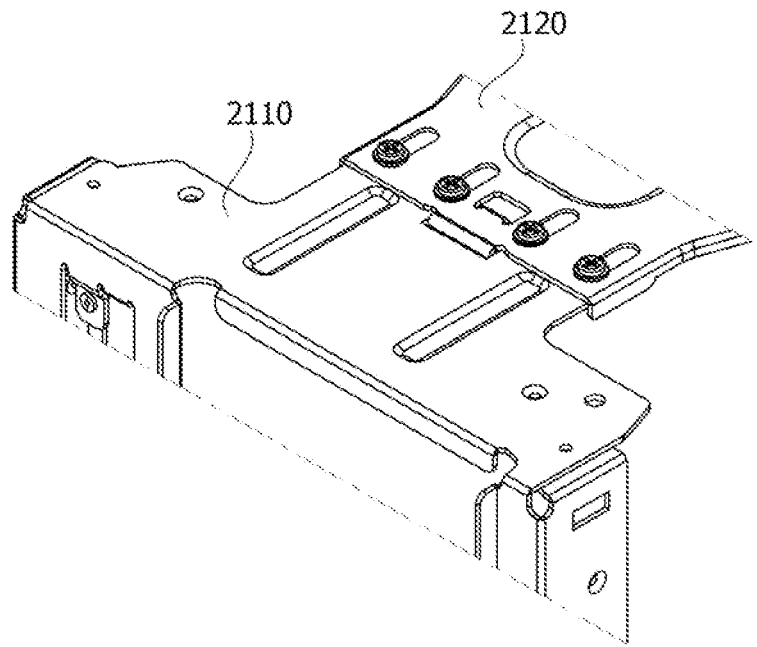
[FIG. 42]
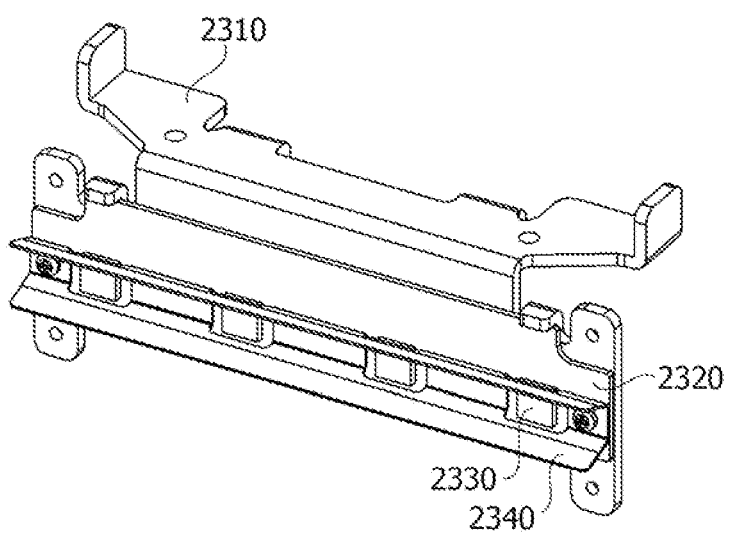

[FIG. 43]
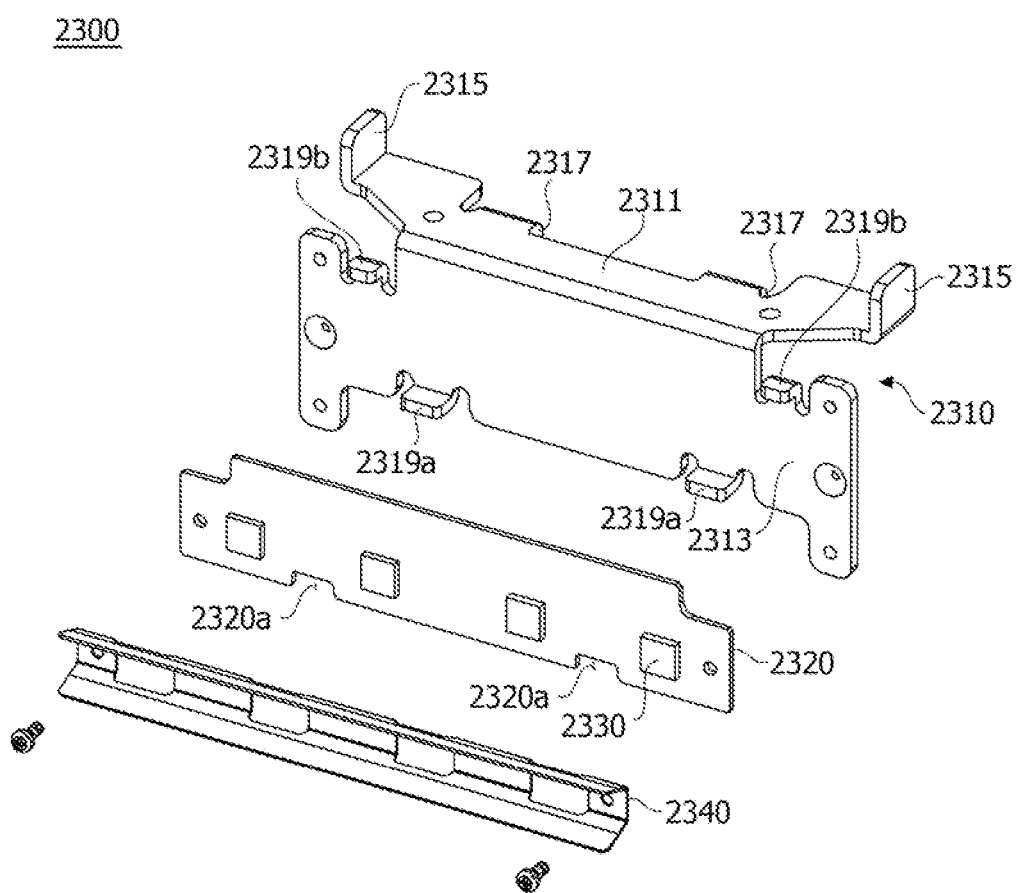

[FIG. 44]
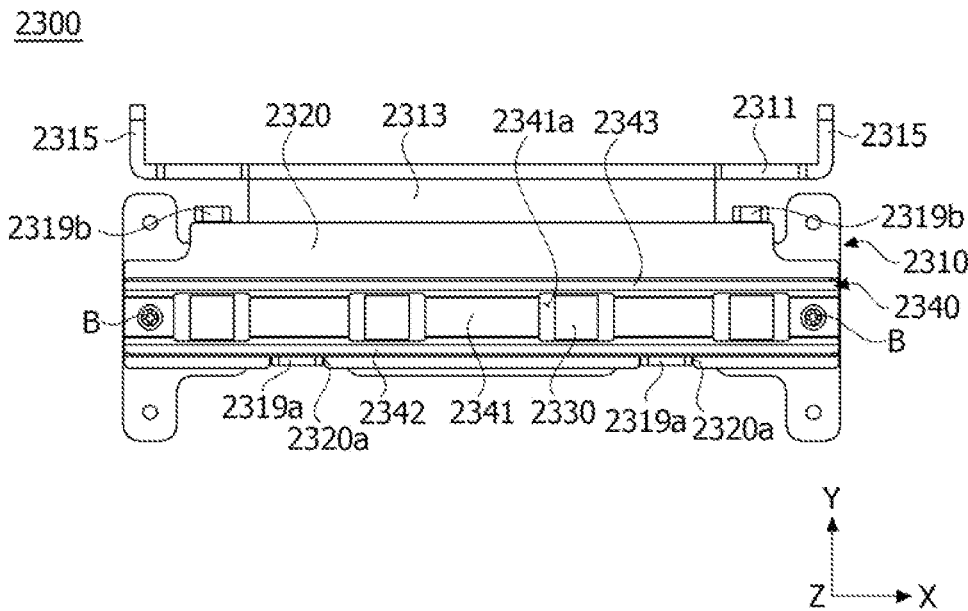
[FIG. 45]
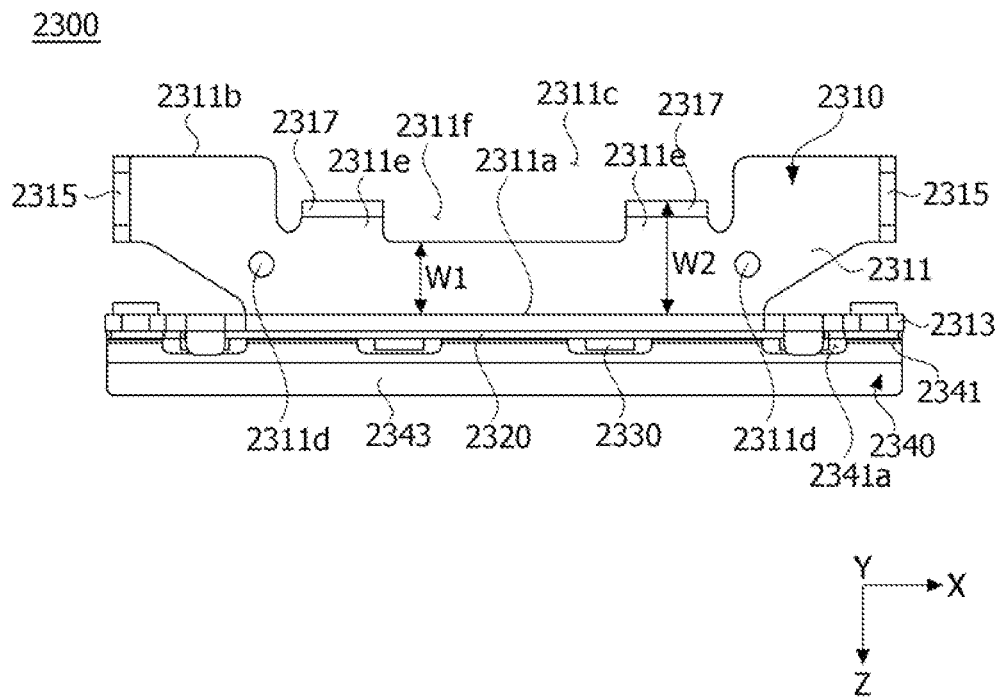

[FIG. 46]
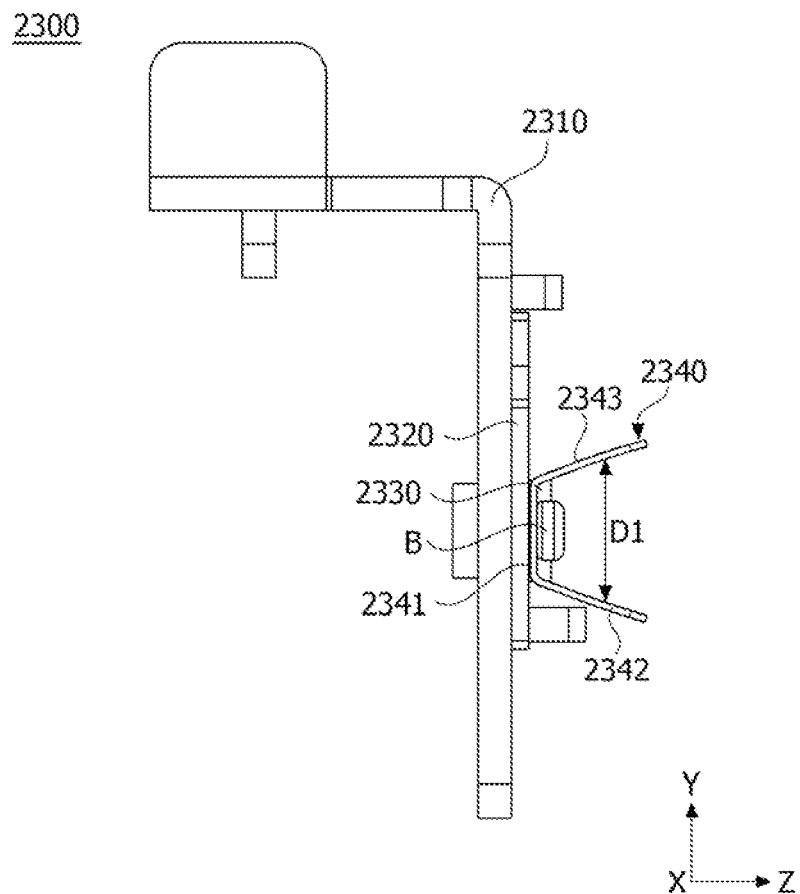
[FIG. 47]
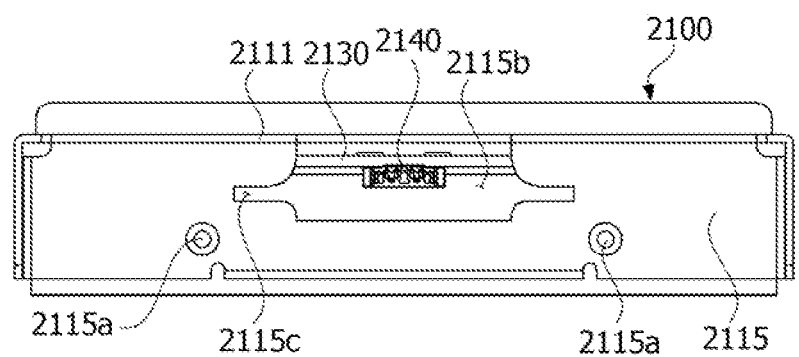

[FIG. 48]
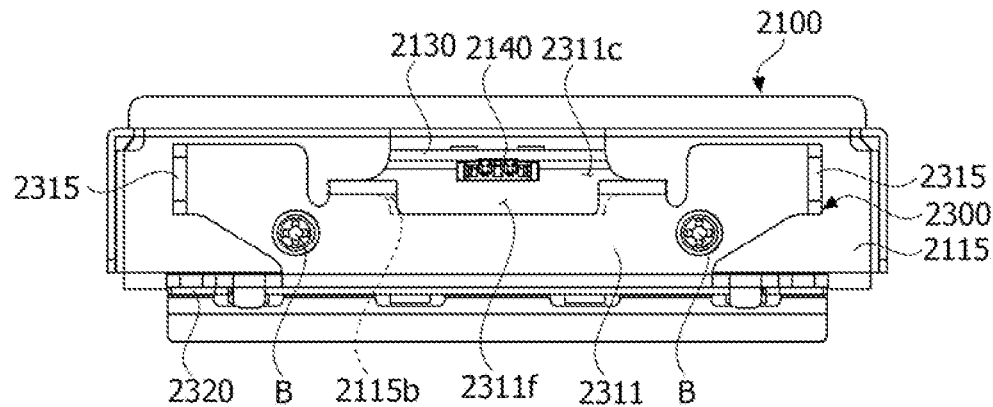
[FIG. 49]
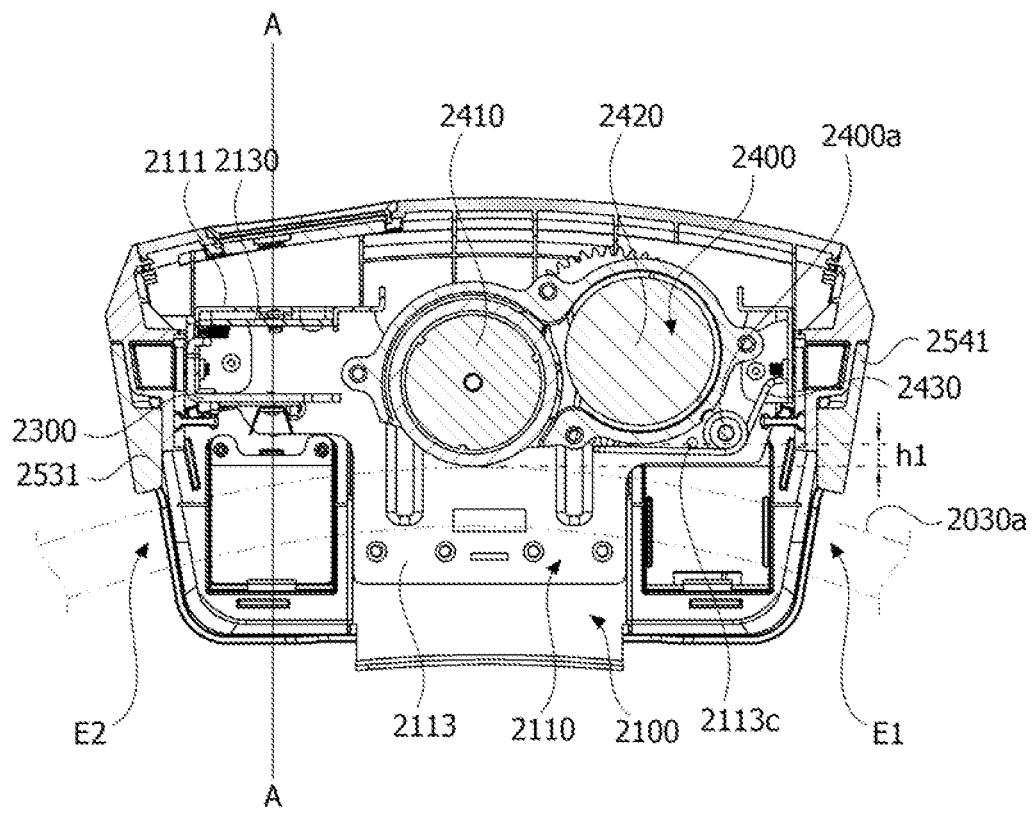

[FIG. 50]
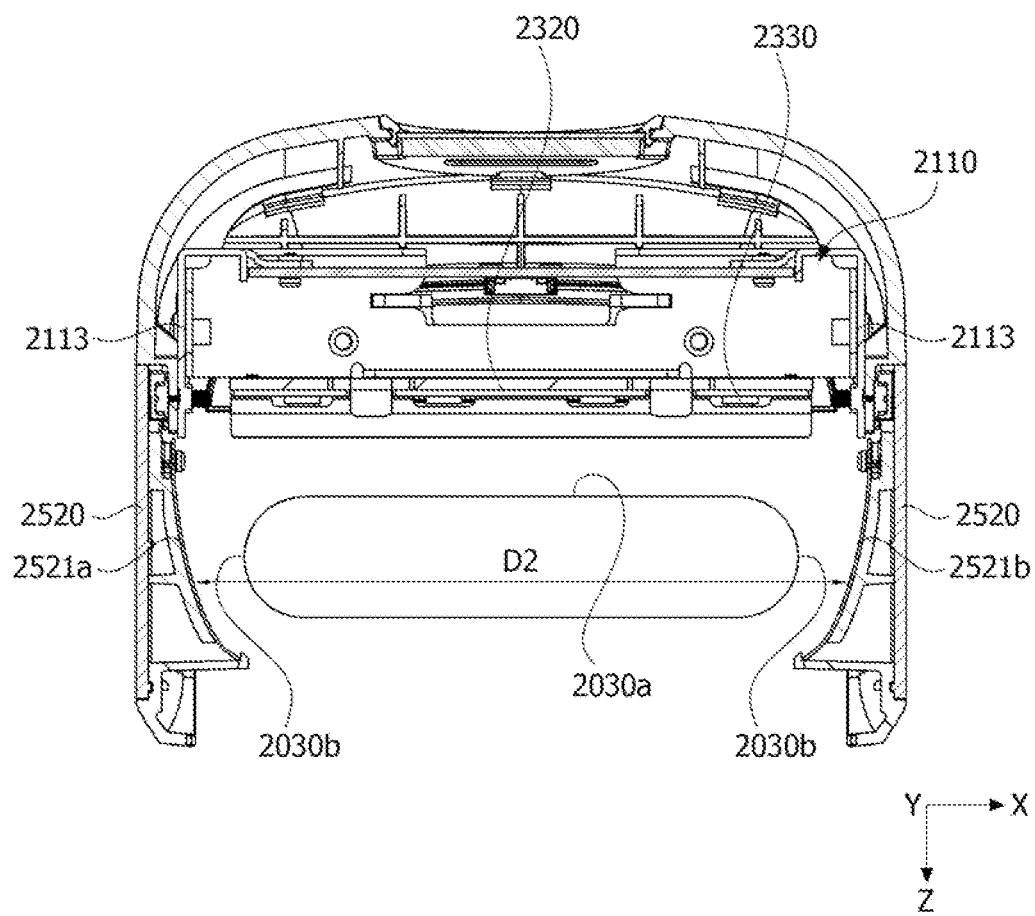

[FIG. 51]
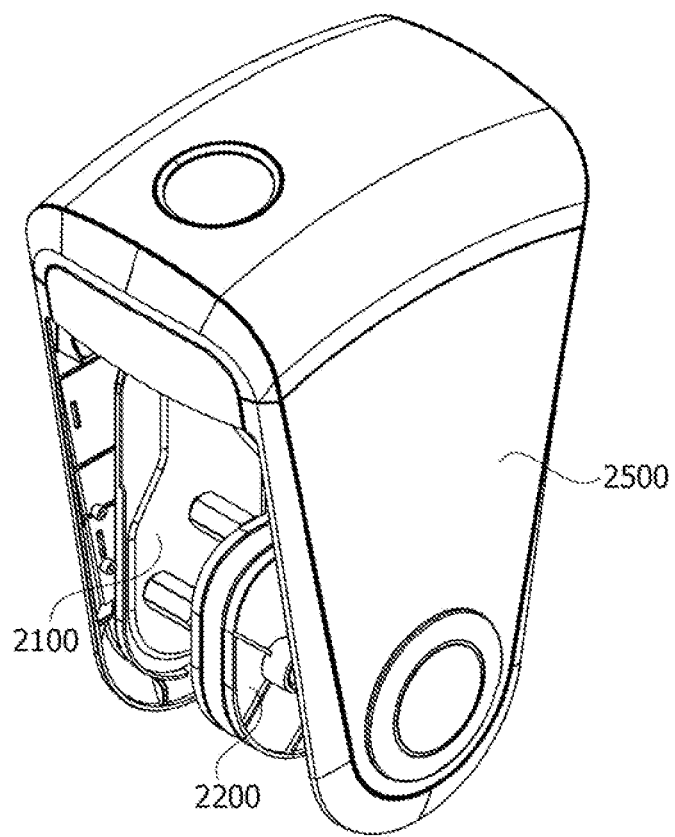

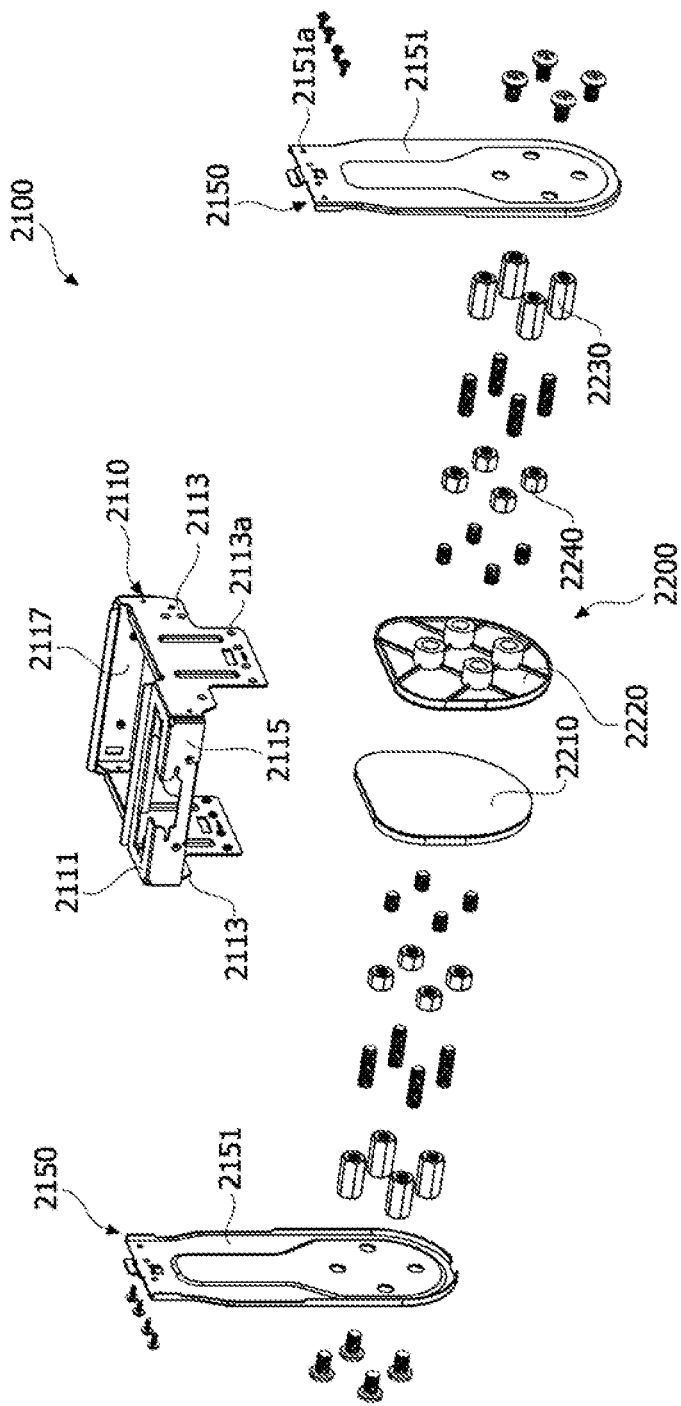

[FIG. 53]
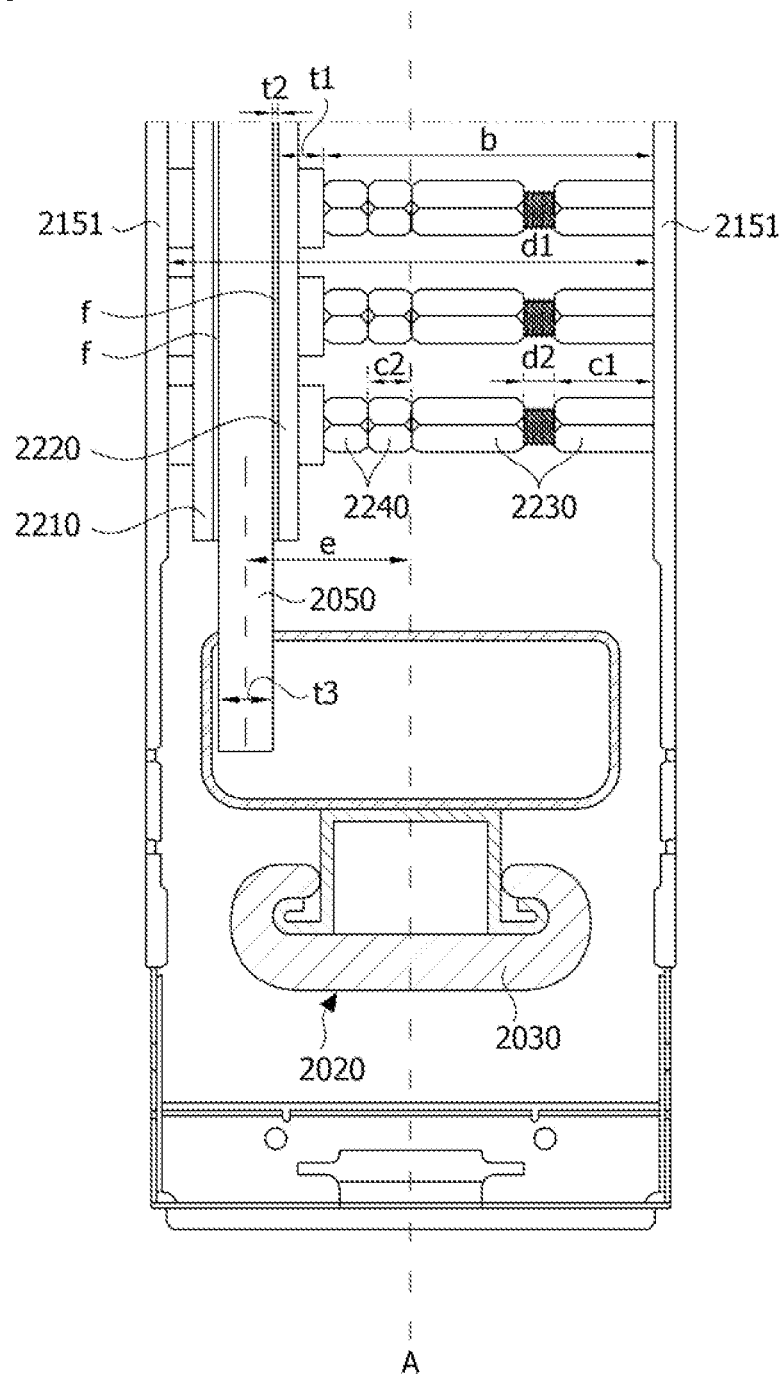

[FIG. 54]
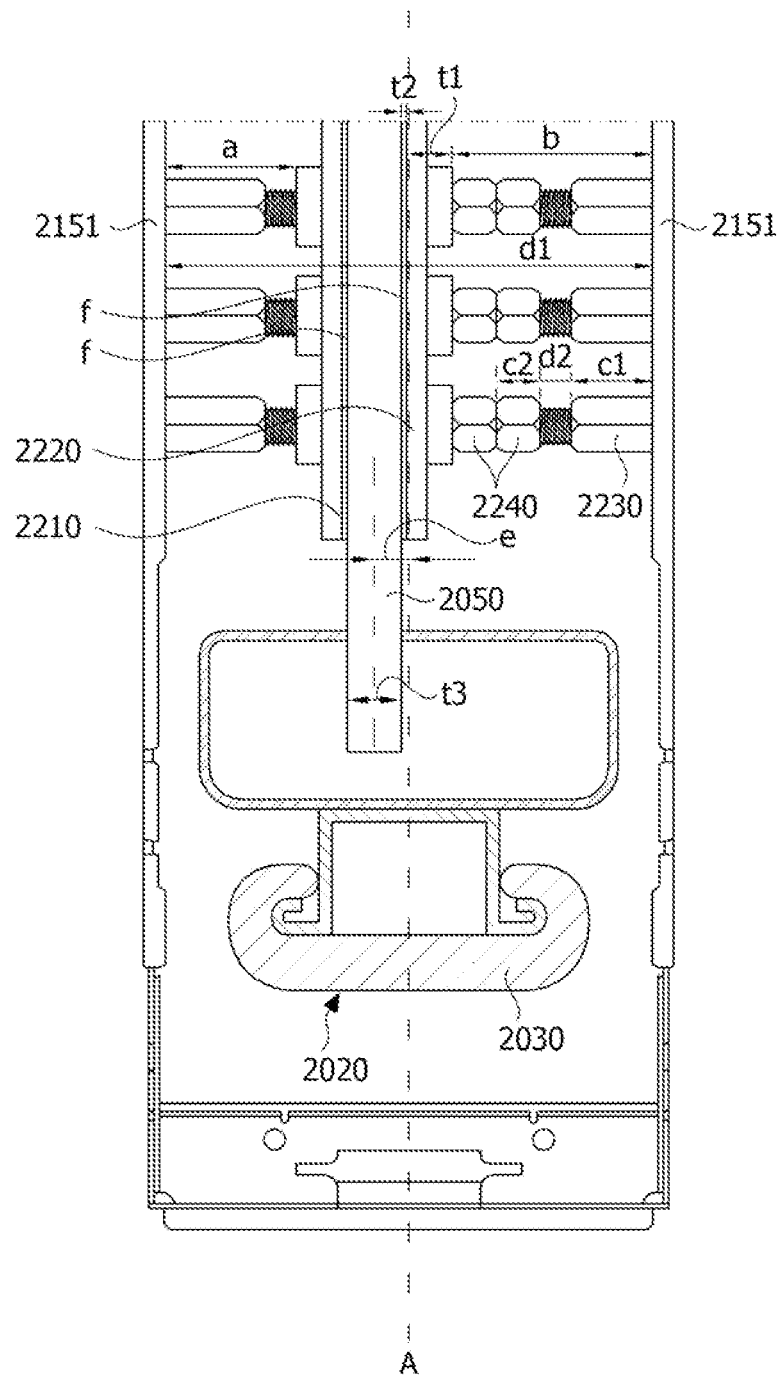

[FIG. 55]
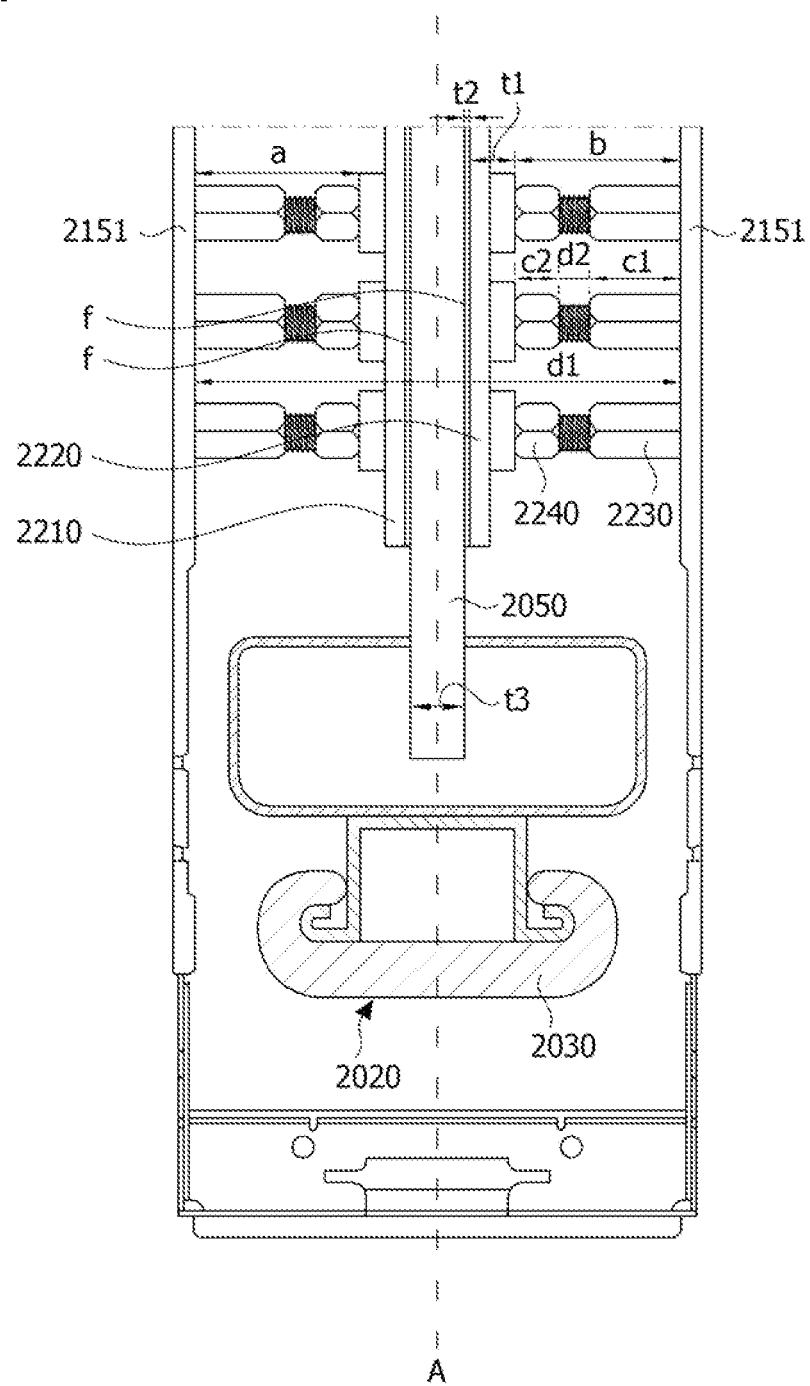

[FIG. 56]
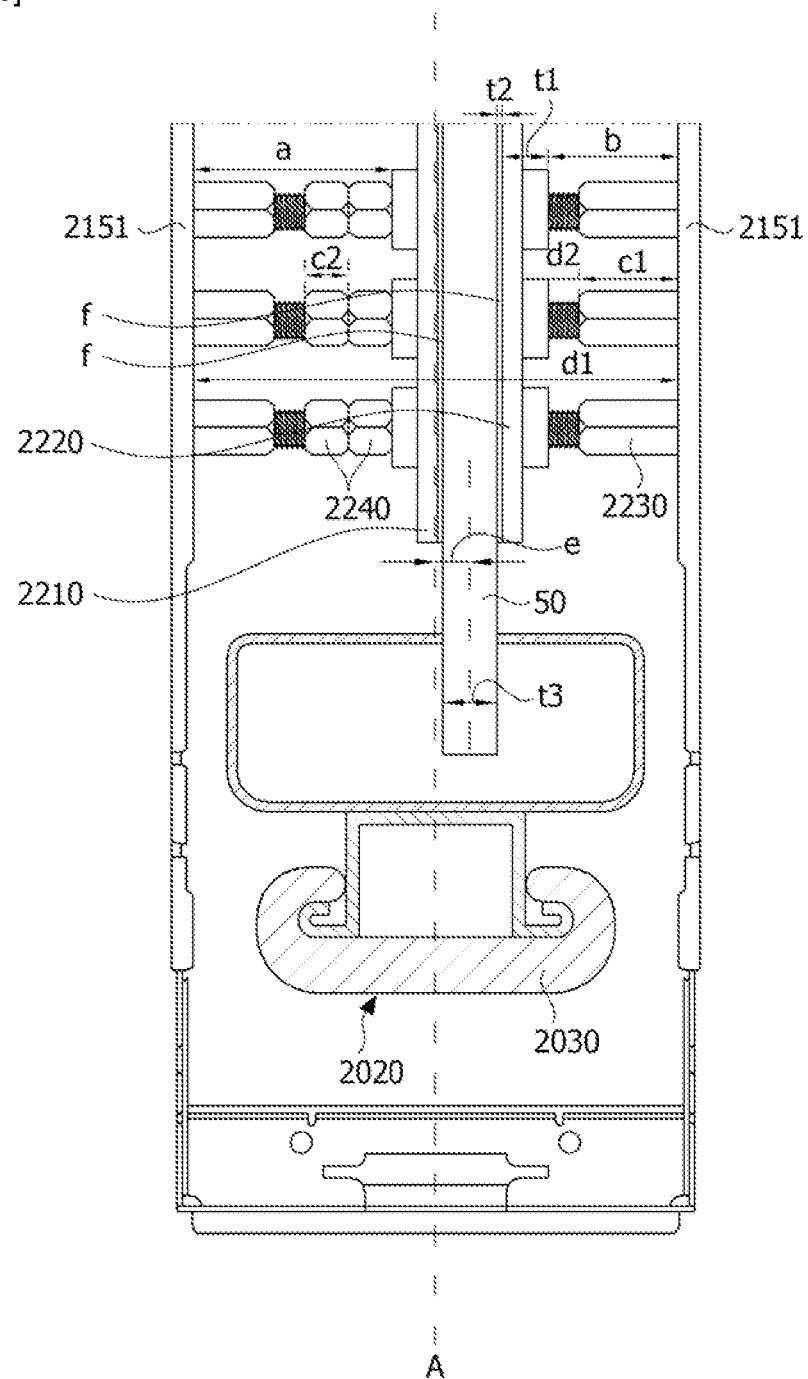

[FIG. 57]
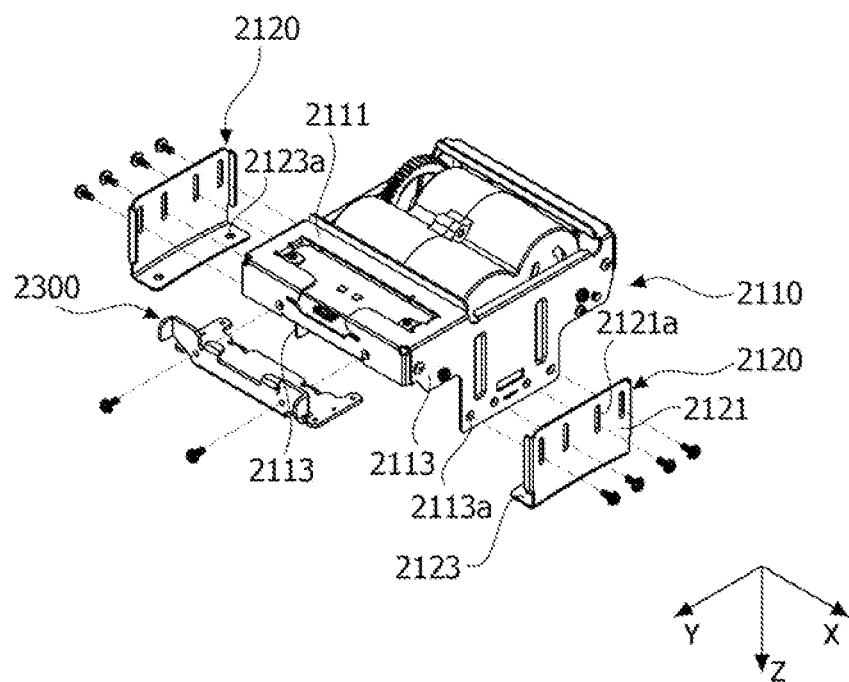

STERILIZATION MODULE, AND STERILIZATION APPARATUS AND ULTRAVIOLET IRRADIATION DEVICE COMPRISING SAME

CROSS REFERENCE TO RELATED APPLICATIONS

This application is the National Phase of PCT International Application No. PCT/KR2019/008266, filed on Jul. 5, 2019, which claims priority under 35 U.S.C. 119(a) to Korea Patent Application Nos. 10-2018-0080052, 10-2018-0080053, 10-2018-0080054, all filed on Jul. 10, 2018, and 10-2018-0088630, filed on Jul. 30, 2018, all of which are hereby expressly incorporated by reference into the present application.

TECHNICAL FIELD

The present invention relates to a sterilization module and a sterilization apparatus and an ultraviolet irradiation device including the same.

BACKGROUND ART

Escalators and moving walks have been installed at a variety of places such as a subway station, an airport, a department store, and the like where there is a large floating population and are conveniently used by a lot of people. However, handrails which are safety devices for escalators and moving walkways have a problem of being easily exposed to germs.

Recently, devices configured to sterilize handrails using ultraviolet light emitting devices have been developed. Ultraviolet light emitting devices may output light UV-A of a near-ultraviolet wavelength range, may output light UV-B of a far-ultraviolet wavelength range, and may output light UV-C of a deep-ultraviolet wavelength range. Among them, the light UV-C of the deep-ultraviolet wavelength range may have a sterilization function.

When an ultraviolet irradiation device emits light toward a handrail directly, the ultraviolet irradiation device may be contaminated by foreign substances falling from the handrail such that the intensity of irradiation may be decreased.

Also, since a user generally holds a handrail while moving, side surfaces of the handrail may be easily exposed to germs. Accordingly, it is necessary to sterilize side surfaces of the handrail.

Also, it is necessary to manufacture ultraviolet light emitting devices in a module form and detachably couple the light emitting devices to a sterilization device for periodical inspection, maintenance, and repair.

Also, there are a variety of escalators and moving walkways such as a glass type in which a glass plate is disposed inside a handrail rotating on an infinite orbit, a stainless steel (SUS) type in which a metallic support frame is disposed, and the like. Accordingly, it is necessary to design a product compatible with a variety of types of escalators and moving walkways.

DISCLOSURE

Technical Problem

Embodiments provide a sterilization module easily attachable to or detachable from a sterilization device.

Embodiments provide a sterilization device of which a problem of degradation in sterilization power caused by contamination of an optical system such as a light source, a reflector, or the like with foreign substances is solved.

Embodiments provide a sterilization device capable of sterilizing even side surfaces of a handrail.

Embodiments provide an ultraviolet irradiation device compatible with a variety of types of escalators and moving walkways.

Embodiments provide an ultraviolet irradiation device to or from which a light source module is attachable or detachable.

Embodiments provide an ultraviolet irradiation device configured to sterilize even side surfaces of a handrail.

Aspects of the present invention are not limited thereto and include objectives and effects which are recognizable from the following aspects or embodiments.

Technical Solution

A 1-1st aspect of the present invention provides a sterilization device including a frame; a circuit board disposed on the frame; an ultraviolet light emitting device disposed on the circuit board; and a first reflector, a second reflector, and a third reflector which are disposed on the frame. Here, the circuit board includes one end portion and another end portion which face each other with a length in a first direction and a pair of side end portions which are parallel in a second direction with the one end portion therebetween. The first reflector is disposed on the one end portion side of the circuit board. The second reflector and the third reflector are disposed on the other end portion side of the circuit board. The second reflector and the third reflector face each other in the first direction. The first reflector is overlapped with the circuit board in a third direction perpendicular to the first direction and the second direction. The second reflector and the third reflector are disposed to face the first reflector. The second reflector and the third reflector are disposed to be spaced apart from the other end portion in the second direction.

The first reflector may be tilted with respect to the second direction.

The second reflector and the third reflector may be tilted with respect to the first direction.

A distance between the second reflector and the third reflector may be gradually reduced in a direction away from the first reflector.

A maximum distance between the second reflector and the third reflector may be greater than a length of the other end portion in the first direction.

The second reflector and the third reflector may not be overlapped with the circuit board in the third direction.

The first reflector may include a first end portion and a second end portion facing the first end portion and disposed to be farther from the circuit board than the first end portion, may have a curvature from the first end portion to the second end portion, and may be concave toward the ultraviolet light emitting device.

The second reflector and the third reflector may each include a third end portion and a fourth end portion facing the third end portion and disposed to be farther from the first reflector than the third end portion, may have a curvature from the third end portion to the fourth end portion, and may be concave to each other.

The sterilization device may include a reflection member disposed on the circuit board.

The reflection member may include a fourth reflector disposed on the circuit board, and the fourth reflector may include a through hole in which the ultraviolet light emitting device is disposed.

The reflection member may include a fifth reflector and a sixth reflector which are bent from both ends of the fourth reflector in the second direction and face each other.

A 1-2nd aspect of the present invention provides a sterilization device including a frame; a circuit board disposed on the frame and including one end portion, another end portion, and a pair of side end portions facing each other with the one end portion therebetween; an ultraviolet light emitting device disposed on the circuit board; and a first reflector, a second reflector, and a third reflector which are disposed on the frame. Here, the first reflector is disposed on the one end portion side, and the second reflector and the third reflector are disposed on the other end portion side. The second reflector and the third reflector face each other with a moving structure therebetween in a first direction parallel to the one end portion. The first reflector is overlapped with the circuit board in a third direction perpendicular to the first direction and a second direction parallel to the side end portions. The first reflector is disposed to face the second reflector, the third reflector, and the moving structure. The second reflector and the third reflector are disposed to face the moving structure. The second reflector and the third reflector are disposed to be spaced apart from the other end portion in the second direction.

The circuit board may be tilted at a first acute angle with respect to the moving structure. The first reflector may include a first reflecting surface disposed to face the moving structure, and the first reflecting surface may be tilted at a second acute angle smaller than the first acute angle with respect to the moving structure.

The first reflector may include a first end portion and a second end portion facing the first end portion and disposed to be farther from the circuit board than the second end portion, may have a curvature from the first end portion to the second end portion, and may be concave toward the moving structure.

The second reflector and the third reflector may include a second reflecting surface and a third reflecting surface which are disposed to face the moving structure, respectively. A distance between the second reflecting surface and the third reflecting surface may be gradually reduced in a direction away from the first reflector.

A 2-1st aspect of the present invention provides a sterilization device including a frame; a circuit board disposed on the frame; an ultraviolet light emitting device disposed on the circuit board; a first reflector disposed on the frame; and an air ejection module disposed on the frame. Here, the first reflector is disposed to face the ultraviolet light emitting device. The air ejection module includes a roller assembly and a pump assembly. The pump assembly includes a cylinder; a piston disposed in the cylinder; and a first nozzle opened toward the first reflector. The air ejection module includes a power transmission member configured to connect the roller assembly to the piston.

The sterilization device may include a second reflector and a third reflector which are disposed on the frame. Here, the circuit board includes one end portion and another end portion which face each other with a length in a first direction and a pair of side end portions which are parallel in a second direction with the one end portion therebetween. The first reflector is disposed on the one end portion side of the circuit board. The second reflector and the third reflector are disposed on the other end portion side of the circuit board. The second reflector and the third reflector face each other in the first direction. The first reflector is overlapped with the circuit board in a third direction perpendicular to the first direction and the second direction. The second reflector and the third reflector are disposed to face the first reflector. The second reflector and the third reflector are disposed to be spaced apart from the other end portion in the second direction.

The roller assembly may include a roller; a first gear coupled to the roller; and a second gear engaged with the first gear. The number of teeth of the second gear may be greater than the number of teeth of the first gear.

The cylinder may include a second nozzle opened toward the ultraviolet light emitting device.

The sterilization device may include a reflection member disposed on the circuit board.

The reflection member may include a fourth reflector disposed on the circuit board, and the fourth reflector may include a through hole in which the ultraviolet light emitting device is disposed.

The reflection member may include a fifth reflector and a sixth reflector which are bent from both ends of the fourth reflector and face each other. The through hole may extend to the fifth reflector and the sixth reflector.

The second nozzle may be disposed corresponding to the through hole.

The power transmission member may include a crank arm rotated by the roller assembly and a connecting rod configured to connect the crank arm to the pump assembly.

The frame may include a pair of sidewall portions facing each other; a first support portion configured to connect the pair of sidewall portions and on which the first reflector is disposed; and a second support portion, respectively, and a third support portion which are connected to the pair of sidewall portions and on which the second reflector and the third reflector are disposed, respectively.

The frame may include an opening defined by the pair of sidewall portions and the first support portion. The air ejection module and the opening may be disposed on sides opposite to each other on the basis of the first support portion.

The first support portion may include a first area in which the first reflector is disposed; and a second area configured to connect the pair of sidewall portions and to surround the first area. A pair of slits passing through the first support portion may be disposed between the second area and both ends of the first area in the first direction.

A 2-2nd aspect of the present invention provides a sterilization device including a frame; a circuit board disposed on the frame; an ultraviolet light emitting device disposed on the circuit board; a first reflector disposed on the frame; and an air ejection module disposed on the frame to come into contact with a moving structure. Here, the first reflector is disposed to face the ultraviolet light emitting device. The air ejection module includes a roller assembly including a roller rotating according to movement of the moving structure and a pump assembly. The pump assembly includes a cylinder; a piston disposed in the cylinder; and a first nozzle opened toward the first reflector. The air ejection module includes a power transmission member configured to connect the roller assembly to the piston.

The first reflector may be disposed below the moving structure to face the moving structure.

A 3-1st aspect of the present invention provides a sterilization module including a frame including a support portion including one surface and one end portion and a fastening portion connected to the one end portion; a first circuit board disposed on the fastening portion; and an ultraviolet light emitting device disposed on the first circuit board. Here, the support portion includes another end portion opposite to the one end portion and side end portions facing each other with the other end portion therebetween. The frame includes a protruding portion connected to the side end portions of the support portion and a guide portion connected to the other end portion of the support portion. The fastening portion and the guide portion extend in a first direction perpendicular to the one surface of the support portion. The protruding portion extends in a direction opposite to the first direction. The guide portion includes a first guide portion and a second guide portion disposed to be spaced apart from each other in a second direction parallel to the one end portion. The other end portion includes a recess between the first guide portion and the second guide portion, and the recess is concave toward the one end portion.

The side end portions may include a first side end portion and a second side end portion facing each other. Here, the protruding portion may include a first protruding portion and a second protruding portion connected to the first side end portion and the second side end portion, respectively.

The support portion may include a first fastening hole passing through the one surface to another surface of the support portion.

The first fastening hole may include a 1-1 fastening hole and a 1-2 fastening hole which are disposed to be spaced apart from each other in the second direction.

The first fastening hole may be disposed to be closer to the side end portion than the guide portion.

The other end portion may include a concave portion concave toward the one end portion. The guide portion and the recess may be disposed in the concave portion.

A plurality of such ultraviolet light emitting devices may be disposed to be spaced part from each other in the second direction.

The sterilization module may include a reflection member disposed on the first circuit board. Here, the reflection member may include a first reflector disposed on the first circuit board; and a second reflector and a third reflector connected to both ends of the first reflector in the first direction. The first reflector may include a first through hole in which the ultraviolet light emitting device is disposed. A distance between the second reflector and the third reflector may gradually increase in a direction away from the first circuit board.

A 3-2nd aspect of the present invention provides a sterilization device including a case; a housing disposed in the case; a sterilization module disposed in the housing; a first cover disposed above the sterilization module; and a wiring portion configured to supply power to the sterilization module. Here, the sterilization module includes a frame including a support portion including one surface and one end portion and a fastening portion connected to the one end portion; a first circuit board disposed on the fastening portion; and an ultraviolet light emitting device disposed on the first circuit board. The support portion includes another end portion opposite to the one end portion and side end portions facing each other with the other end portion therebetween. The frame includes a protruding portion connected to the side end portions of the support portion and a guide portion connected to the other end portion of the support portion. The fastening portion and the guide portion extend in a first direction perpendicular to the one surface of the support portion. The protruding portion extends in a direction opposite to the first direction. The other end portion includes a recess concave toward the one end portion. The wiring portion is connected to the first circuit board and extends toward an inside of the housing through the recess.

The guide portion may include a first guide portion and a second guide portion spaced apart in a second direction parallel to the one end portion, and the recess may be disposed between the first guide portion and the second guide portion.

The sterilization device may include a second circuit board disposed inside the housing; and a connector disposed on the second circuit board. Here, the wiring portion may be connected to the connector.

The support portion may be disposed on a front portion of the housing, and the front portion may include a second through hole overlapped with the recess.

The support portion may be disposed on a front portion of the housing, and the front portion may include a pair of third fastening holes passing through the front portion. The first guide portion and the second guide portion may be disposed in the pair of third fastening holes, respectively.

The support portion may be disposed on a front surface of the housing. Here, the support portion may include a first fastening hole passing through the one surface to another surface of the support portion, and the front surface may include a second fastening hole corresponding to the first fastening hole.

The sterilization module may be fixed to the housing by a fastening member coupled to the first cover and extending to the first fastening hole and the second fastening hole.

The sterilization device may include a fourth reflector and a fifth reflector disposed in the case. Here, the fourth reflector and the fifth reflector may be disposed on both end sides of the fastening portion in a second direction parallel to the one end portion. A distance between the fourth reflector and the fifth reflector may gradually be reduced in a direction away from the first circuit board.

A fourth aspect of the present invention provides an ultraviolet irradiation device including a first housing including a top portion and a pair of first side portions facing each other with the top portion therebetween; a pair of second housings coupled to the pair of first side portions, respectively; and a light source module disposed on the top portion of the first housing and including an ultraviolet light emitting device. Here, the pair of first side portions each include a first fastening hole. Each of the second housings includes a second side portion connected to the first side portion and a first bent portion bent from the second side portion and extending toward a space between the first side portions. The second side portions each include a second fastening hole disposed at a position overlapped with the first fastening hole. The second fastening hole has a long hole shape longer than the first fastening hole in a direction facing the first bent portion. The ultraviolet light emitting device may be disposed to face a space between a pair of the first bent portions.

The ultraviolet irradiation device may include fastening members disposed in the first fastening hole and the second fastening hole, respectively.

The first bent portions may each include a third fastening hole.

A distance between a pair of such first bent portions may be shorter than a distance between a pair of such second side portions.

The first side portion may include a fourth fastening hole passing through the first side portion. The second housing may include a first protruding portion bent from the second side portion and disposed in the fourth fastening hole. The second side portion and the first protruding portion may be disposed on both surfaces of the first side portion, respectively. The first protruding portion may extend to be parallel to a direction opposite to the second side portion.

The light source module may include a frame and a first circuit board disposed on the frame. A plurality of such ultraviolet light emitting devices may be arranged on the first circuit board in a first direction. The frame may include a fixing portion; a second bent portion bent from the fixing portion; and a pair of second protruding portions bent from both ends of the fixing portion to face each other. The first circuit board may be disposed on the second bent portion. The fixing portion may include a first side surface connected to the second bent portion and a second side surface facing the first side surface. The fixing portion may include a first recess formed in the second side surface to be concave toward the first side surface and a fifth fastening hole passing through one surface and another surface of the fixing portion.

The ultraviolet irradiation device may include a reflection member disposed on the first circuit board. Here, the reflection member may include a first reflector disposed on the first circuit board; and a second reflector and a third reflector bent from both ends of the first reflector in a second direction perpendicular to the first direction. The first reflector may include a plurality of first through holes in which the plurality of ultraviolet light emitting devices are disposed. A distance between the second reflector and the third reflector may gradually increase in a direction away from the first circuit board.

The first housing may include a top portion and a front portion disposed to be perpendicular to the pair of first side portions. The front portion may include a sixth fastening hole corresponding to the fifth fastening hole and fastening members disposed in the fifth fastening hole and the sixth fastening hole.

The ultraviolet irradiation device may include a second circuit board disposed on the top portion and a connector disposed on the second circuit board. The front portion may include a second through hole overlapped with the first recess to allow the connector to be exposed.

The frame may include a pair of third protruding portions bent from the fixing portion to face the second bent portion. The front portion may include a pair of seventh fastening holes. The pair of third protruding portions may be disposed in the pair of seventh fastening holes, respectively.

The fixing portion may include a pair of convex portions protruding into the first recess and connected to the pair of third protruding portions and a concave portion disposed between the pair of convex portions.

The fixing portion may have a first width from the first side surface to the concave portion, which is smaller than a second width from the first side surface to the convex portion.

The ultraviolet irradiation device may include a case configured to surround the housing. The case may include a top case facing the top portion, a pair of side cases facing the pair of first side portions, and a front case facing the front portion.

The ultraviolet irradiation device may include a fourth reflector and a fifth reflector disposed in the pair of side cases. Here, the fourth reflector and the fifth reflector may be disposed to be spaced apart in the first direction. A distance between the fourth reflector and the fifth reflector may gradually be reduced in a direction away from the first circuit board.

The fourth reflector and the fifth reflector may reflect part of light emitted from the plurality of ultraviolet light emitting devices.

Advantageous Effects

A sterilization module according to embodiments can be easily attachable to or detachable from a sterilization device.

The sterilization device according to embodiments can solve a problem of a degradation in sterilizing power which is caused by contamination of a light source with foreign substances stacked on the light source.

Also, the light source or a reflector can be cleaned by periodical air ejection.

Also, side surfaces of the handrail can be sterilized without disposing light sources on side surfaces of the handrail.

In an ultraviolet irradiation device according to embodiments, a second fastening hole can have a long hole shape so as to be compatible with a variety of SUS type escalators and the like. Also, a first housing is left unchanged and a second housing can be replaced with a third housing so as to be compatible with a glass type escalator or the like.

Also, a light source module can be easily attachable to or detachable from the ultraviolet irradiation device.

A variety of advantages and effects of the present invention are not limited thereto and will be easily understood throughout the detailed description of the embodiments.

DESCRIPTION OF DRAWINGS

FIG. 1 is a view illustrating a target structure;

FIG. 2 is a view illustrating a state in which a sterilization device according to a first embodiment of the present invention is mounted on the target structure of FIG. 1;

FIG. 3 is a perspective view of the sterilization device of FIG. 2;

FIG. 4 is an exploded perspective view of the sterilization device of FIG. 3;

FIG. 5 is a perspective view illustrating a first frame of FIG. 4;

FIG. 6 is a perspective view illustrating a second frame of FIG. 4;

FIG. 7 is a perspective view of a light source module of FIG. 3;

FIG. 8 is an exploded perspective view of the light source module of FIG. 7;

FIG. 9 is a front view of the light source module of FIG. 7;

FIG. 10 is a side view of the light source module of FIG. 7;

FIG. 11 is a perspective view of an air ejection module of FIG. 3;

FIG. 12 is a plan view of the air ejection module of FIG. 11;

FIG. 13 is an exploded perspective view of a roller assembly of FIG. 11;

FIG. 14 is a cross-sectional view taken along line A-A of FIG. 12;

FIG. 15 is a cross-sectional view taken along line B-B of FIG. 12;

FIG. 16 is a cross-sectional view of the sterilization device of FIG. 3;

FIG. 17 is an enlarged view illustrating part A of FIG. 16;

FIG. 18 is a front view of the sterilization device of FIG. 3;

FIG. 19 is a view illustrating a basic example of the sterilization device of FIG. 2;

FIG. 20 is a view illustrating a state in which a sterilization device according to a second embodiment of the present invention is mounted on the target structure;

FIG. 21 is a perspective view of the sterilization device of FIG. 20;

FIG. 22 is an exploded perspective view of the sterilization device of FIG. 21;

FIG. 23 is a perspective view of a sterilization module of FIG. 22;

FIG. 24 is an exploded perspective view of the sterilization module of FIG. 23;

FIG. 25 is a front view of the sterilization module of FIG. 23;

FIG. 26 is a plan view of the sterilization module of FIG. 23;

FIG. 27 is a side view of the sterilization module of FIG. 23;

FIG. 28 is a view illustrating a front portion of a housing of FIG. 22;

FIG. 29 is a view illustrating a state in which the sterilization module is coupled to the front portion of FIG. 28;

FIG. 30 is a view illustrating a wiring portion connected to the sterilization module of FIG. 23;

FIG. 31 is a cross-sectional view of the sterilization device of FIG. 21;

FIG. 32 is a cross-sectional view taken along line A-A of FIG. 31;

FIG. 33 is a perspective view illustrating a state in which an ultraviolet irradiation device according to a third embodiment of the present invention is mounted on the target structure;

FIG. 34 is a perspective view of the ultraviolet irradiation device of FIG. 33;

FIG. 35 is an exploded perspective view of the ultraviolet irradiation device of FIG. 34;

FIG. 36 is a plan view illustrating a state in which a housing of FIG. 35 is fixed to the target structure;

FIG. 37 is a side view illustrating a state in which the housing of FIG. 35 is fixed to the target structure;

FIG. 38 is a side view illustrating a state in which the housing of FIG. 35 is fixed to a target structure having a different size;

FIGS. 39 to 41 are views illustrating a process of coupling a second housing to a first housing of FIG. 35;

FIG. 42 is a perspective view illustrating a light source module of FIG. 35;

FIG. 43 is an exploded perspective view of the light source module of FIG. 42;

FIG. 44 is a front view of the light source module of FIG. 42;

FIG. 45 is a plan view of the light source module of FIG. 42;

FIG. 46 is a side view of the light source module of FIG. 42;

FIG. 47 is a plan view illustrating a front portion of the first housing of FIG. 35;

FIG. 48 is a view illustrating a state in which the light source module is coupled to the front portion of FIG. 47;

FIG. 49 is a cross-sectional view of the ultraviolet irradiation device of FIG. 34;

FIG. 50 is a cross-sectional view taken along line A-A of FIG. 49;

FIG. 51 is a perspective view illustrating an ultraviolet irradiation device according to a fourth embodiment of the present invention;

FIG. 52 is an exploded perspective view of a housing and a fixing portion of FIG. 51;

FIGS. 53 to 56 are views illustrating a variety of examples of installing the ultraviolet irradiation device of FIG. 51; and FIG. 57 illustrates a basic example of the ultraviolet irradiation device of FIG. 33.

MODES OF THE INVENTION

Hereinafter, exemplary embodiments of the present invention will be described in detail with reference to the drawings.

However, the present invention is not limited to the embodiments disclosed below but can be implemented in various forms. One or more components of the embodiments may be selectively combined or substituted with one another without departing from the scope of the technical concept of the present invention.

Also, unless defined otherwise, the terms (including technical and scientific terms) used herein may be used as meanings capable of being commonly understood by one of ordinary skill in the art. Also, terms defined in generally used dictionaries may be construed in consideration of the contextual meanings of the related art.

Also, the terms used herein are intended to describe the embodiments but not intended to restrict the present invention.

Throughout the specification, unless stated otherwise particularly, singular forms include plural forms. When at least one (or one or more) of A, B, and C is stated, this may include one or more of all combinations of A, B, and C.

Also, in describing components of the embodiments of the present invention, the terms such as first, second, A, B, (a), (b), and the like may be used.

These terms are merely for distinguishing one element from another, and the essential, order, sequence, and the like of corresponding elements are not limited by the terms.

Also, when it is stated that one element is "connected," "coupled," or "joined" to another, the element may not only be directly connected, coupled, or joined to the other element but also be connected, coupled, or joined to the other element with another intervening element.

Also, when it is stated that an element is formed or disposed "above or below" another element, the two elements may not only come into direct contact with each other but also still another element may be formed or disposed between the two elements. Also, being "above (on) or below (beneath)" may include not only being an upward direction but also being a downward direction on the basis of one element.

FIG. 1 is a view illustrating a target structure, FIG. 2 is a view illustrating a state in which a sterilization device according to a first embodiment of the present invention is mounted on the target structure of FIG. 1, and FIG. 19 is a view illustrating a basic example of the sterilization device of FIG. 2.

Referring to FIG. 1, a target structure 20 may include all of a variety of structures such as an escalator and moving walk which transfer a user to a designated position.

The target structure 20 may include a moving structure 21 and a frame 23 including an internal space which the moving structure 21 enters or exits from. The moving structure 21 may mean a handrail provided in an escalator or moving walk but is not necessarily limited thereto. Hereinafter, only a case in which the moving structure 21 is a handrail of an escalator or moving walk will be described.

Referring to FIG. 2, a sterilization device 10 according to the first embodiment of the present invention may be fixed to a housing 23 of the target structure by a fastening member such as a bolt and the like. Here, the sterilization device 10 may be disposed inside the housing 23. However, the present invention is not necessarily limited thereto, and the sterilization device 10 may be fixed to another component of the target structure or may be disposed to be exposed to the outside of the target structure.

FIG. 3 is a perspective view of the sterilization device of FIG. 2, and FIG. 4 is an exploded perspective view of the sterilization device of FIG. 3.

Referring to FIGS. 3 and 4, the sterilization device 10 may include a frame 100, a light source module 200, first to third reflectors 410, 420, and 430, and an air ejection module 300.

The frame 100 may include a first frame 110 fixed to the housing of the target structure and a second frame 120 fixed to the first frame 110.

A substrate 111 to which the light source module 200 is fixed may be disposed on the first frame 110. The substrate 111 may be integrally formed with the first frame 110 but is not necessarily limited thereto.

The first frame 110 may accommodate the air ejection module 300.

The second frame 120 may be coupled to the first frame 110 by a fastening member such as a bolt or the like.

The second frame 120 may include a pair of sidewall portions 121a and 121b facing each other, a first support portion 123 configured to connect a bottom of a first sidewall portion 121a to a bottom of a second sidewall portion 121b, a second support portion 125a connected to a top of the first sidewall portion 121a, and a third support portion 125b connected to a top of the second sidewall portion 121a. The second support portion 125a and the third support portion 125b may be disposed to face each other. The second frame 120 may include an opening defined by the pair of sidewall portions 121a and 121b and the first support portion 123. The air ejection module 300 and the opening of the second frame 120 may be disposed on sides opposite to each other on the basis of the first support portion 123. Accordingly, foreign substances may be discharged by air ejected by the air ejection module 300 through the opening of the second frame 120.

The pair of sidewall portions 121a and 121b may be coupled to the first frame 110 by a fastening member such as a bolt or the like.

The light source module 200 may emit ultraviolet rays and be coupled to the substrate 111 by a fastening member such as a bolt or the like.

The air ejection module 300 may be disposed to come into contact with the moving structure and may generate an airflow ejected toward a first reflecting surface of the first reflector 410 according to movement of the moving structure.

The air ejection module 300 may include a roller assembly 310 including a roller rotating according to movement of the moving structure, a pump assembly 320 configured to generate an airflow ejected toward the first reflecting surface of the first reflector 410, and a power transmission member 330 configured to provide the pump assembly 320 with torque of the roller assembly 310 as a power source. The power transmission member 330 may include a crank tool. However, the present invention is not necessarily limited thereto, and the air ejection module 300 may include a fan or blower (not shown) configured to rotate due to torque of the roller assembly 310 instead of the pump assembly 320.

The first reflector 410 may be disposed on the first support portion 123, the second reflector 420 may be disposed on the second support portion 125a, and the third reflector 430 may be disposed on the third support portion 125b. The first to third reflectors 410, 420, and 430 may be disposed inside the second frame 120.

The first to third reflectors 410, 420, and 430 may include aluminum (Al) but are not necessarily limited thereto and may include other materials having a high ultraviolet reflection rate.

The first to third reflectors 410, 420, and 430 may be fixed to the second frame 120 using an adhesive (not shown).

FIG. 5 is a perspective view illustrating the first frame of FIG. 4.

Referring to FIGS. 4 and 5, the first frame 110 may include a first vertical portion 113 fixed to the housing of the target structure, a second vertical portion 115 facing the first vertical portion 113, an accommodation portion 117 disposed between the first vertical portion 113 and the second vertical portion 115, and a horizontal portion 119 bent from the second vertical portion 115. The substrate 111 may be connected to the horizontal portion 119 to be tilted. The accommodation portion 117 may include a cavity 117a with one open surface.

The roller assembly 310 may be inserted into the cavity 117a through the open one surface of the cavity 117a. A case of the roller assembly 310 may include a step portion mounted on the horizontal portion 119.

The pump assembly 320 may be coupled to the horizontal portion 119 by a fastening member such as a bolt or the like.

The second vertical portion 115 may include a pair of through holes 115a into which connecting rods of a pair of such power transmission members 330 are inserted, and the accommodation portion 117 may include a pair of guide slits 117b into which both ends of a crank shaft disposed on the roller assembly 310 are inserted.

FIG. 6 is a perspective view illustrating the second frame of FIG. 4.

Referring to FIGS. 4 and 6, the first support portion 123 may include a first area 123a in which the first reflector 410 is disposed and a second area 123b configured to connect the pair of sidewall portions 121a and 121b and surround the first area 123a.

Both ends of the first area 123a may be connected to the second area 123b. Through slits 123c passing through the first support portion 123 may be disposed between the second area 123b and other both ends of the first area 123a. Accordingly, foreign substances may be smoothly discharged by the air ejected by the air ejection module 300 through not only the opening of the second housing 120 but also the pair of through slits 123c.

FIG. 7 is a perspective view of the light source module of FIG. 3, FIG. 8 is an exploded perspective view of the light source module of FIG. 7, FIG. 9 is a front view of the light source module of FIG. 7, and FIG. 10 is a side view of the light source module of FIG. 7.

Referring to FIGS. 7 and 8, the light source module 200 may include a circuit board 220 and an ultraviolet light emitting device 230 and may further include a fixing plate 210 and/or a reflection member 240.

The fixing plate 210 may assist heat dissipation of the ultraviolet light emitting device 230. The fixing plate 210 may include Al but is not necessarily limited thereto and may include other materials having an excellent heat dissipation property.

The circuit board 220 may be disposed on the fixing plate 210.

The circuit board 220 may include one end portion 221, another end portion 223, and a pair of side end portions 225 and 227 facing each other with the one end portion 221 therebetween. An X-axis direction (first direction) may be a direction parallel to the one end portion 221, a Y-axis direction (second direction) may be a direction parallel to the side end portions 225 and 227, and a Z-axis direction (third direction) may be a direction perpendicular to each of the X-axis direction and the Y-axis direction.

The ultraviolet light emitting device 230 may be disposed on the circuit board 220. When a plurality of such ultraviolet light emitting devices 230 are provided, the plurality of ultraviolet light emitting devices 230 may be arranged in a row in the X-axis direction. Although it is shown that four ultraviolet light emitting devices 230 are disposed on the circuit board 220, the present invention is not necessarily limited thereto. Three or less or five or more ultraviolet light emitting devices 230 may be disposed on the circuit board 220.

The ultraviolet light emitting devices 230 may output light UV-A of a near-ultraviolet wavelength range, may output light UV-B of a far-ultraviolet wavelength range, and may output light UV-C of a deep-ultraviolet wavelength range. A wavelength range of light may be determined by a composition ratio of Al in a semiconductor structure.

For example, the light UV-A of the near-ultraviolet wavelength range may have a range from 320 nm to 420 nm, the light UV-B of the far-ultraviolet wavelength range may have a range from 280 nm to 320 nm, and the light UV-C of the deep-ultraviolet wavelength range may have a range from 100 nm to 280 nm.

The reflection member 240 may be disposed on the circuit board 220 and may be fixed to the fixing plate 210 with the circuit board 220 by a fastening member such as a bolt or the like.

The reflection member 240 may restrict a light emission range of the ultraviolet light emitting device 230 to be, for example, within the first reflector. The reflection member 240 may include Al but is not necessarily limited thereto and may include other materials having a high ultraviolet light reflectance. Also, the reflection member 240 may perform a heat dissipation function of externally dissipating heat generated from the ultraviolet light emitting device 230. It may be significant for the ultraviolet light emitting device 230 to quickly dissipate heat.

Referring to FIG. 9, the reflection member 240 may include a fourth reflector 244 disposed on the circuit board 220 and a fifth reflector 245 and a sixth reflector 246 bent from both ends of the fourth reflector 244 in the Y-axis direction.

The fourth reflector 244 may include a through hole 244a in which the ultraviolet light emitting device 230 is disposed. When the plurality of ultraviolet light emitting devices 230 are provided, one ultraviolet light emitting device 230 may be disposed for each through hole 244a.

The fifth reflector 245 and the sixth reflector 246 may extend in the X-axis direction, and the fifth reflector 245 and the sixth reflector 246 may be disposed to face each other while being spaced apart in the Y-axis direction.

Referring to FIG. 10, the fifth reflector 245 and the sixth reflector 246 may include a fifth reflecting surface C5 and a sixth reflecting surface C6 which face each other, respectively.

The fifth reflector 245 and the sixth reflector 246 may be disposed to be tilted from the fourth reflector 244 at a certain angle. That is, a distance D1 between the fifth reflecting surface C5 and the sixth reflecting surface C6 may gradually increase in a direction away from the circuit board 220. For example, the angle formed between the fifth reflecting surface C5 and the sixth reflecting surface C6 may be from 20 degrees to 60 degrees but is not necessarily limited thereto.

FIG. 11 is a perspective view of the air ejection module of FIG. 3, FIG. 12 is a plan view of the air ejection module of FIG. 11, FIG. 13 is an exploded perspective view of the roller assembly of FIG. 11, FIG. 14 is a cross-sectional view taken along line A-A of FIG. 12, and FIG. 15 is a cross-sectional view taken along line B-B of FIG. 12.

Referring to FIG. 11, the air ejection module 300 may include the roller assembly 310 including the roller rotating according to movement of the moving structure, the pump assembly 320 configured to generate an airflow ejected toward the first reflecting surface of the first reflector 410, and the power transmission member 330 configured to provide the pump assembly 320 with torque of the roller assembly 310 as a power source. The power transmission member 330 may include a crank tool.

The torque of the roller assembly 310 may be converted into power which is supplied to the light source module.

The power transmission member 330 may include a crank arm 331 rotated by the roller assembly 310 and a connecting rod 333 configured to connect the crank arm 331 to the pump assembly 320.

The connecting rod 333 may be rotatably connected to the crank arm 331 through a first pin P1 and rotatably connected to the pump assembly 320 through a second pin P2. The first pin P1 may be disposed to be parallel to a crank shaft S2 which is a rotating shaft of the crank arm 331. However, the present invention is not necessarily limited thereto and a variety of well-known power transmission members capable of converting torque into a reciprocating action may be included as the power transmission member 330.

Referring to FIG. 12, the torque of the roller assembly 310 may be stably transmitted to the pump assembly 320 through the pair of power transmission members 330.

Referring to FIG. 13, the roller assembly 310 may include a roller 311 configured to come into contact with one surface of the moving structure and rotate according to movement of the moving structure and may further include a first gear 313 coupled to the roller 311, a second gear 315 engaged with the first gear 313, and/or a case 317. The case 317 may accommodate the roller 311, the first gear 313, and the second gear 315.

The number of teeth of the second gear 315 may be greater than the number of teeth of the first gear 313.

The case 317 may include an opening 317a disposed to expose a part of the roller 311 to the outside, a through hole 317b in which a rotating shaft S1 of the roller 311 is disposed, and a through hole 317c in which the crank shaft S2 which is the rotating shaft of the second gear 315 is disposed. To prevent separation from the case 317, stopper members P may be coupled to both ends of the rotating shaft S1 of the roller 311 and the crank arms 331 may be coupled to both ends of the crank shaft S2.

Referring to FIG. 14, the pump assembly 320 may include a cylinder 321 and a piston 323 disposed in the cylinder 321. The cylinder 321 may include a first nozzle 321a opened toward the first reflecting surface of the first reflector.

The second pin P2 of the power transmission member may be disposed in the piston 323. Accordingly, the piston 323 may reciprocate inside the cylinder 321 due to the power transmission member. When the piston 323 moves toward the first nozzle 321a, air inside the cylinder 321 may be compressed. The air compressed by the piston 323 may be ejected through the first nozzle 321a toward the first reflecting surface of the first reflector. The air ejected through the first nozzle 321a may externally discharge foreign substances falling from the handrail and stacked on the first reflecting surface of the first reflector.

Referring to FIG. 15, the cylinder 321 may further include a second nozzle 321b opened toward the light source module. The air compressed by the piston 323 may be ejected through the first nozzle 321a and the second nozzle 321b. The air ejected through the second nozzle 321b may assist heat dissipation of the light source module. A cross-sectional area of an exit of the second nozzle 321b may be equal to or different from a cross-sectional area of an exit of the first nozzle 321a.

FIG. 16 is a cross-sectional view of the sterilization device of FIG. 3, FIG. 17 is an enlarged view illustrating part A of FIG. 16, and FIG. 18 is a front view of the sterilization device of FIG. 3.

Referring to FIGS. 16 and 17, the substrate 111 may include one surface 111a facing one surface 21a of the moving structure 21 and another surface 111b opposite to the one surface 111a. The light source module 200 may be disposed on the other surface 111b of the substrate 111. Here, the fixing plate 210 may be disposed between the substrate 111 and the circuit board 220 and improve heat dissipation performance of the light source module 200.

The light source module 200 may be disposed below the moving structure 21 but is not necessarily limited thereto.

The circuit board 220 may be disposed to be tilted at a first acute angle with respect to a direction in which the moving structure 21 moves. For example, an angle θ1 between one surface of the circuit board 220 and the moving structure 21 may be greater than zero degrees and smaller than 90 degrees and may preferably be greater than or equal to 45 degrees and smaller than 90 degrees. When the angle θ1 is greater than or equal to 45 degrees, the number of reflectors necessary for transmitting light of the light module 200 to the one surface 21a of the moving structure 21 may be minimized. For example, when the angle θ1 is smaller than 45 degrees, two or more reflectors may be necessary for transmitting light of the light module 200 to the one surface 21a of the moving structure 21. However, the present invention is not necessarily limited thereto, and the angle θ1 may be smaller than 45 degrees. When the angle θ1 may be smaller than 90 degrees, it is possible to solve a problem of foreign substances attached to a surface of the moving structure 21 falling directly on the light source module 200.

The first reflector 410 may be overlapped with the circuit board 220 in the Z-axis direction. Accordingly, all light emitted from the ultraviolet light emitting devices 230 may be emitted toward the first reflector 410.

On the other hand, the second reflector 420 and the third reflector 430 may not be overlapped with the first circuit board 220 in the Z-axis direction. For example, the second reflector 420 and the third reflector 430 may be disposed to be spaced apart from the other end portion 223 of the circuit board 220 in the Y-axis direction.

The first reflector 410 may be disposed to be tilted with respect to the Y-axis direction. That is, the first reflector 410 may be disposed to be tilted with respect to the circuit board 220. The second reflector 420 and the third reflector 430 may be disposed to face the first reflector 410. Accordingly, light emitted from the ultraviolet light emitting devices 230 may be emitted toward the first reflector 410 and at least a part of the light reflected by the first reflector 410 may be emitted toward the second reflector 420 and the third reflector 430.

The first reflector 410 may include a first reflecting surface C1 disposed to face the moving structure 21, and the first reflecting surface C1 may be disposed to be tilted at a second acute angle smaller than the first acute angle with respect to the moving structure 21. That is, an angle θ2 between the first reflecting surface C1 and the moving structure 21 may be greater than zero degrees and smaller than the angle θ1 between the one surface of the circuit board 220 and the moving structure. Accordingly, the light emitted by the ultraviolet light emitting devices 230 may be reflected by the first reflecting surface C1 and emitted toward the one surface 21a of the moving structure 21. Meanwhile, when the first reflecting surface C1 has a curvature, the angle θ2 between the first reflecting surface C1 and the moving structure 21 may mean an angle between the moving structure 21 and a virtual segment B which connects both ends of the first reflecting surface C1.

The first reflector 410 may include a first end portion 410a and a second end portion 410b facing the first end portion 410a and disposed to be farther from the circuit board 220 than the first end portion 410a. The first reflector 410 may have a curvature from the first end portion 410a to the second end portion 410b and may have a concave shape toward the ultraviolet light emitting devices 230 and the moving structure 21. Accordingly, the first reflecting surface C1 may improve sterilization performance by condensing the light of the ultraviolet light emitting devices 230. The first reflecting surface C1 may be divided into a plurality of areas having different curvatures.

The through hole 244a of the fourth reflector 244 may extend to the fifth reflector 245 and the sixth reflector 246. Accordingly, a side surface of the ultraviolet light emitting device 230 may be exposed outward through the through hole 244a. Also, air ejected by the second nozzle 321b of the pump assembly 320 may reach the ultraviolet light emitting device 230 through the through hole 244a. That is, the through hole 244a may provide a path through which the air ejected by the second nozzle 321b moves toward the ultraviolet light emitting device 230. As a result, it is possible to assist heat dissipation of the ultraviolet light emitting device 230. A plurality of such second nozzles 321b may be disposed corresponding to a plurality of such through holes 244a. For example, when there are four through holes 244a, four second nozzles 321b may be provided. The plurality of first nozzles 321a may each be disposed between the plurality of second nozzles 321b but are not necessarily limited thereto.

Referring to FIG. 18, the first reflector 410 may be disposed on one end portion side of the circuit board 220, and the second reflector 420 and the third reflector 430 may be disposed on the other end portion side of the circuit board 220.

The second reflector 420 and the third reflector 430 may be disposed to be overlapped with the moving structure 21 in the X-axis direction and may face both side surfaces 21b of the moving structure 21.

The second reflector 420 and the third reflector 430 may be disposed to be tilted with respect to the X-axis direction. The second reflector 420, the third reflector 430, and the moving structure 21 may be disposed to face the first reflector 410. Accordingly, light reflected by the first reflector 410 may be emitted toward the one surface 21a of the moving structure 21 and reflected by the second reflector 420 and the third reflector 430 to be emitted toward the both side surfaces 21b of the moving structure 21.

The second reflector 420 may include a second reflecting surface C2, and the third reflector 430 may include a third reflecting surface C3.

A distance D2 between the second reflecting surface C2 and the third reflecting surface C3 may be gradually reduced in a direction away from the first reflector 410. A maximum value of the distance D2 between the second reflecting surface C2 and the third reflecting surface C3 may be greater than a length of the other end portion 223 of the circuit board 220 in the X-axis direction.

The second reflector 420 and the third reflector 430 may include third end portions 420a and 430a and fourth end portions 420b and 430b facing the third end portions 420a and 430a and disposed to be farther from the first reflector 410 than the third end portions 420a and 430a, respectively. The second reflector 420 and the third reflector 430 may have curvatures from the third end portions 420a and 430a to the fourth end portions 420b and 430b, respectively, and may have a concave shape toward each other. Accordingly, the second reflecting surface C2 and the third reflecting surface C3 may improve sterilization performance by condensing light.

The first reflecting surface C1 may be disposed to face the one surface 21a of the moving structure 21, the second reflecting surface C2, and the third reflecting surface C3. For example, a width W1 of the first reflecting surface C1 in the X-axis direction may be greater than a width W2 of the moving structure 21 in the X-axis direction. Accordingly, the first reflecting surface C1 may reflect light emitted from the light source module 200 and emit the light toward the one surface 21a of the moving structure 21, the second reflecting surface C2, and the third reflecting surface C3. The second reflecting surface C2 and the third reflecting surface C3 may reflect a part of light emitted from the light source module 200 and reflected by the first reflecting surface C1 and may emit the light toward the both side surfaces 21b of the moving structure 21. Meanwhile, the plurality of ultraviolet light emitting devices 230 may be arranged in the X-axis direction and uniformly emit ultraviolet rays toward the moving structure 21.

There is provided a method of installing a sterilization device on a moving structure. Here, the sterilization device includes a frame; a circuit board disposed on the frame and including one end portion, another end portion, and one surface; an ultraviolet light emitting device disposed on the one surface of the circuit board; and a first reflector, a second reflector, and a third reflector which are disposed on the frame. The method includes disposing the frame below the moving structure; disposing another surface of the circuit board which is opposite to the one surface of the circuit board to face the moving structure; disposing the one end portion of the circuit board to be farther from the moving structure than the other end portion; disposing the first reflector below the one end portion of the circuit board to face the circuit board and the moving structure; disposing the second reflector and the third reflector above the other end portion of the circuit board; allowing the second reflector and the third reflector to face each other with the moving structure therebetween; and disposing the second reflector and the third reflector to face the first reflector and the moving structure. In the above, respective operations of the method of installing the sterilization device are not restricted by an order.

There is provided a method of sterilizing a moving structure using a sterilization device. Here, the sterilization device includes a frame; a circuit board disposed on the frame and including one end portion and another end portion; an ultraviolet light emitting device disposed on one surface of the circuit board; and a first reflector, a second reflector, and a third reflector which are disposed on the frame. The moving structure includes a bottom surface and both side surfaces. The sterilization method includes emitting first ultraviolet light rays in a direction away from the moving structure below the moving structure; reflecting the first ultraviolet rays, using the first reflector, as second ultraviolet rays toward a bottom surface of the moving structure, the second reflector, and the third reflector; and reflecting the second ultraviolet rays, using the second reflector and the third reflector, as third ultraviolet rays toward the both side surfaces of the moving structure.

The components stated above in the method of sterilizing using the sterilization device and the method of sterilizing the moving structure may be referred to as the same reference numerals as the components having the same designations described above with reference to FIGS. 1 to 18.

FIG. 19 is a view illustrating a basic example of the sterilization device of FIG. 2.

Referring to FIG. 19, the sterilization device 10 may include the frame 100, the circuit board 220 disposed on the frame 100, the ultraviolet light emitting devices 230 disposed on the circuit board 220, the first reflector 410 disposed on the frame 100, and the air ejection module 300 disposed on the frame 100. The above description with reference to FIGS. 3 to 18 may be applied equally to the sterilization device 10 of FIG. 19.

FIG. 20 is a view illustrating a state in which a sterilization device according to a second embodiment of the present invention is mounted on the target structure.

Referring to FIG. 20, a sterilization device 1010 according to the second embodiment of the present invention may be mounted on a target structure 1020 and sterilize a moving structure 1030 of the target structure 1020. The target structure 1020 may include all of a variety of structures such as an escalator and moving walk which transfer a user to a designated position. The moving structure 1030 may mean a handrail provided on an escalator or moving walk but is not necessarily limited thereto. Hereinafter, only a case in which the moving structure 1030 is a handrail of an escalator or moving walk will be described.

The sterilization device 1010 may be mounted to be exposed outside the target structure 1020 but is not necessarily limited thereto and may be mounted in the target structure 1020. Also, a sterilization module may be separated from the sterilization device 1010 and installed to be disposed below the moving structure 1030 separately.

FIG. 21 is a perspective view of the sterilization device of FIG. 20, and FIG. 22 is an exploded perspective view of the sterilization device of FIG. 21.

Referring to FIGS. 21 and 22, the sterilization device 1010 may include a housing 1100, a sterilization module 1300, a case 1500, a first cover 1530, and a wiring portion (not shown) and may further include a coupling portion 1200 and/or a power source module 1400.

The housing 1100 may be disposed in the case 1500 and may include a top portion 1111, a pair of side portions 1113, a front portion 1115, and a rear portion 1117.

The top portion 1111 may be disposed to be perpendicular to the pair of side portions 1113, the front portion 1115, and the rear portion 1117.

The pair of side portions 1113 may be disposed to face each other. The front portion 1115 and the rear portion 1117 may be disposed to face each other and may be disposed to be perpendicular to the pair of side portions 1113.

A second circuit board 1130 may be disposed below the top portion 1111. That is, the second circuit board 1130 may be disposed in the housing 1100 defined by the top portion 1111, the pair of side portions 1113, the front portion 1115, and the rear portion 1117. A connector 1140 may be disposed on the second circuit board 1130.

The second circuit board 1130 may be an interface substrate configured to connect the sterilization module 1300 to the power source module 1400. The sterilization module 1300 may be connected to the second circuit board 1130 through the connector 1140.

The second circuit board 1130 may be connected to the power source module 1400 and may receive electricity generated by the power source module 1400. The coupling portion 1200 may fix the housing 1100 to the target structure.

The coupling portion 1200 may include a first coupling plate 1210 and a second coupling plate 1220 coupled to the pair of side portions 1113, respectively. The first coupling plate 1210 and the second coupling plate 1220 may be pressed against the target structure so as to fix the housing 1100 to the target structure. A distance between the first coupling plate 1210 and the second coupling plate 1220 may be adjusted. A structure capable of adjusting the distance between the first coupling plate 1210 and the second coupling plate 1220 is not particularly limited.

The sterilization module 1300 may emit ultraviolet rays and may be disposed on the housing 1100.

For example, the sterilization module 1300 may be fixed to the front portion 1115 of the housing 1100 by a fastening member such as a bolt or the like. The fastening member may be coupled to the first cover 1530 and extend toward a first fastening hole 1311d of the sterilization module 1300 and a second fastening hole 1115a of the front portion 1115. Here, since a position of the sterilization module 1300 is fixed while a guide portion 1317 is inserted into a third fastening hole of the front portion 1115, the first cover 1530 may be easily separated and coupled.

The power source module 1400 may generate electricity to be supplied to the sterilization module 1300 and may be coupled to the housing 1100.

The case 1500 may be coupled to the housing 1100 to form an exterior of the sterilization device 1010.

The case 1500 may include a plastic material but is not necessarily limited thereto.

The case 1500 may include a top case 1510 facing the top portion 1111 of the housing 1100 and a pair of side cases 1520 facing the pair of side portions 1113 of the housing 1100, respectively.

The top case 1510 may include a window 1511 configured to output sterilization-related information.

The pair of side cases 1520 may include a fourth reflector 1521a and a fifth reflector 1521b coupled to the side cases 1520 by fastening members such as bolts and the like to face each other. The fourth reflector 1521a and the fifth reflector 1521b may reflect ultraviolet rays emitted from the sterilization module 1300. The fourth reflector 1521a and the fifth reflector 1521b may be coupled to the case 1500 instead of the sterilization module 1300 so as to easily attach or detach the sterilization module 1300. The fourth reflector 1521a and the fifth reflector 1521b may include Al but are not necessarily limited thereto and may include other materials having a high ultraviolet reflection rate.

The first cover 1530 may be disposed on the front portion 1115 of the housing 1100. The first cover 1530 and the sterilization module 1300 may be fixed together to the front portion 1115 of the housing 1100 by fastening members such as bolts and the like. That is, the first cover 1530 may be attached to or detached from the front portion 1115 of the housing 1100. Accordingly, when the first cover 1530 is separated from the front portion 1115 of the housing 1100, the front portion 1115 of the housing 1100 may be exposed outside. Also, the sterilization module 1300 coupled to the front portion 1115 of the housing 1100 may be attached or detached.

The second cover 1540 may be disposed on the rear portion 1117 of the housing 1100. The second cover 1540 may be fixed to the rear portion 1117 of the housing 1100 by a fastening member such as a bolt or the like.

The first cover 1530 may include a first elastic pad 1531, and the second cover 1540 may include a second elastic pad 1541. The first elastic pad 1531 and the second elastic pad 1541 may prevent a hand of a user from being inserted into the case 1500. Also, it is possible to solve a problem in which the user's hand is caught between the case 1500 and the handrail and damaged.

The first elastic pad 1531 and the second elastic pad 1541 may include an elastic material such as silicone and the like.

The first elastic pad 1531 and the second elastic pad 1541 may be attached to or detached from the first cover 1530 and the second cover 1540, respectively. For example, the first cover 1530 and the second cover 1540 may include fourth fastening holes 1530a and 1540a, respectively, and the first elastic pad 1531 and the second elastic pad 1541 may include fifth protruding portions 1531a and 1541a which are inserted into the fourth fastening holes 1530a and 1540a, respectively.

The wiring portion may connect the second circuit board 1130 to the sterilization module 1300 and may supply electricity generated by the power source module 1400 to the sterilization module 1300.

FIG. 23 is a perspective view of the sterilization module of FIG. 22, and FIG. 24 is an exploded perspective view of the sterilization device of FIG. 23.

Referring to FIGS. 23 and 24, the sterilization module 1300 may include a frame 1310, a first circuit board 1320, and an ultraviolet light emitting device 1330 and may further include a reflection member 1340.

The frame 1310 may include a support portion 1311, a fastening portion 1313, a protruding portion 1315, and a guide portion 1317.

The support portion 1311 may include one end portion 1311a, another end portion 1311b opposite to the one end portion 1311a, and side end portions 1311c facing each other with the other end portion 1311b therebetween. The side end portions 1311c may include a first side end portion 1311c and a second side end portion 1311c which face each other.

The fastening portion 1313 may be connected to the one end portion 1311a of the support portion 1311, the protruding portion 1315 may be connected to the side end portion 1311c of the support portion 1311, and the guide portion 1317 may be connected to the other end portion 1311b of the support portion 1311.

The fastening portion 1313 and the guide portion 1317 may extend in an X-axis direction (first direction) perpendicular to one surface of the support portion 1311, and the protruding portion 1315 may extend in a direction opposite to the X-axis direction.

The protruding portion 1315 may include a first protruding portion 1315 and a second protruding portion 1315 which connect to the first side end portion 1311c and the second side end portion 1311c, respectively.

The guide portion 1317 may include a first guide portion 1317 and a second guide portion 1317 which are disposed to be spaced apart from each other in a Y-axis direction (second direction) parallel to the one end portion 1311*a* of the support portion 1311. The Y-axis direction may be perpendicular to the X-axis direction. The support portion 1311 may include a first fastening hole 1311*d* passing through the one surface to another surface of the support portion 1311. The first fastening hole 1311*d* may include a 1-1 fastening hole 1311*d* and a 1-2 fastening hole 1311*d* which are disposed to be spaced apart from each other in the Y-axis direction. The first fastening hole 1311*d* may be disposed to be closer to the side end portion 1311*c* of the support portion 1311 than the guide portion 1317. The other end portion 1311*b* of the support portion 1311 may include a recess 1311*e* between the first guide portion 1317 and the second guide portion 1317. The recess 1311*e* may have a concave shape toward the one end portion 1311*a* of the support portion 1311. The other end portion 1311*b* of the support portion 1311 may include a concave portion 1311*f* toward the one end portion 1311*a*. The guide portion 1317 and the recess 1311*e* may be disposed in the concave portion 1311*f*.

The frame 1310 may include Al but is not necessarily limited thereto and may include other materials having an excellent heat dissipation property.

The first circuit board 1320 may be disposed on the fastening portion 1313, and the ultraviolet light emitting device 1330 may be disposed on the first circuit board 1320. For example, a plurality of such ultraviolet light emitting devices 1330 may be disposed on the first circuit board 1320 to be spaced apart from each other in the Y-axis direction but the present invention is not necessarily limited thereto, and only one ultraviolet light emitting device 1330 may be disposed.

The ultraviolet light emitting devices 1330 may output light UV-A of a near-ultraviolet wavelength range, may output light UV-B of a far-ultraviolet wavelength range, and may output light UV-C of a deep-ultraviolet wavelength range. A wavelength range of light may be determined by a composition ratio of Al in a semiconductor structure.

For example, the light UV-A of the near-ultraviolet wavelength range may have a range from 320 nm to 420 nm, the light UV-B of the far-ultraviolet wavelength range may have a range from 280 nm to 320 nm, and the light UV-C of the deep-ultraviolet wavelength range may have a range from 100 nm to 280 nm.

The reflection member 1340 may be disposed on the first circuit board 1320. The reflection member 1340 and the first circuit board 1320 may be fixed together to the fastening portion 1313 using a fastening member such as a bolt or the like.

The reflection member 1340 may reflect light emitted from the ultraviolet light emitting device 1330. Also, the reflection member 1340 may perform a heat dissipation function of externally dissipating heat generated from the ultraviolet light emitting device 1330. It may be significant for the ultraviolet light emitting device 1330 to quickly dissipate heat.

The reflection member 1340 may include Al but is not necessarily limited thereto and may include other materials having a high ultraviolet light reflectance.

FIG. 25 is a front view of the sterilization module of FIG. 23, FIG. 26 is a plan view of the sterilization module of FIG. 23, and FIG. 27 is a side view of the light source module of FIG. 23.

Referring to FIG. 25, the frame 1310 may include a pair of third protruding portions 1319*a* bent from one end of the fastening portion 1313 in the X-axis direction and a pair of fourth protruding portions 1319*b* bent from another end of the fastening portion 1313 in the second direction. The third protruding portions 1319*a* may be disposed below the fourth protruding portions 1319*b*. That is, a distance between the support portion 1311 and the third protruding portions 1319*a* may be greater than a distance between the support portion 1311 and the fourth protruding portions 1319*b*.

The third protruding portions 1319*a* and the fourth protruding portions 1319*b* may be adjacent to side surfaces of the first circuit board 1320 which face each other. Particularly, the pair of third protruding portions 1319*a* may be disposed in a pair of second recesses 1320*a* formed in the first circuit board 1320. Accordingly, the first circuit board 1320 may be stably supported, on the fastening portion 1313, by the third protruding portions 1319*a* and the fourth protruding portions 1319*b*. As a result, a user may fasten a fastening member B such as a bolt and the like while the first circuit board 1320 is stably supported.

The third protruding portions 1319*a* and the fourth protruding portions 1319*b* may be disposed while being spaced apart in the Y-axis direction. That is, the third protruding portions 1319*a* and the fourth protruding portions 1319*b* may be mutually misaligned. Accordingly, an area in which a circuit pattern (not shown) of the first circuit board 1320 may be formed without interference with the second recesses 1320*a* may be secured above or below the ultraviolet light emitting device 1330.

The plurality of ultraviolet light emitting devices 1330 may be disposed to be spaced apart from each other in the Y-axis direction.

The reflection member 1340 may include a first reflector 1341 disposed on the first circuit board 1320 and second and third reflectors 1342 and 1343 connected to both ends of the first reflector 1341 in the X-axis direction.

The first to third reflectors 1341, 1342, and 1343 may extend in the Y-axis direction, and the second reflector 1342 and the third reflector 1343 may be disposed while being spaced apart in the X-axis direction. The first reflector 1341 may include a plurality of first through holes 1341*a* in which the plurality of ultraviolet light emitting devices 1330 are disposed.

Referring to FIG. 26, the guide portion 1317 and the recess 1311*e* may be disposed in the concave portion 1311*f*, and the recess 1311*e* may be disposed between the first guide portion 1317 and the second guide portion 1317. Accordingly, a first width W1 of the support portion 1311 from the one end portion 1311*a* to the recess 1311*e* may be smaller than a second width W2 from the one end portion 1311*a* to the guide portion 1317.

The first through hole 1341*a* of the first reflector 1341 may extend to the second reflector and the third reflector 1343. Accordingly, side surfaces of the ultraviolet light emitting device 1330 may be exposed outside the reflection member 1340 through the first through hole 1341*a*.

Referring to FIG. 27, the second reflector 1342 and the third reflector 1343 may be disposed to be tilted from the first reflector 1341 at a certain angle.

The second reflector 1342 and the third reflector 1343 may be disposed to be spaced apart from each other in the X-axis direction. A distance D1 between the second reflector 1342 and the third reflector 1343 may gradually increase in a direction away from the first circuit board 1320. For example, an angle formed between the second reflector 1342 and the third reflector 1343 may be from 20 degrees to 60 degrees but is not necessarily limited thereto.

FIG. 28 is a view illustrating the front portion of the housing of FIG. 22, FIG. 29 is a view illustrating a state in which the sterilization module is coupled to the front portion of FIG. 28, and FIG. 30 is a view illustrating the wiring portion connected to the sterilization module of FIG. 23.

Referring to FIGS. 22 and 28, the front portion 1115 may include a second fastening hole 1115a passing through from one surface to another surface of the front portion 1115. The second fastening hole 1115a may be disposed corresponding to the first fastening hole 1311d of the sterilization module 1300. Accordingly, the sterilization module 1300 may be fixed to the housing 1100 by fastening members such as bolts and the like inserted into the first fastening hole 1311d and the second fastening hole 1115a.

The front portion 1115 may include a second through hole 1115b passing through the one surface to the other surface of the front portion 1115. The second through hole 1115b may expose the connector 1140 disposed on the second circuit board 1130.

The front portion 1115 may include a pair of third through holes 1115c passing through the one surface to the other surface of the front portion 1115.

Referring to FIG. 29, the support portion 1311 of the sterilization module 1300 may be disposed on the front portion 1115 of the housing 1100.

A position of the support portion 1311 may be fixed by inserting the first and second guide portions 1317 into the third fastening hole. Here, the recess 1311e and the concave portion 1311f of the support portion 1311 may be overlapped with the second through hole 1115b of the front portion 1115. Accordingly, the connector 1140 disposed on the second circuit board 1130 may be exposed outward through the second through hole 1115b and the first recess 1311c.

Referring to FIGS. 29 and 30, a wiring portion 1600 may be connected to the first circuit board 1320.

The wiring portion 1600 may include a wire but is not necessarily limited thereto and may include another electrical component such as a flexible circuit board and the like that is capable of transmitting electricity.

The user may connect the wiring portion 1600 connected to the first circuit board 1320 to the connector 1140 while the sterilization module 1300 is disposed in the housing 1100. Here, the wiring portion 1600 may extend to an inside of the housing through the recess 1311e and the concave portion 1311f. Meanwhile, a pair of protruding portions 1315 may be utilized as a handle when the user attaches or detaches the sterilization module 1300 but is not necessarily limited thereto.

FIG. 31 is a cross-sectional view of the sterilization device of FIG. 21.

Referring to FIG. 31, the top portion 1111 of the housing 1100 may be disposed to face one surface 1030a of the handrail, and the pair of side portions 1113 may be disposed to face both side surfaces of the handrail. The second circuit board 1130 may be disposed on the top portion 1111 to face the one surface 1030a of the handrail.

The housing 1100 may include an inlet E1 and an outlet E2. The handrail may continuously pass through the housing 1100 through the inlet E1 and the outlet E2. The first elastic pad 1531 and the second elastic pad 1541 may be disposed on the inlet E1 and the outlet E2, respectively, to be spaced apart from the one surface 1030a of the handrail.

The housing 1100 may accommodate the sterilization module 1300 and the power source module 1400. The sterilization module 1300 may emit ultraviolet rays toward the one surface 1030a of the handrail, and the power source module 1400 may come into contact with the one surface 1030a of the handrail and may generate electricity to be supplied to the sterilization module 1300.

The power source module 1400 may include a roller 1410 configured to come into contact with the one surface 1030a of the handrail and a power supply portion 1420 configured to produce electricity through rotation of the roller 1410. The roller 1410 and the power supply portion 1420 may be connected by a gear (not shown). The power supply portion 1420 may include a variety of types of self-generation structures capable of converting torque of the roller 1410 into power.

The power source module 1400 may directly supply power generated by the power supply portion 1420 to the sterilization module 1300 but is not necessarily limited thereto. For example, the power source module 1400 may store and utilize part of the power generated by the power supply portion 1420 in a battery (not shown) as emergency power.

The roller 1410 and the power supply portion 1420 may be disposed in a direction from the inlet E1 to the outlet E2 of the housing 1100. That is, the roller 1410 may be disposed to be farther from the inlet E1 than the power supply portion 1420 and may be disposed to be closer to the sterilization module 1300. The above components may solve a problem in which a user's hand is drawn into an ultraviolet irradiation device due to the roller 1410.

The power supply portion 1420 may be disposed to be higher than a position at which the roller 1410 comes into contact with the one surface 1030a of the handrail by as much as a certain height h1. That is, the power supply portion 1420 may be disposed to be spaced apart from the one surface 1030a of the handrail.

The power source module 1400 may include an elastic member 1430. The elastic member 1430 may be coupled to the housing 1100 and may connect the power source module 1400 to the inlet E1 of the housing 1100.

The elastic member 1430 may press the roller 1410 against the one surface 1030a of the handrail. The elastic member 1430 may include a spring but is not necessarily limited thereto.

FIG. 32 is a cross-sectional view taken along line A-A of FIG. 31.

Referring to FIG. 32, the pair of side portions 1113 of the housing 1100 may be disposed to face both side surfaces 1030b of the handrail, respectively. The side cases 1520 of the case 1500 which surround the side portions 1113 of the housing 1100 may also be disposed to face the both side surfaces 1030b of the handrail, respectively. The fourth reflector 1521a and the fifth reflector 1521b may be coupled to the side cases 1520 by fastening members such as bolts and the like and may be disposed on both end sides of the fastening portion 1313 in the Y-axis direction to face the both side surfaces 1030b of the handrail, respectively.

The fourth reflector 1521a and the fifth reflector 1521b may reflect part of light emitted from the ultraviolet light emitting devices 1330 and may emit the reflected light toward the both side surfaces 1030b of the handrail.

The fourth reflector 1521a and the fifth reflector 1521b may be disposed to be spaced apart in the Y-axis direction, and a distance between the fourth reflector 1521a and the fifth reflector 1521b may be gradually decreased in a direction away from the first circuit board 1320. Due to the above components, even when light sources are not additionally disposed on the side surfaces 1030b of the handrail, part of the light emitted from the ultraviolet light emitting devices 1330 may be reflected by the fourth reflector 1521a and the fifth reflector 1521b and may be emitted toward the side surfaces 1030b of the handrail. The fourth reflector 1521a and the fifth reflector 1521b may have the same or different curvatures.

FIG. 33 is a perspective view illustrating a state in which an ultraviolet irradiation device according to a third embodiment of the present invention is mounted on the target structure.

Referring to FIG. 33, an ultraviolet irradiation device 2010 according to the third embodiment of the present invention may be mounted on a target structure 2020 and may sterilize a moving structure 2030 of the target structure 2020. The target structure 2020 may include all of a variety of structures such as an escalator and moving walk which transfer a user to a designated position. The moving structure 2030 may mean a handrail provided in an escalator or moving walk but is not necessarily limited thereto. Hereinafter, only a case in which the moving structure 2030 is a handrail of an escalator or moving walk will be described.

The ultraviolet irradiation device 2010 may be mounted to be exposed outside the target structure 2020 but is not necessarily limited thereto and may be mounted in the target structure 2020. In this case, a light source module may be separated from the ultraviolet irradiation device 2010 and may be separately disposed below the moving structure 2030.

FIG. 34 is a perspective view of the ultraviolet irradiation device of FIG. 33, FIG. 35 is an exploded perspective view of the ultraviolet irradiation device of FIG. 34, and FIG. 36 is a plan view illustrating a state in which a housing of FIG. 35 is fixed to the target structure.

Referring to FIGS. 34 to 36, the ultraviolet irradiation device 2010 may include a housing 2100 and a light source module 2300 and may further include a power source module 2400 and/or a case 2500.

The housing 2100 may include a first housing 2110 and a pair of second housings 2120 coupled to the first housing 2110.

The first housing 2100 may include a top portion 2111 and a pair of first side portions 2113 and may further include a front portion 2115 and/or a rear portion 2117.

The top portion 2111 may be disposed to be perpendicular to the pair of first side portions 2113, the front portion 2115, and the rear portion 2117.

The pair of first side portions 2113 may be disposed to face each other. The front portion 2115 and the rear portion 2117 may be disposed to face each other and may be disposed to be perpendicular to the pair of first side portions 2113.

A second circuit board 2130 may be disposed on the top portion 2111, and a connector 2140 may be disposed on the second circuit board 2130. The second circuit board 2130 may be an interface substrate configured to connect the light source module 2300 to the power source module 2400. The light source module 2300 may be connected to the second circuit board 2130 through the connector 2140.

The second housing 2120 may include a second side portion 2121 and a first bent portion 2123 bent from the second side portion 2121 to face the top portion 2111.

The second side portion 2121 may include a plurality of second fastening holes 2121a passing through the second side portion 2121.

The plurality of second fastening holes 2121a may be disposed at positions corresponding to a plurality of first fastening holes 2113a passing through the first side portion 2113. That is, a distance between the plurality of second fastening holes 2121a may be equal to a distance between the plurality of first fastening holes 2113a. Accordingly, the second housing 2120 may be coupled to the first housing 2110 by fastening members such as bolts and the like disposed in the first fastening holes 2113a and the second fastening holes 2121a.

A distance D3 between a pair of such first bent portions 2123 may be shorter than a distance D4 between a pair of such second side portions 2121. That is, the pair of first bent portions 2123 may be connected to the pair of second side portions 2121 and may extend in a direction of becoming closer to each other.

The first bent portion 2123 may include a third fastening hole 2123a passing through the first bent portion 2123.

In the third fastening hole 2123a, a fastening member such as a bolt and the like fastened to one surface of a support frame 2040 configured to support the moving structure 2030 may be disposed. Accordingly, the housing 2100 may be fixed to the support frame 2040 of the target structure 2020.

Although two third fastening holes 2123a are shown as being disposed for each second housing 2120 but are not necessarily limited thereto and one or three or more third fastening holes 2123a may be disposed.

The light source module 2300 may emit ultraviolet light, and the power source module 2400 may generate power to be supplied to the light source module 2300.

The light source module 2300 may be coupled to the front portion 2115 of the first housing 2110 by a fastening member such as a bolt and the like.

The power source module 2400 may be coupled to the pair of side portions 2113 of the first housing 2110.

The case 2500 may be coupled to the first housing 2100 to form an exterior of the ultraviolet irradiation device 2010. The case 2500 may include a plastic material but is not necessarily limited thereto.

The case 2500 may include a top case 2510 facing the top portion 2111 of the first housing 2110, the pair of side cases 2520 facing the pair of first side portions 2113 of the first housing 2110, and a front case 2530 facing the front portion 2115 of the first housing 2110 and may further include a rear case 2540 facing the rear portion 2117 of the first housing 2110.

The top case 2510 may include a window 2511 configured to output sterilization-related information.

The pair of side cases 2520 may include a fourth reflector 2521a and a fifth reflector 2521b coupled to the side cases 2520 by fastening members such as bolts and the like to face each other. The fourth reflector 2521a and the fifth reflector 2521b may reflect ultraviolet rays emitted from the light source module 2300. The fourth reflector 2521a and the fifth reflector 2521b may be coupled to the case 2500 instead of the light source module 2300 so as to easily attach or detach the light source module 2300. The fourth reflector 2521a and the fifth reflector 2521b may include Al but are not necessarily limited thereto and may include other materials having a high ultraviolet reflection rate.

The front case 2530 may be attached to or detached from the top case 2510. Accordingly, while the front case 2530 is separated from the top case 2510, the front portion 2115 of the first housing 2110 may be exposed outward. Also, the light source module 2300 coupled to the front portion 2115 of the first housing 2110 may be attached or detached.

The front case 2530 may include a first elastic pad 2531, and the rear case 2540 may include a second elastic pad 2541. The first elastic pad 2531 and the second elastic pad 2541 may prevent a hand of a user from being drawn into the case 2500. Also, it is possible to solve a problem in which the user's hand is caught between the case 2500 and the handrail and damaged.

The first elastic pad 2531 and the second elastic pad 2541 may include an elastic material such as silicone and the like.

The first elastic pad 2531 and the second elastic pad 2541 may be attached to or detached from the front case 2530 and the rear case 2540, respectively. For example, the front case 2530 and the rear case 2540 may include eighth fastening holes 2530*a* and 2540*a*, respectively, and the first elastic pad 2531 and the second elastic pad 2541 may include eighth protruding portions 2531*a* and 2541*a* which are inserted into the eighth fastening holes 2530*a* and 2540*a*, respectively.

FIG. 37 is a side view illustrating a state in which the housing of FIG. 35 is fixed to the target structure, and FIG. 38 is a side view illustrating a state in which the housing of FIG. 35 is fixed to a target structure having a different size.

Referring to FIGS. 37 and 38, the second fastening hole 2121*a* may have a long hole shape extending in a Z-axis direction (third direction) which connects the top portion 2111 to the first bent portion 2123. That is, a width of the second fastening hole 2121*a* in the Z-axis direction may be greater than a width in a Y-axis direction (second direction) perpendicular to the Z-axis direction and may be greater than a width of the first fastening hole in the Z-axis direction. Accordingly, even when a distance D5 between one surface of the moving structure 2030 and one surface of the support frame 2040 configured to support the moving structure 2030 varies according to a size of the target structure 2020, it is possible to adjust a distance between the light source module and the one surface of the moving structure 2030 to be uniformly maintained.

FIGS. 39 to 41 are views illustrating a process of coupling the second housing to the first housing of FIG. 35.

Referring to FIG. 39, the first side portion 2113 may include a fourth fastening hole 2113*b* passing through the first side portion 2113, and the second housing 2120 may include a first protruding portion 2125 bent from the second side portion 2121. The first protruding portion 2125 may be inserted into the fourth fastening hole 2113*b*. Here, the second side portion 2121 may be disposed to be tilted with respect to the first side portion 2113.

Referring to FIG. 40, while the first protruding portion 2125 is disposed in the fourth fastening hole 2113*b*, the second side portion 2121 may be rotated and pressed against one surface of the first side portion 2113.

The first protruding portion 2125 may extend to be parallel to a direction opposite to the second side portion 2121.

Accordingly, the first protruding portion 2125 may be pressed against another surface of the first side portion 2113 and may stably support the second side portion 2121. Also, it is possible to facilitate a bolt-fastening operation between the first housing 2110 and the second housing 2120.

Referring to FIG. 41, coupling between the first housing 2110 and the second housing 2120 may be completed through fastening of a fastening member such as a bolt and the like.

FIG. 42 is a perspective view illustrating the light source module of FIG. 35, and FIG. 43 is an exploded perspective view of the light source module of FIG. 42.

Referring to FIGS. 42 and 43, the light source module 2300 may include a frame 2310, a first circuit board 2320, and a plurality of ultraviolet light emitting devices 2330 and may further include a reflection member 2340.

The frame 2310 may include a fixing portion 2311, a second bent portion 2313 bent from the fixing portion 2311, and a pair of second protruding portions 2315 bent from both ends of the fixing portion 2311 to face each other and may further include a pair of third protruding portions 2317 bent from the fixing portion 2311 to face the second bent portion 2313.

The second bent portion 2313 and the second protruding portions 2315 may be bent from the fixing portion 2311 in mutually opposite directions. For example, the second bent portion 2313 may be bent below the fixing portion 2311, and the second protruding portion 2315 may be bent above the fixing portion 2311.

The frame 2310 may include Al but is not necessarily limited thereto and may include other materials having an excellent heat dissipation property. The first circuit board 2320 may be disposed on the second bent portion 2313.

The first circuit board 2320 may include a wire (not shown) used for power supply or the like.

The plurality of ultraviolet light emitting devices 2330 may be disposed in a row on the first circuit board 2320.

The ultraviolet light emitting devices 2330 may output light UV-A of a near-ultraviolet wavelength range, may output light UV-B of a far-ultraviolet wavelength range, and may output light UV-C of a deep-ultraviolet wavelength range. A wavelength range of light may be determined by a composition ratio of Al in a semiconductor structure.

For example, the light UV-A of the near-ultraviolet wavelength range may have a range from 320 nm to 420 nm, the light UV-B of the far-ultraviolet wavelength range may have a range from 280 nm to 320 nm, and the light UV-C of the deep-ultraviolet wavelength range may have a range from 100 nm to 280 nm.

The reflection member 2340 may be disposed on the first circuit board 2320. The reflection member 2340 and the first circuit board 2320 may be fixed together to the second bent portion 2313 by a fastening member such as a bolt and the like.

The reflection member 2340 may reflect light emitted from the ultraviolet light emitting devices 2330. Also, the reflection member 2340 may perform a heat dissipation function of externally dissipating heat generated from the ultraviolet light emitting devices 2330. It may be significant for the ultraviolet light emitting device 2330 to quickly dissipate heat.

The reflection member 2340 may include Al but is not necessarily limited thereto and may include other materials having a high ultraviolet light reflectance.

FIG. 44 is a front view of the light source module of FIG. 42, FIG. 45 is a plan view of the light source module of FIG. 42, and FIG. 46 is a side view of the light source module of FIG. 42.

Referring to FIG. 44, the frame 2310 may include a pair of fourth protruding portions 2319*a* bent from one end of the second bent portion 2313 in the Y-axis direction (second direction) perpendicular to the X-axis direction (first direction) and may include a pair of fifth protruding portions 2319*b* bent from another end of the second bent portion 2313 in the second direction. The fourth protruding portions 2319*a* may be disposed below the fifth protruding portions 2319*b*. That is, a distance between the fixing portion 2311 and the fourth protruding portions 2319*a* may be greater than a distance between the fixing portion 2311 and the fifth protruding portions 2319*b*.

The fourth protruding portions 2319*a* and the fifth protruding portions 2319*b* may be adjacent to side surfaces of the first circuit board 2320 which face each other. Particularly, the pair of fourth protruding portions 2319*a* may be disposed in a pair of second recesses 2320*a* formed in the first circuit board 2320. Accordingly, the first circuit board 2320 may be stably supported, on the second bent portion 2313, by the fourth protruding portions 2319a and the fifth protruding portions 2319b. As a result, a user may fasten a fastening member such as a bolt and the like while the first circuit board 2320 is stably supported.

The fourth protruding portions 2319a and the fifth protruding portions 2319b may be disposed while being spaced apart in the X-axis direction. That is, the fourth protruding portions 2319a and the fifth protruding portions 2319b may be mutually misaligned. Accordingly, an area in which a circuit pattern (not shown) of the first circuit board 2320 may be formed without interference with the second recesses 2320a may be secured above or below the ultraviolet light emitting devices 2330.

The plurality of ultraviolet light emitting devices 2330 may be disposed to be spaced apart from each other in the X-axis direction.

The reflection member 2340 may include a first reflector 2341 disposed on the first circuit board 2320 and second and third reflectors 2342 and 2343 bent from both ends of the first reflector 2341 in the Y-axis direction.

The first to third reflectors 2341, 2342, and 2343 may extend in the X-axis direction, and the second reflector 2342 and the third reflector 2343 may be disposed while being spaced apart in the Y-axis direction. The first reflector 2341 may include a plurality of first through holes 2341a in which the plurality of ultraviolet light emitting devices 2330 are disposed.

Referring to FIG. 45, the fixing portion 2311 may include a first side surface 2311a connected to the second bent portion 2313, a second side surface 2311b facing the first side surface 2311a, a first recess 2311c formed in the second side surface 2311b to be concave toward the first side surface 2311a, and a fifth fastening hole 2311d passing through one surface and another surface of the fixing portion 2311.

The fixing portion 2311 may include a pair of convex portions 2311e protruding into the first recess 2311c and connected to the pair of third protruding portions 2317, respectively, and a concave portion 2311f disposed between the pair of protruding portions 311e. The convex portions 2311e may extend in the Z-axis direction (third direction) perpendicular to the X-axis direction and the Y-axis direction, and the pair of convex portions 2311e may be disposed to be spaced apart from each other in the X-axis direction. Accordingly, the fixing portion 2311 may have a first width W1 from the first side surface 2311a to the concave portion 2311f which is smaller than a second width W2 from the first side surface 2311a to the convex portion 2311e. In other words, a width of the first recess 2311c may be extended by as much as a width of the concave portion 2311f.

The first through hole 2341a of the first reflector 2341 may extend to the second reflector and the third reflector 2343. Accordingly, side surfaces of the ultraviolet light emitting device 2330 may be exposed outside the reflection member 2340 through the first through hole 2341a.

Referring to FIG. 46, the second reflector 2342 and the third reflector 2343 may be disposed to be tilted from the first reflector 2341 at a certain angle.

The second reflector 2342 and the third reflector 2343 may be disposed to be spaced apart from each other in the Y-axis direction. A distance D1 between the second reflector 2342 and the third reflector 2343 may gradually increase in a direction away from the first circuit board 2320. For example, an angle formed between the second reflector 2342 and the third reflector 2343 may be from 20 degrees to 60 degrees but is not necessarily limited thereto.

FIG. 47 is a plan view illustrating the front portion of the first housing of FIG. 35, and FIG. 48 is a view illustrating a state in which the light source module is coupled to the front portion of FIG. 47.

Referring to FIGS. 35 and 47, the front portion 2115 may include a sixth fastening hole 2115a passing through the front portion 2115. The sixth fastening hole 2115a may be disposed corresponding to the fifth fastening hole 2311d of the light source module 2300. Accordingly, the light source module 2300 may be fixed to the first housing 2110 by fastening members such as bolts and the like inserted into the fifth fastening hole 2311d and the sixth fastening hole 2115a.

The front portion 2115 may include a second through hole 2115b passing through the front portion 2115. The second through hole 2115b may expose the connector 2140 disposed on the second circuit board 2130.

The front portion 2115 may include a pair of seventh fastening holes 2115c passing through the front portion 2115. The third protruding portion 2317 of the light source module 2300 may be inserted into the seventh fastening hole 2115c. Accordingly, a user may fix a position of the light source module 2300 by inserting the third protruding portion 2317 into the seventh fastening hole 2115c. In this state, the light source module 2300 may be coupled to the first housing 2110 by a fastening member such as a bolt and the like.

Referring to FIG. 48, the light source module 2300 may be fixed to the front portion 2115 of the first housing 2110 by a fastening member such as a bolt and the like. Here, the first recess 2311c of the fixing portion 2311 may be overlapped with the second through hole 2115b of the front portion 2115. Accordingly, the connector 2140 disposed on the second circuit board 2130 may be exposed outward through the second through hole 2115b and the first recess 2311c. As a result, while the light source module 2300 is stably fixed to the housing 2100 first, the user may connect a wire (not shown) of the first circuit board 2320 to the connector 2140 of the second circuit board 2130. Also, the concave portion 2311f of the fixing portion 2311 may also be overlapped with the second through hole 2115b of the front portion 2115 so as to further improve a wire connection operation. Meanwhile, the pair of second protruding portions 2315 may be utilized as a handle when the user attaches or detaches the light source module 2300 but is not necessarily limited thereto.

FIG. 49 is a cross-sectional view of the ultraviolet irradiation device of FIG. 34.

Referring to FIG. 49, the housing 2100 may include an inlet E1 and an outlet E2. The handrail may continuously pass through the housing 2100 through the inlet E1 and the outlet E2. The first elastic pad 2531 and the second elastic pad 2541 may be disposed on the inlet E1 and the outlet E2, respectively, to be spaced apart from one surface 2030a of the handrail.

The top portion 2111 of the first housing 2110 may be disposed to face the one surface 2030a of the handrail, and the pair of first side portions 2113 may be disposed to face both side surfaces of the handrail. The second circuit board 2130 may be disposed on the top portion 2111 to face the one surface 2030a of the handrail.

The first housing 2110 may accommodate the light source module 2300 and the power source module 2400. The light source module 2300 may emit ultraviolet light toward the one surface 2030a of the handrail, and the power source module 2400 may come into contact with the one surface 2030a of the handrail and may generate power to be supplied to the light source module 2300.

The power source module 2400 may include a roller 2410 configured to come into contact with the one surface 2030a of the handrail and a power supply portion 2420 configured to produce power through rotation of the roller 2410. The roller 2410 and the power supply portion 2420 may be connected by a gear (not shown). The power supply portion 2420 may include a variety of types of self-generation structures capable of converting torque of the roller 2410 into power.

The power source module 2400 may directly supply power generated by the power supply portion 2420 to the light source module 2300 but is not necessarily limited thereto. For example, the power source module 2400 may store and utilize part of the power generated by the power supply portion 2420 in a battery (not shown) as emergency power.

The roller 2410 and the power supply portion 2420 may be disposed in a direction from the inlet E1 to the outlet E2 of the housing 2100. That is, the roller 2410 may be disposed to be farther from the inlet E1 than the power supply portion 2420 and may be disposed to be closer to the light source module 2300. The above components may solve a problem in which a user's hand is drawn into an ultraviolet irradiation device due to the roller 2410.

The power supply portion 2420 may be disposed to be higher than a position at which the roller 2410 comes into contact with the one surface 2030a of the handrail by as much as a certain height h1. That is, the power supply portion 2420 may be disposed to be spaced apart from the one surface 2030a of the handrail.

The power source module 2400 may be rotatably coupled to the pair of first side portions 2113 of the first housing 2110 through a rotating shaft 2400a and may include an elastic member 2430. The elastic member 2430 may rotate the power source module 2400 so as to press the roller 2410 against the one surface 2030a of the handrail. The elastic member 2430 may be coupled to the rotating shaft 2400a. The elastic member 2430 may include a spring but is not necessarily limited thereto. Also, the power source module 2400 may have a limited rotation range. For example, the power source module 2400 may come into contact with the top portion 2111 of the first housing 2110 so as to restrict clockwise rotation and may come into contact with a stopper pin 2113c coupled to the first side portion 2113 so as to restrict counterclockwise rotation. Accordingly, stability of a product, work convenience, and the like may be improved.

FIG. 50 is a cross-sectional view taken along line A-A of FIG. 49.

Referring to FIG. 50, the pair of first side portions 2113 of the first housing 2110 may be disposed to face both side surfaces 2030b of the handrail, respectively. Accordingly, the side cases 2520 configured to surround the first side portions 2113 of the first housing 2110 may also be disposed to face the both side surfaces 2030b of the handrail. The fourth reflector 2521a and the fifth reflector 2521b may be coupled to the side cases 2520 by fastening members such as bolts and the like and may be disposed to face the both side surfaces 2030b of the handrail, respectively.

The fourth reflector 2521a and the fifth reflector 2521b may reflect part of light emitted from the ultraviolet light emitting devices 2330 and may emit the reflected light toward the both side surfaces 2030b of the handrail.

The fourth reflector 2521a and the fifth reflector 2521b may be disposed to be spaced apart in the X-axis direction, and a distance between the fourth reflector 2521a and the fifth reflector 2521b may be gradually decreased in a direction away from the first circuit board 2320. Due to the above components, even when light sources are not disposed additionally on the side surfaces 2030b of the handrail, part of the light emitted from the ultraviolet light emitting devices 2330 may be reflected by the fourth reflector 2521a and the fifth reflector 2521b and may be emitted toward the side surfaces 2030b of the handrail. The fourth reflector 2521a and the fifth reflector 2521b may have the same or different curvatures.

FIG. 51 is a perspective view illustrating an ultraviolet irradiation device according to a fourth embodiment of the present invention, and FIG. 52 is an exploded perspective view of a housing and a fixing portion of FIG. 51.

Referring to FIG. 51, an ultraviolet irradiation device 2010' according to the fourth embodiment of the present invention may include a housing 2100, a coupling portion 2200, and a light source module (not shown) and may further include a power source module (not shown) and/or a case 2500. Since the light source module, the power source module, and the case 2500 are substantially equal to those applied to the ultraviolet irradiation device 2010 according to the third embodiment of the present invention, a description thereof will be omitted.

Referring to FIG. 52, the housing 2100 may include a first housing 2100 and a pair of third housings 2150 coupled to the first housing 2100.

The first housing 2100 may include a top portion 2111 and a pair of first side portions 2113 and may further include a front portion 2115 and/or a rear portion 2117.

The top portion 2111 may be disposed to be perpendicular to the pair of first side portions 2113, the front portion 2115, and the rear portion 2117.

The pair of first side portions 2113 may be disposed to face each other. The front portion 2115 and the rear portion 2117 may be disposed to face each other and may be disposed to be perpendicular to the pair of first side portions 2113.

The third housing 2150 may include a third side portion 2151, and the third side portion 2151 may include a plurality of ninth fastening holes 2151a passing through the third side portion 2151.

The plurality of ninth fastening holes 2151a may be disposed at positions corresponding to a plurality of first fastening holes 2113a passing through the first side portion 2113. That is, a distance between the plurality of ninth fastening holes 2151a may be equal to a distance between the plurality of first fastening holes 2113a. Accordingly, the third housing 2150 may be coupled to the first housing 2110 by fastening members such as bolts and the like disposed in the first fastening holes 2113a and the ninth fastening holes 2151a.

The coupling portion 2200 may fix the housing 2100 to a target structure. The coupling portion 2200 may include first and second coupling plates 2210 and 2220 coupled to a pair of such third side portions 2151, respectively, and a plurality of nuts 2230 and 2240 disposed between the third side portion 2151 and the first coupling plate 2210 and/or between the third side portion 2151 and the second coupling plate 2220. The plurality of nuts 2230 and 2240 may include a pair of first nuts 2230 and a pair of second nuts 2240 shorter than the first nuts 2230.

The third side portions 2151, the first coupling plate 2210, the second coupling plate 2220, and the nuts 2230 and 2240 may be coupled to one another using bolts. Here, the bolts may include stud bolts.

FIGS. 53 to 56 are views illustrating a variety of examples of installing the ultraviolet irradiation device of FIG. 51.

Referring to FIGS. 53 to 56, a target structure 2020 may include a plate 2050 disposed inside a moving structure 2030, for example, a handrail rotating on an infinite orbit and configured to support the moving structure 2030. The plate 2050 may be a glass plate but is not necessarily limited thereto.

A position of the plate 2050 may vary according to a type of the target structure 2020. For example, the plate may be disposed on a central line A of the moving structure 2030 as shown in FIG. 55 or may be disposed to be spaced at a certain distance e apart from the central line A of the moving structure 2030 as shown in FIGS. 53, 54, and 56. Accordingly, a distance a between one first side portion 2151 and the first coupling plate 2210 and a distance b between the other first side portion 2151 and the second coupling plate 2220 may be adjusted using a variety of arrangements of the pair of first nuts 2230 and the pair of second nuts 2240.

A length c1 of the first nut 2230 may be longer than a length c2 of the second nut 2240 by two or three times, and preferably, by 2.5 times.

The length c1 of the first nut 2230 may be 22 mm to 28 mm, and preferably, 25 mm. The length c2 of the second nut 2240 may be 9 mm to 11 mm, and preferably, 10 mm.

A thickness t1 of the first coupling plate 2210 and the second coupling plate 2220 may be 10 mm to 12 mm, and preferably, 11 mm. Films f may be attached to surfaces of the first coupling plate 2210 and the second coupling plate 2220 which face each other. A thickness t2 of the films f may be 0.9 mm to 1.1 mm, and preferably, 1 mm. A thickness t3 of the plate 2050 may be 6 mm to 10 mm, and preferably, 8 mm.

A distance d1 between the pair of third side portions 2151 may be 110 mm to 120 mm, and preferably, 114 mm.

A length which is adjustable by a bolt coupled to the first nut 2230 may be 0 mm to 13 mm. That is, it is possible to adjust a distance between the first coupling plate 2210 and the second coupling plate 2220 by adjusting a protruding length d2 of the bolt coupled to the first nut 2230.

FIG. 57 illustrates a basic example of the ultraviolet irradiation device of FIG. 33.

Referring to FIG. 57, the ultraviolet irradiation device 2010 may include the first housing 2110, a pair of such second housings 2120, and the light source module 2300. The first housing 2110 may include the top portion 2111 and the pair of first side portions 2113 facing each other with the top portion 2111 therebetween. The pair of second housings 2120 may be coupled to the pair of first side portions 2113, respectively. The second housing 2120 may include second side portions 2121 connected to the first side portions 2113 and first bent portions 2123 bent from the second side portions 2121 to face the top portion 2111. The first side portion 111 may include a plurality of first fastening holes 2113a passing through the first side portion 111. The second side portion 2121 may include a plurality of second fastening holes 2121a passing through the second side portion 2121 at positions corresponding to the plurality of first fastening holes 2113a. The first bent portion 2123 may include a third fastening hole 2123a passing through the first bent portion 2123. The second fastening holes 2121a may have a long hole shape longer than the first fastening holes 2113a in a direction toward the top portion 2111 and the first bent portion 2123, for example, in the Z-axis direction. The above description with reference to FIGS. 33 to 50 may be applied equally to the ultraviolet irradiation device 2010 of FIG. 57.

There is provided a method of installing an ultraviolet irradiation device on a moving structure. Here, the ultraviolet irradiation device includes a first housing including a top portion and a pair of first side portions facing each other with the top portion therebetween; a pair of second housings coupled to the pair of first side portions, respectively; and a light source module disposed on the top portion of the first housing. The second housings each include second side portions connected to the first side portions and first bent portions bent from the second side portions to face the top portion. The first side portions each include a plurality of first fastening holes passing through the first side portions. The second side portions each include a plurality of second fastening holes passing through the second side portions at positions corresponding to the plurality of first fastening holes. The first bent portions each include a plurality of third fastening holes passing through the first bent portions. The second fastening holes have a long hole shape longer than the first fastening holes in a direction toward the top portion and the first bent portions. The method may include disposing the first bent portions of the second housing on a support frame of the moving structure; fixing the second housings to a target structure by fastening fastening members such as bolts and the like to the support frame through the third fastening holes; connecting first side portions of the first housing to second side portions of the second housings by disposing fastening members such as bolts and the like in the first fastening holes and the second fastening holes; and disposing the light source module on the top portion of the first housing to face one surface of the moving structure. In the above, respective operations of the method of installing the ultraviolet irradiation device are not restricted by an order. The components stated in the method of installing the ultraviolet irradiation device may be referred to as the same reference numerals as the components having the same designations described with reference to FIGS. 33 to 56.

Although the embodiments have been described above, the embodiments are merely examples and are not intended to limit the present invention and it may be seen that a variety of modifications and applications not described above may be made by one of ordinary skill in the art without departing from the essential features of the embodiments. For example, the components described in the embodiments may be implemented while being modified. Also, it should be noted that differences related to the modifications and applications are included within the scope of the present invention defined by following the claims.

The invention claimed is:

1. A sterilization module comprising:
   a frame comprising a support portion comprising one surface and one end portion and a fastening portion connected to the one end portion;
   a first circuit board disposed on the fastening portion; and
   an ultraviolet light emitting device disposed on the first circuit board,
   wherein the support portion comprises another end portion opposite to the one end portion and side end portions facing each other with the other end portion therebetween,
   wherein the frame comprises a protruding portion connected to the side end portions of the support portion and a guide portion connected to the other end portion of the support portion.

2. The sterilization module of claim 1, wherein the fastening portion and the guide portion extend in a first direction perpendicular to the one surface of the support portion, and
   wherein the protruding portion extends in a direction opposite to the first direction.

3. The sterilization module of claim 2, wherein the guide portion comprises a first guide portion and a second guide portion disposed to be spaced apart from each other in a second direction parallel to the one end portion.

4. The sterilization module of claim 3, wherein the other end portion comprises a recess between the first guide portion and the second guide portion, and wherein the recess is concave toward the one end portion.

5. The sterilization module of claim 1, wherein the side end portions comprise a first side end portion and a second side end portion to face each other, and
wherein the protruding portion comprises a first protruding portion and a second protruding portion connected to the first side end portion and the second side end portion, respectively.

6. The sterilization module of claim 3, wherein the support portion comprises a first fastening hole passing through the one surface to another surface of the support portion.

7. The sterilization module of claim 6, wherein the first fastening hole comprise a 1-1 fastening hole and a 1-2 fastening hole which are disposed to be spaced apart from each other in the second direction.

8. The sterilization module of claim 6, wherein the first fastening hole is disposed to be closer to the side end portion than the guide portion.

9. The sterilization module of claim 4, wherein the other end portion comprises a concave portion concave toward the one end portion, and
wherein the guide portion and the recess are disposed in the concave portion.

10. The sterilization module of claim 3, the ultraviolet light emitting device is disposed to be spaced part from each other in the second direction.

11. The sterilization module of claim 3, comprising a reflection member disposed on the first circuit board,
wherein the reflection member comprises:
a first reflector disposed on the first circuit board; and
a second reflector and a third reflector connected to both ends of the first reflector in the first direction,
wherein the first reflector comprises a first through hole in which the ultraviolet light emitting device is disposed, and
wherein a distance between the second reflector and the third reflector gradually increases in a direction away from the first circuit board.

12. A sterilization device comprising:
a case;
a housing disposed in the case;
a sterilization module disposed in the housing;
a first cover disposed above the sterilization module; and
a wiring portion configured to supply power to the sterilization module,
wherein the sterilization module comprises:
a frame comprising a support portion comprising one surface and one end portion and a fastening portion connected to the one end portion;
a first circuit board disposed on the fastening portion; and
an ultraviolet light emitting device disposed on the first circuit board,
wherein the support portion comprises another end portion opposite to the one end portion and side end portions facing each other with the other end portion therebetween,
wherein the frame comprises a protruding portion connected to the side end portions of the support portion and a guide portion connected to the other end portion of the support portion.

13. The sterilization device of claim 12, wherein the fastening portion and the guide portion extend in a first direction perpendicular to the one surface of the support portion, and
wherein the protruding portion extends in a direction opposite to the first direction.

14. The sterilization device of claim 12, wherein the other end portion comprises a recess concave toward the one end portion, and
wherein the wiring portion is connected to the first circuit board and extends toward an inside of the housing through the recess.

15. The sterilization device of claim 14, wherein the guide portion comprises a first guide portion and a second guide portion spaced apart in a second direction parallel to the one end portion, and the recess is disposed between the first guide portion and the second guide portion.

16. The sterilization device of claim 14, comprising:
a second circuit board disposed inside the housing; and
a connector disposed on the second circuit board,
wherein the wiring portion is connected to the connector.

17. The sterilization device of claim 15, wherein the support portion is disposed on a front portion of the housing,
wherein the support portion comprises a first fastening hole passing through the one surface to another surface of the support portion,
wherein the front portion comprises a second through hole overlapped with the recess, a second fastening hole corresponding to the first fastening hole, and a pair of third fastening holes passing through the front portion.

18. The sterilization device of claim 17, wherein the first guide portion and the second guide portion are disposed in the pair of third fastening holes.

19. The sterilization device of claim 18, wherein the sterilization module is fixed to the housing by a fastening member coupled to the first cover and extending to the first fastening hole and the second fastening hole.

20. The sterilization device of claim 16, comprising a fourth reflector and a fifth reflector disposed in the case,
wherein the fourth reflector and the fifth reflector are disposed on both end sides of the fastening portion in a second direction parallel to the one end portion, and
wherein a distance between the fourth reflector and the fifth reflector is gradually reduced in a direction away from the first circuit board.

* * * * *